US007629475B2

(12) United States Patent
Béquin et al.

(10) Patent No.: US 7,629,475 B2
(45) Date of Patent: Dec. 8, 2009

(54) SALVINORIN DERIVATIVES AND USES THEREOF

(75) Inventors: Cécile Béquin, Lexington, MA (US); William A. Carlezon, Lincoln, MA (US); Bruce M. Cohen, Lexington, MA (US); Minsheng He, Allston, MA (US); David Yue-Wei Lee, Cambridge, MA (US); Michele R. Richards, Mansfield, MA (US); Lee-Yuan Liu-Chen, Media, PA (US)

(73) Assignee: The McLean Hospital Corporation, Belmont, MA (US)

( * ) Notice: Subject to any disclaimer, the term of this patent is extended or adjusted under 35 U.S.C. 154(b) by 0 days.

(21) Appl. No.: 11/079,825

(22) Filed: Mar. 14, 2005

(65) Prior Publication Data
US 2006/0052439 A1    Mar. 9, 2006

Related U.S. Application Data

(60) Provisional application No. 60/552,669, filed on Mar. 12, 2004, provisional application No. 60/630,903, filed on Nov. 24, 2004.

(51) Int. Cl.
*C07D 311/78*    (2006.01)
(52) U.S. Cl. .................................... 549/280
(58) Field of Classification Search ................. 549/280
See application file for complete search history.

(56) References Cited

U.S. PATENT DOCUMENTS

2006/0058264 A1*    3/2006    Prisinzano ................... 514/63
2006/0083679 A1*    4/2006    Zjawiony et al. ........... 424/1.11

FOREIGN PATENT DOCUMENTS

WO    WO 02/49643    6/2002
WO    WO 2005/089745    9/2005

OTHER PUBLICATIONS

Siebert et al., Annals of Botany, "Localization of salvinorin A and related compounds in glandular trichomes of the psychoactive sage, salvia divinorum", 2004, vol. 93, pp. 763-771.*
Chavkin et al., Journal of pharmacology and experimental therapeutics, "Salvinorin A, and active component of the hallucinogenic sage salvia divinorum is a highly efficacious K-Opioid receptor agonist: structural and functional considerations", 2004, vol. 304, pp. 1197-1203.*
Bigham et al., Journal of natural products, "Divinatorins A-C, New neoclerodane diterpenoids from the controlled sage salvia divinorum", 2003, vol. 66, pp. 1242-1244.*
Munro et al., Journal of natural products, "Salvinorins D-F, new neoclerodane diterpenoids from salvia divinorum, and an improved method for the isolation of salvinorin A", 2003, vol. 66, pp. 703-705.*

Sheffler et al., Trends in pharmacological sciences, "Salvinorin A: the 'magic mint' hallucinogen finds a molecular target in the kappa opioid receptor", 2003, vol. 24, pp. 107-109.*
Roth et al., Proceedings of the national academy of sciences of the united states of america, "Salvinorin A: A potent naturally occurring nonnitrogenous K opioid selective agonist", 2002, vol. 99, pp. 11934-11939.*
Valdes et al., Organic Letters, "Salvinorin C, a new neoclerodane diterpene from a bioactive fraction of the hallucinogenic mexican mint salvia divinorum", 2001, vol. 3, pp. 3935-3937.*
Giroud et al., Forensic science international, "Salvia divinorum: an hallucinogenic mint which might become a new recreational drug in Switzerland", 2000, vol. 112, pp. 143-150.*
Koreeda et al., Chemistry Letters, "The absolute stereochemistry of salvinorins", 1990, vol. 11, pp. 2015-2018.*
Bigham et al., "Divinatorins A-C, New Neoclerodane Diterpenoids from the Controlled Sage *Salvia Divinorum*," *J. Nat. Prod.* 66: 1242-1244 (2003).
Beguin et al., "Synthesis and in vitro evaluation of salvinorin A analogues: effect of configuration at C(2) and substitution at C(18)," *Biorg Med Chem Lett.* 16:4679-4685 (2006).
Beguin et al., "Synthesis and in vitro pharmacological evaluation of salvinorin A analogues modified at C(2)," *Bioorg Med Chem Lett.* 15:2761-2765 (2005).
Butelman et al., "The Plant-Derived Hallucinogen, Salvinorin A, Produces κ-Opioid Agonist-Like Discriminative Effects in Rhesus Monkeys," *Psychopharmacol.* 172:220-224 (2004).
Carlezon et al., Depressive-like effects of the kappa-opiold receptor agonist salvinorin A on behavior and neurochemistry in rats, *J Pharmacol Exp Ther.* 316:440-447 (2006).
Chavkin et al., "Salvinorin A, An Active component of the Hallucinogenic Sage *Salvia Divinorum* is a Highly Efficacious $_\kappa$-Opioid Receptor Agonist: Structural and Functional Considerations," *J. Pharmacol. Exp. Ther.* 308: 1197-1203 (2004).
Chupp et al., "Behavior of Benzyl Sulfoxides Toward Acid Chlorides. Useful Departures from the Pummerer Reaction," *J. Org. Chem.* 49:4711-4716 (1984).
Giroud et al., "*Salvia Divinorum*: An Hallucinogenic Mint Which Might Become a New Recreational Drug in Switzerland," *Forensic Sci. Int.* 112: 143-150 (2000).
Huang et al., "Comparison of Pharmacological Activities of Buprenorphine and Norbuprenorphine: Norbuprenorphine is a Potent Opioid Agonist," *J. Pharmacol. Exp. Ther.* 297:688-695 (2001).
Koreeda et al., "The Absolute Stereochemistry of Salvinorins," *Chem. Lett.* 19:2015-2018 (1990).

(Continued)

*Primary Examiner*—D. Margaret Seaman
*Assistant Examiner*—Niloofar Rahmani
(74) *Attorney, Agent, or Firm*—Clark & Elbing LLP; Paul T. Clark

(57) ABSTRACT

The invention features salvinorin compositions that are selective for kappa opioid receptors; methods of treating mania by using a selective kappa receptor agonist; and methods of treating mood disorders, such as depressive disorders and manic disorders, using salvinorin compositions.

13 Claims, 4 Drawing Sheets

OTHER PUBLICATIONS

Lee et al., "Synthesis and in vitro pharmacological studies of C(4) modified salvinorin A analogues," *Bioorg Med Chem Lett.* 15:4169-4173 (2005).

Lee et al., "Synthesis and in vitro pharmacological studies of new C(2) modified salvinorin A analogues," *Bioorg Med Chem Lett.* 15:3744-3747 (2005).

Ma et al., "Dynorphinergic Gaba Neurons are a Target of Both Typical and Atypical Antipsychotic Drugs in the Nucleus Accumbens Shell, Central Amygdaloid Nucleus and Thalamic Central Medial Nucleus," *Neuroscience* 121:991-998 (2003).

Mague et al., "Antidepressant-Like Effects of κ-Opioid Receptor Antagonists in the Forced Swim Test in Rats," *J. Pharmacol. Exp. Ther.* 305:323-330 (2003).

McCurdy et al., "Studies Directed Toward Understanding the Opioid Receptor Recognition of Salvinorin A, a Non-Nitrogenous Natural Product with Kappa Opioid Receptor Selectivity," *2003 Narcotics Research Conference*, Abstract #28, p. 51.

Munro et al., "8-epi-Salvinorin B: crystal structure and affinity at the kappa opioid receptor," *Beilstein J Org Chem.* 3:1-5 (2007).

Munro et al., "Studies Toward the Pharmacophore of Salvinorin A, A Potent Kappa Opioid Receptor Agonist," *J. Med. Chem.* 48: 345-348 (2005).

Munro et al., Salvinorins D-F, New Neoclerodane Diterpenoids from the Salvia divinorum, and an Improved Method for the Isolation of Salvinorin A, *J. Nat. Prod.* 66:703-705 (2003).

Pliakas et al., "Altered Responsiveness to Cocaine and Increased Immobility in the Forced Swim Test Associated with Elevated cAMP Response Element-Binding Protein Expression in Nucleus Accumbens," *J. Neurosci.* 21:7397-7403 (2001).

Roth et al., "Salvinorin A: A Potent Naturally Occurring Nonnitrogenous Kappa Opioid Selective Agonist," *Proc. Nat. Acad. Sci. USA* 99:11934-11939 (2002).

Sheffler et al., "Salvinorin A: The 'Magic Mint' Hallucinogen Finds a Molecular Target in the Kappa Opioid Receptor," *Trends Pharm. Sci.* 24: 107-109 (2003).

Siebert, Daniel J., "Localization of Salvinorin A and Related Compounds in Glandular Trichomes of the Psychoactive Sage, *Salvio divinorum*," *Annals of Botany* 93: 763-771 (2004).

Valdés et al., "Salvinorin C, a New Neoclerodane Diterpene from a Bioactive Fraction of the Hallucinogenic Mexican Mint *Salvia divinorum*," Org. Lett. 3:3935-3937 (2001).

Valdés et al., "Divinorin A, a Psychotropic Terpenoid, and Divinorin B from the Hallucinogenic Mexican Mint *Salvia Divinorum*," *J. Org. Chem.* 49:4716-4720 (1984).

Zdero et al., "*Ent*-Clerodanes and Other Constituents from Bolivian *Baccharis* species," *Phytochem.* 28:531-542 (1989).

Zhang et al., "Kappa Agonist Salvinorin A Induced Conditioned Place Aversion in C57BL/6J Mice," *2003 Narcotics Research Conference*, Abstract #102, p. 70.

Zhu et al., "Activation of the Cloned Human Kappa Opioid Receptor by Agonists Enhances [$^{35}$S]GTPγS Binding to Membranes: Determination of Potencies and Efficacies of Ligands," *J. Pharmacol. Exp. Ther.* 282:676-684 (1997).

International Search Report for PCT/US05/08603 dated Jun. 16, 2005.

International Preliminary Report on Patentability for PCT/US05/08603 dated Sep. 13, 2006.

Béguin et al., "N-Methylacetamide Analog of Salvinorin A: A Highly Potent and Selective k-Opioid Receptor Agonist with Oral Efficacy," *J. Pharmacol. Exp. Ther*, 324(1):188-195 (2008).

Harding et al., "Synthetic Studies of Neoclerodane Diterpenes From Salvia Divinorum: Selective Modification of the Furan Ring," *Bioorg. Med. Chem. Lett.* 16:3170-3174 (2006).

Harding et al., "Synthetic Studies of Neoclerodane Diterpenes From Salvia Divinorum: Semisynthesis of Salvinicins A and B and Other Chemical Transformations of Salvinorin A," *J. Nat. Prod.* 69(1):107-112 (2006).

Simpson et al., "Synthetic Studies of Neoclerodane Diterpenes from Salvia Divinorum: Preparation and Opioid Receptor Activity of Salvinicin Analogues," *J. Med. Chem.* 50(15):3596-3603 (2007).

\* cited by examiner

SALVINORIN DERIVATIVES AND USES THEREOF

CROSS-REFERENCE TO RELATED APPLICATIONS

The application claims benefit of U.S. Provisional Application Nos. 60/552,669, filed Mar. 12, 2004, and 60/630,903, filed Nov. 24, 2004, each of which is incorporated herein by reference.

BACKGROUND OF THE INVENTION

The invention relates to the treatment of depressive disorders and mania.

Stressors that cause symptoms of depression increase the activation of cAMP response element-binding protein (CREB) in the nucleus accumbens. CREB activation results in the activation of the prodynorphin gene, which encodes the opioid peptide dynorphin. Dynorphin is an agonist of the kappa opioid receptors in the brain, and enhances symptoms of depression. It has been shown that kappa receptor antagonists can act as antidepressants by mediating a disinhibition of dopamine release in the nucleus accumbens. See Pliakas et al., *J. Neurosci.* 21:7397 (2001); and Mague et al., *J. Pharmacol. Exp. Ther.* 305:323 (2003). It has been shown that antimanic/antipsychotic drugs increase the activity of dynorphinergic neurons, which have their effects through kappa receptors (Ma et al., *Neuroscience* 121:991 (2003).

The diterpene salvinorin A, derived from *Salvia divinorum*, has recently been shown to be a high affinity and selective kappa opioid receptor agonist. See Roth et al., *Proc. Natl. Acad. Sci. USA* 99:11934 (2002); and Butelman et al., *Psychopharmacology* 172:220 (2004).

New compounds which are highly selective for kappa opioid receptors over mu and delta opioid receptors and which have kappa antagonist, kappa partial agonist, or kappa agonist activity are needed to provide improved methods for the treatment of affective disorders and other conditions for which kappa opioid receptor signaling plays a role in the pathogenesis of disease.

SUMMARY OF THE INVENTION

The invention is based on the discovery of compounds that are selective for kappa opioid receptors. The modulation of activity at kappa opioid receptors can be useful for the treatment of mood disorders. For example, the compounds exhibiting antagonist activity at kappa receptors are useful for the treatment of depressive disorders, among other conditions. The compounds exhibiting partial agonist activity at kappa receptors are useful for the treatment of bipolar disorder, e.g., as mood stabilizers, among other conditions. The compounds exhibiting full agonist activity at kappa receptors are useful for the treatment of the manic phase of bipolar disorder, among other conditions.

In a first aspect, the invention features a compound of formula I.

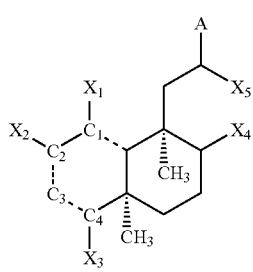

(I)

In formula I, A is selected from

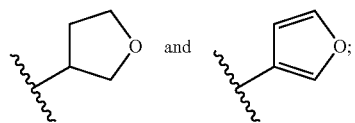

each of the bonds between $C_1$ and $C_6$, $C_2$ and $C_3$, and $C_3$ and $C_4$ is, independently, selected from a single bond or a double bond, provided that no carbon atom is part of more than one double bond; $X_1$ is selected from H, O, S, O—$R_1$, O-acyl, OC(O)$Z_1$, S—$R_1$, S-acyl, SC(O)$Z_1$, $NR_{14}R_{15}$, NH-acyl, NHC(O)NH-acyl, and NHC(O)$Z_1$; $X_2$ is selected from O—$R_2$, O-acyl, OC(O)$Z_2$, S—$R_2$, S-acyl, SC(O)$Z_2$, $NR_{16}R_{17}$, NH-acyl, NHC(O)NH-acyl, and NHC(O)$Z_2$; $X_3$ is selected from $CH_2$O—$R_3$, $CH_2$O-acyl, $CH_2$S—$R_3$, $CH_2$S-acyl, $CH_2$NH-acyl, $CH_2$NHC(O)NH-acyl, $CH_2$NHC(O)$Z_5$, $CH_2NR_{29}R_{30}$, NH-acyl, NHC(O)NH-acyl, $NR_{31}R_{32}$, NHC(O)$Z_5$, and C(O)—$Y_1$; $X_4$ is selected from C(O)—OR$_4$, $CH_2X_8$ and C(O)—$NR_5R_6$; $X_5$ is selected from H, O—$R_7$, O-acyl, NH-acyl, NHC(O)NH-acyl, and $NR_8R_9$, or $X_4$ and $X_5$ together are described by formula IIa or IIb to complete a six-membered ring

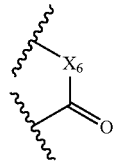

(IIa)

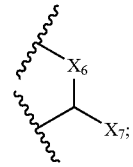

(IIb)

$X_6$ is selected from O, S, and $NR_{10}$; $X_7$ is selected from O—$R_{18}$, O-acyl, OC(O)$Z_3$, S—$R_{18}$, S-acyl, SC(O)$Z_3$, $NR_{19}R_{20}$, NH-acyl, NHC(O)NH-acyl, and NHC(O)$Z_3$; $X_8$ is selected from O—$R_{21}$, O-acyl, OC(O)$Z_4$, S—$R_{21}$, S-acyl, SC(O)$Z_4$, $NR_{22}R_{23}$, NH-acyl, NHC(O)NH-acyl, and NHC(O)$Z_4$; $Y_1$ is selected from OR$_{11}$, SR$_{11}$, and $NR_{12}R_{13}$; $Z_1$ is OR$_1$, SR$_1$, or $NR_{14}R_{15}$; $Z_2$ is OR$_2$, SR$_2$, or $NR_{16}R_{17}$; $Z_3$ is OR$_{18}$, SR$_{18}$, or $NR_{19}R_{20}$; $Z_4$ is OR$_{21}$, SR$_{21}$, or $NR_{22}R_{23}$; $Z_5$ is OR$_{24}$, SR$_{24}$, or $NR_{25}R_{26}$; and each of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{29}$, $R_{30}$, $R_{31}$, and $R_{32}$ is, independently, selected from H, $C_{1-8}$ alkyl, $C_{2-8}$ alkenyl, $C_{2-8}$ alkynyl, $C_{2-7}$ heterocyclyl, $C_{6-12}$ aryl, $C_{7-14}$ alkaryl, $C_{3-10}$ alkheterocyclyl, and $C_{1-8}$ heteroalkyl, or one or more of $R_5$ and $R_6$, $R_8$ and $R_9$, $R_{12}$ and $R_{13}$, $R_{14}$ and $R_{15}$, $R_{16}$ and $R_{17}$, $R_{19}$ and $R_{20}$, $R_{22}$ and $R_{23}$, $R_{25}$ and $R_{26}$, $R_{29}$ and $R_{30}$, and $R_{31}$ and $R_{32}$ combine to form a heterocyclic ring containing a nitrogen atom; with the proviso that the compound of formula I is not salvinorin A, B, C, D, E, or F; a $C_2$ ester of salvinorin A; a tetrahydrofuranylethyl salvinorin; a salvinorin benzoate; or a $C_1$ reduced salvinorin.

Compounds of formula I include those described by formulas IIIa and IIIb.

(IIIa)

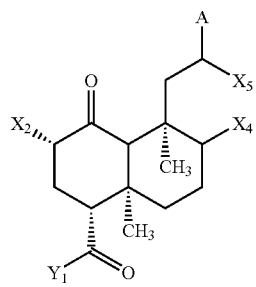

(IIIb)

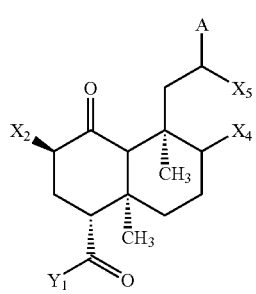

In formulas IIIa and IIIb, A, $X_2$, $X_4$, $X_5$, and $Y_1$ are as defined above.

Desirably, compounds of formulas IIIa and IIIb are further described by any one of formulas IVa or IVb.

(IVa)

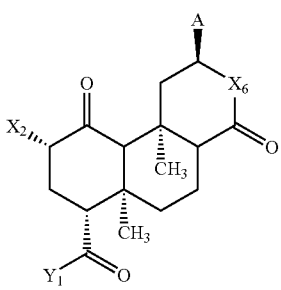

(IVb)

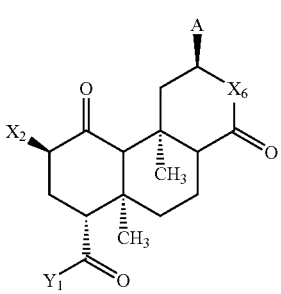

In formulas IVa and IVb, A, $X_2$, $X_6$, and $Y_1$ are as defined above.

Compounds of formula I further include those described by formulas Va and Vb.

(Va)

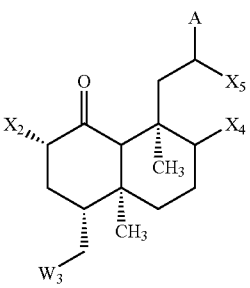

(Vb)

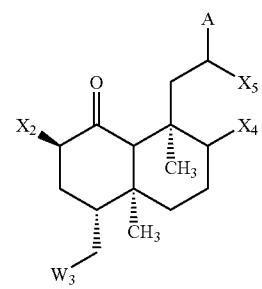

In formulas Va and Vb, $W_3$ is selected from O—$R_3$, O-acyl, S—$R_3$, S-acyl, NH-acyl, NHC(O)NH-acyl, NHC(O)$Z_5$, and $NR_{29}R_{30}$. A, $X_2$, $X_4$, $X_5$, $Z_5$, $R_3$, $R_{29}$, and $R_{30}$ are as defined above.

Desirably, compounds of formulas Va and Vb are further described by any one of formulas VIa or VIb.

(VIa)

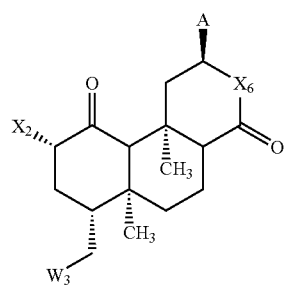

(VIb)

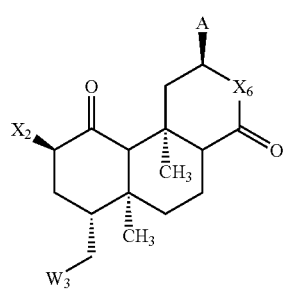

In formulas VIa and VIb, A, $X_2$, $X_6$, and $W_3$ are as defined above.

Compounds of formula I further include those described by formulas VIIa and VIIb.

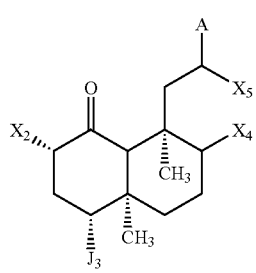
(VIIa)

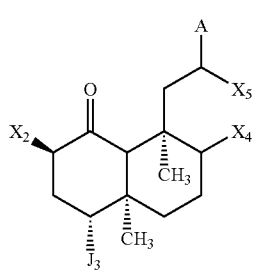
(VIIb)

In formulas VIIa and VIIb, $J_3$ is selected from NH-acyl, NHC(O)NH-acyl, $NR_{31}R_{32}$, $NHC(O)Z_5$. A, $X_2$, $X_4$, $X_5$, $Z_5$, $R_{31}$, and $R_{32}$ are as defined above.

Desirably, compounds of formulas VIIa and VIIb are further described by any one of formulas VIIc or VIId.

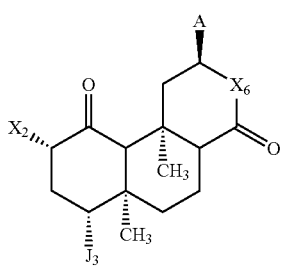
(VIIc)

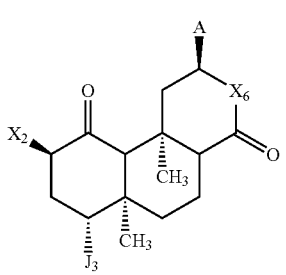
(VIId)

In formulas VIIc and VIId, A, $X_2$, $X_6$, and $J_3$ are as defined above.

Compounds of formula I also include those described by formulas VIIIa and VIIIb.

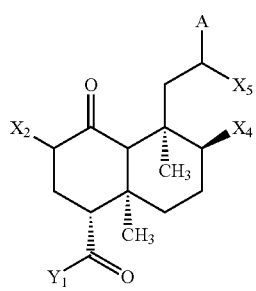
(VIIIa)

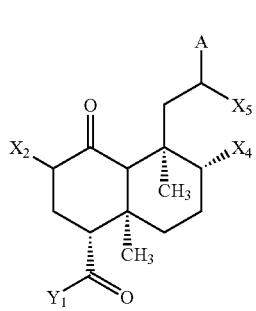
(VIIIb)

In formulas VIIIa and VIIIb, A, $X_2$, $X_4$, $X_5$, and $Y_1$ are as defined above.

Desirably, compounds of formulas VIIIa and VIIIb are further described by any one of formulas IXa or IXb.

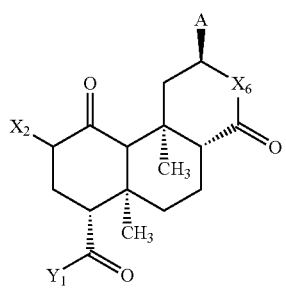
(IXa)

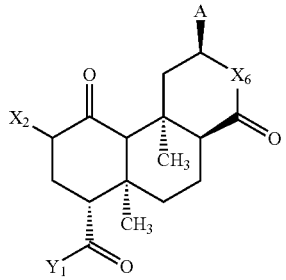
(IXb)

In formulas IXa and IXb, A, $X_2$, $X_6$, and $Y_1$ are as defined above.

Compounds of formula I include those described by formulas Xa and Xb.

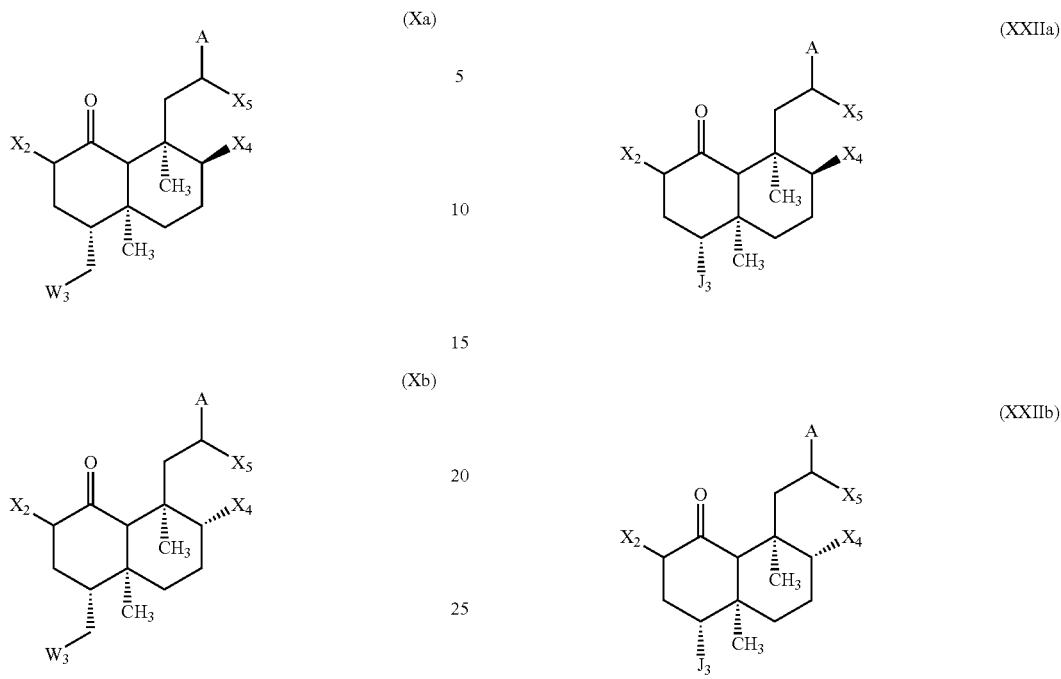

In formulas Xa and Xb, $W_3$ is selected from O—$R_3$, O-acyl, S—$R_3$, S-acyl, NH-acyl, NHC(O)NH-acyl, NHC(O)$Z_5$, and $NR_{29}R_{30}$. A, $X_2$, $X_4$, $X_5$, $Z_5$, $R_3$, $R_{29}$, and $R_{30}$ are as defined above.

Desirably, compounds of formulas Xa and Xb are further described by any one of formulas XIa or XIb.

In formulas XXIIa and XXIIb, $J_3$ is selected from NH-acyl, NHC(O)NH-acyl, $NR_{31}R_{32}$, NHC(O)$Z_5$. A, $X_2$, $X_4$, $X_5$, $Z_5$, $R_{31}$, and $R_{32}$ are as defined above.

Desirably, compounds of formulas XXIIa and XXIIb are further described by any one of formulas XXIIIa or XXIIIb.

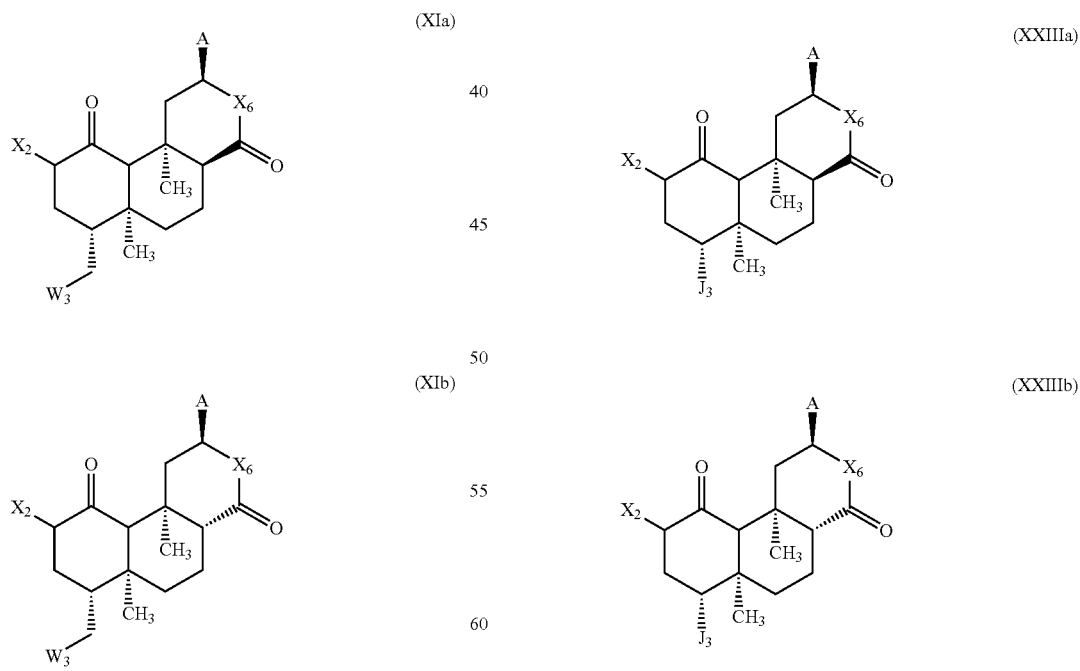

In formulas XIa and XIb, A, $X_2$, $X_6$, and $W_3$ are as defined above.

Compounds of formula I include those described by formulas XXIIa and XXIIb.

In formulas XXIIIa and XXIIIb, A, $X_2$, $X_6$, and $J_3$ are as defined above.

Compounds of formula I further include those described by formula XII.

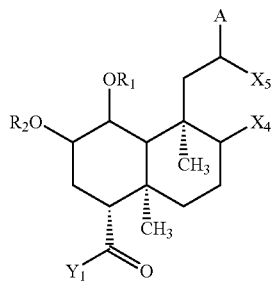
(XII)

In formula XII, A, $X_4$, $X_5$, $R_1$, $R_2$, and $Y_1$ are as defined above.

Desirably, compounds of formula XII are further described by any one of formulas XIIIa, XIIIb, XIIIc, or XIIId.

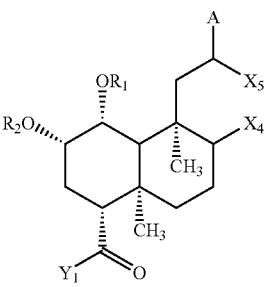
(XIIIa)

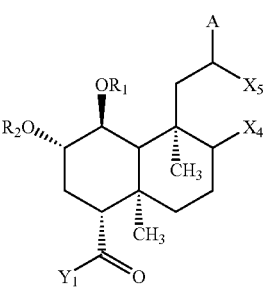
(XIIIb)

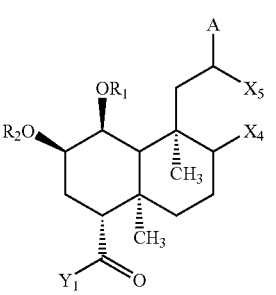
(XIIIc)

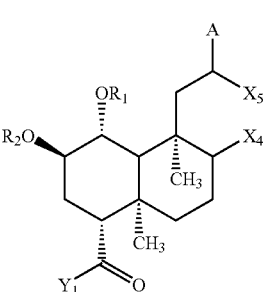
(XIIId)

In formulas XIIIa, XIIIb, XIIIc, and XIIId, A, $X_6$, $R_1$, $R_2$, and $Y_1$ are as defined above.

Compounds of formula I also include those described by formula XIV.

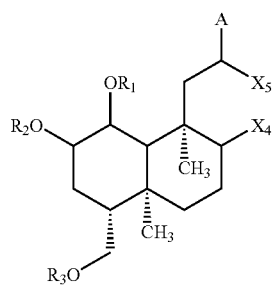
(XIV)

In formula XIV, A, $X_4$, $X_5$, $R_1$, $R_2$, and $R_3$ are as defined above.

Desirably, compounds of formula XIV are further described by any one of formulas XVa, XVb, XVc, or XVd.

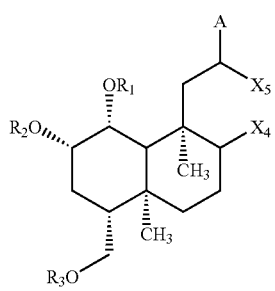
(XVa)

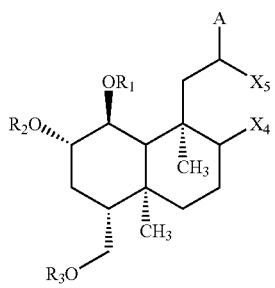
(XVb)

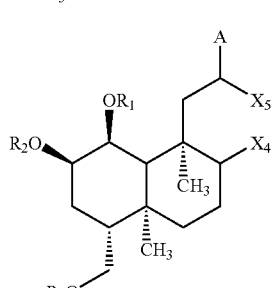
(XVc)

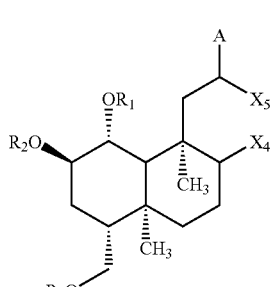
(XVd)

In formulas XVa, XVb, XVc, or XVd, A, $X_6$, $R_1$, $R_2$, and $R_3$ are as defined above.

Compounds of formula I include those described by formula XVI.

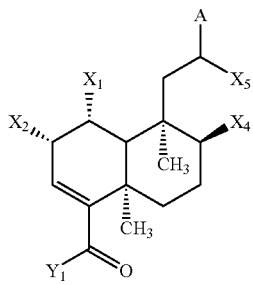

(XVI)

In formula XVI, A, $X_1$, $X_2$, $X_4$, $X_5$, and $Y_1$ are as defined above.

Desirably, compounds of formula XVI are further described by formula XVIIa.

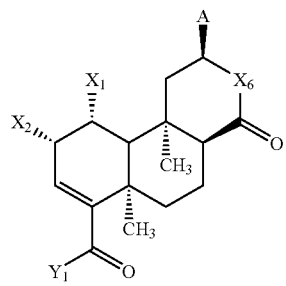

(XVIIa)

In formula XVIIa, A, $X_1$, $X_2$, $X_6$, and $Y_1$ are as defined above.

Compounds of formula I further include those described by formulas XVIIIa, XVIIIb, XVIIIc, or XVIIId.

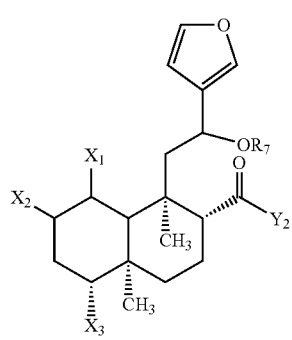

(XVIIIa)

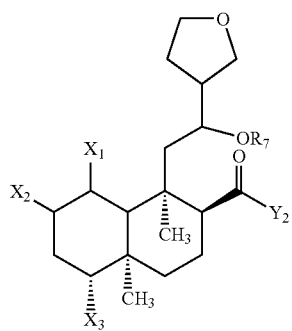

(XVIIIb)

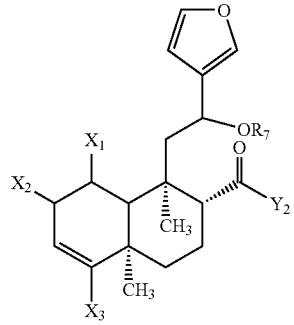

(XVIIIc)

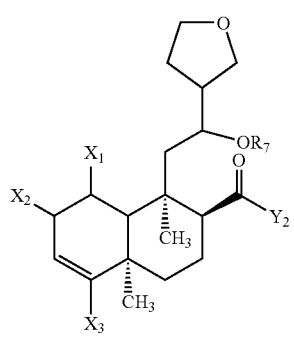

(XVIIId)

In formulas XVIIIa, XVIIIb, XVIIIc, and XVIIId, $Y_2$ is selected from $OR_4$ and $NR_5R_6$; and $X_1$, $X_2$, $X_3$, $R_4$, $R_5$, $R_6$, and $R_7$ are as defined above.

Compounds of formula I include those described by formula XX.

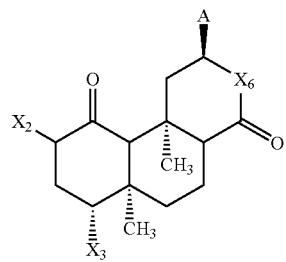

(XX)

In formula XX, $X_2$, $X_3$, $X_6$, and A are as defined above.

Desirably, compounds of formula XX are further described by any one of formulas XXIa-XXId.

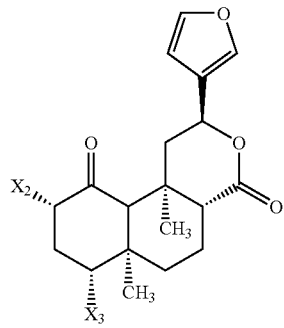

(XXIa)

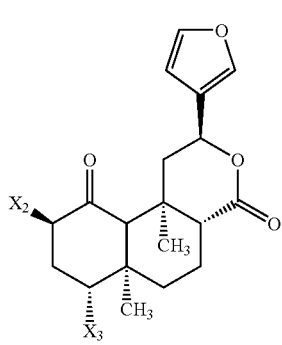

(XXIb)

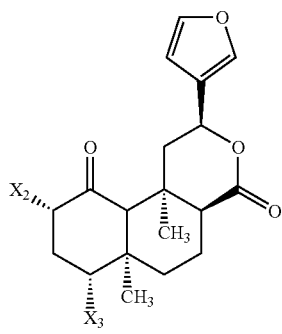

(XXIc)

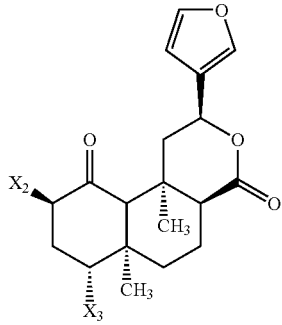

(XXId)

In formulas XXIa, XXIb, XXIc, and XXId, $X_2$ and $X_3$ are as defined above. Desirably, $X_2$ is selected from $NR_{16}R_{17}$, NH-acyl, NHC(O)NH-acyl, and NHC(O)$Z_2$ and $X_3$ is selected from $CH_2O$—$R_3$, $CH_2$O-acyl, $CH_2S$—$R_3$, $CH_2S$-acyl, $CH_2$NH-acyl, $CH_2$NHC(O)NH-acyl, $CH_2$NHC(O)$Z_5$, $CH_2NR_{29}R_{30}$, NH-acyl, NHC(O)NH-acyl, $NR_{31}R_{32}$, and NHC(O)$Z_5$, where $R_3$, $R_{16}$, $R_{17}$, $R_{29}$, $R_{30}$, $R_{31}$, $R_{32}$, $Z_2$, and $Z_5$ are defined as above.

The invention also features a substantially pure compound of formula XIX.

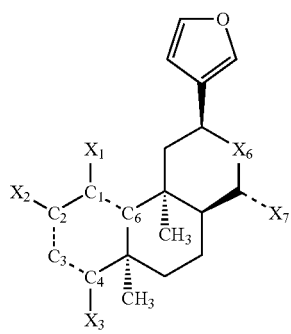

(XIX)

In formula XIX, each of the bonds between $C_1$ and $C_6$, $C_2$ and $C_3$, and $C_3$ and $C_4$ is, independently, selected from a single bond or a double bond, provided that no carbon atom is part of more than one double bond; $X_1$ is selected from H, O, S, O—$R_1$, O-acyl, OC(O)$Z_1$, S—$R_1$, S-acyl, SC(O)$Z_1$, $NR_{14}R_{15}$, NH-acyl, NHC(O)NH-acyl, and NHC(O)$Z_1$; $X_2$ is selected from H, O, S, O—$R_2$, O-acyl, OC(O)$Z_2$, S—$R_2$, S-acyl, SC(O)$Z_2$, $NR_{16}R_{17}$, NH-acyl, NHC(O)NH-acyl, and NHC(O)$Z_2$; $X_3$ is selected from $CH_2O$—$R_3$, $CH_2$O-acyl, $CH_2$NH-acyl, NHC(O)NH-acyl, and C(O)—$Y_1$; $X_6$ is selected from O, S, and $NR_{10}$; $X_7$ is selected from O, O—$R_{18}$, O-acyl, OC(O)$Z_3$, S—$R_{18}$, S-acyl, SC(O)$Z_3$, $NR_{19}R_{20}$, NH-acyl, NHC(O)NH-acyl, and NHC(O)$Z_3$; $Y_1$ is selected from $OR_{11}$ and $NR_{12}R_{13}$; $Z_1$ is $OR_1$, $SR_1$, or $NR_{14}R_{15}$; $Z_2$ is $OR_2$, $SR_2$, or $NR_{16}R_{17}$; $Z_3$ is $OR_{18}$, $SR_{18}$, or $NR_{19}R_{20}$; and each of $R_1$, $R_2$, $R_3$, $R_{10}$, $R_{11}$, $R_{12}$, $R_{13}$, $R_{14}$, $R_{15}$, $R_{16}$, $R_{17}$, $R_{18}$, $R_{19}$, and $R_{20}$ is, independently, selected from H, $C_{1-8}$ alkyl, $C_{2-8}$ alkenyl, $C_{2-8}$ alkynyl, $C_{2-7}$ heterocyclyl, $C_{6-12}$ aryl, $C_{7-14}$ alkaryl, $C_{3-10}$ alkheterocyclyl, and $C_{1-8}$ heteroalkyl, or one or more of $R_{12}$ and $R_{13}$, $R_{14}$ and $R_{15}$, $R_{16}$ and $R_{17}$, and $R_{19}$ and $R_{20}$, combine to form a heterocyclic ring containing a nitrogen atom; with the proviso that the compound of formula XIX is not 1,2-dihyroxy-episalvinorin. Desirably, the compound of formula XIX is selected from episalvinorin A, episalvinorin B, episalvinorin C, episalvinorin D, episalvinorin E, episalvinorin F, 1-hydroxy-2-acetyl-episalvinorin, 1-acetyl-2-hydroxy-episalvinorin, 1,2-diacetyl-episalvinorin, and 2-methoxymethyl-episalvinorin B.

Compounds of formula XIX include those described by formula XIXa.

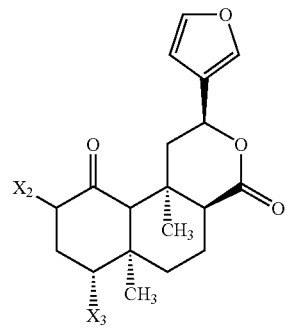

(XIXa)

In formulas XIXa, $X_2$ and $X_3$ are as defined above in formula XIX.

Any of the compounds described herein can be a selective kappa antagonist, a selective kappa receptor partial agonist, or a selective kappa agonist.

The invention features a method for treating a mood disorder in a mammal, e.g., a human patient, by administering an effective amount of a selective kappa receptor antagonist of formula I, salvinorin C, D, E, or F, a $C_2$ ester of salvinorin A, a tetrahydrofuranylethyl salvinorin, a salvinorin benzoate, or a $C_1$ reduced salvinorin. These compounds are particularly useful for treating depressive disorders and disorders associated with depression, such as major depression, dysthymia, bipolar disorder (manic depression), drug withdrawal, and post traumatic stress disorder; however, any psychologic or psychiatric disorder having symptoms that include abnormalities of mood, such as schizoaffective disorder, schizophrenia, anxiety disorder, panic disorder, post traumatic stress disorder, phobic disorder, borderline personality disorder, schizoid disorder, or schizotypal disorder, are amenable to treatment according to the present methods.

The invention features a method for treating bipolar disorder in a mammal, e.g., a human patient, in need thereof, by administering an effective amount of a selective kappa receptor partial agonist.

The invention further features a method for for stabilizing the mood of a mammal, e.g., a human patient, diagnosed with a mood disorder by administering an effective amount of a selective kappa receptor partial agonist.

The selective kappa receptor partial agonist can be a compound of formula I, salvinorin C, D, E, or F, a $C_2$ ester of salvinorin A, a tetrahydrofuranylethyl salvinorin, a salvinorin benzoate, or a $C_1$ reduced salvinorin. Desirably, the selective kappa receptor partial agonist is 2-(O-(N-methyl)formamide)-salvinorin B.

The invention features a method for treating mania in a mammal, e.g., a human patient, in need thereof, by administering an effective amount of a selective kappa receptor agonist. Selective kappa receptor agonists are particularly useful for treating mania associated with bipolar disorder, acute mania, and chronic mania. The mania can occur in a single episode or be recurring. The selective kappa receptor agonist can be a compound of formula I, salvinorin A, or salvinorin B, a $C_2$ ester of salvinorin A, a salvinorin benzoate, or a $C_1$ reduced salvinorin. Desirably, the selective kappa receptor agonist is 2-propionyl-salvinorin B, 2-butanoyl-salvinorin B, 2-methoxy-salvinorin B, episalvinorin B, 2-methoxymethyl-episalvinorin B, episalvinorin A, 2-methoxymethyl-salvinorin B, 2-(O-formamide)-salvinorin B, 2-n-butoxy-salvinorin B, 2-allyloxy-salvinorin B, 2-ethoxy-salvinorin B, 2-propoxy-salvinorin B, 2-benzyloxy-salvinorin B, 2-(N-ethylamino)-salvinorin, or 2-(N,N-dimethylamino)-salvinorin.

The selective kappa receptor antagonists, partial agonists, or agonists can be administered systemically, including, for example, by intravenous, intramuscular, or subcutaneous injection, orally, or by topical or transdermal application, provided that the kappa receptor antagonist is capable of penetrating the blood-brain barrier sufficiently to be effective. Alternatively, the kappa-selective compounds can be centrally administered using, for example, by an intrathecal, intracerebroventricular, or intraparenchemal injection.

The methods and compositions described herein can also be used to generate information useful, for example, for increasing investment in a company or increasing consumer demand for the methods and/or compositions.

The invention therefore features a method of increasing consumer demand for a pharmaceutical composition (e.g., the articles of the invention) or therapeutic regimen (e.g., the administration of articles of the invention) described herein. The method includes the step of disseminating information about the pharmaceutical composition or therapeutic regimen.

The invention further features a method of increasing investment in a company seeking governmental approval for the sale of a pharmaceutical composition and/or therapeutic regimen described herein. The method includes the steps of i) disseminating information about the pharmaceutical composition or therapeutic regimen and ii) disseminating information about the intent of the company to market the pharmaceutical composition or therapeutic regimen.

Consumer demand for a pharmaceutical composition described herein can be increased by disseminating information about the utility, efficacy, or safety of the pharmaceutical composition. Consumers include health maintenance organizations, hospitals, doctors, and patients. Typically, the information will be disseminated prior to a governmental approval for the sale of a composition or therapeutic regimen of the invention.

A company planning to sell a pharmaceutical composition described herein can increase investment therein by disseminating information about the company's intention to seek governmental approval for the sale of and disseminating information about the pharmaceutical composition and/or therapeutic regimen of the invention. For example, the company can increase investment by disseminating information about in vivo studies conducted, or planned, by the company, including, without limitation, information about the toxicity, efficacy, or dosing requirements of a pharmaceutical composition or therapeutic regimen of the invention. The company can also increase investment by disseminating information about the projected date of governmental approval of a pharmaceutical composition or therapeutic regimen of the invention.

Information can be disseminated in any of a variety of ways, including, without limitation, by press release, public presentation (e.g., an oral or poster presentation at a trade show or convention), on-line posting at a web site, and mailing. Information about the pharmaceutical composition or therapeutic regimen can include, without limitation, a structure, diagram, figure, chemical name, common name, tradename, formula, reference label, or any other identifier that conveys the identity of the pharmaceutical composition or therapeutic regimen of the invention to a person.

By "in vivo studies" is meant any study in which a pharmaceutical composition or therapeutic regimen of the invention is administered to a mammal, including, without limitation, non-clinical studies, e.g., to collect data concerning toxicity and efficacy, and clinical studies.

By "projected date of governmental approval" is meant any estimate of the date on which a company will receive approval from a governmental agency to sell, e.g., to patients, doctors, or hospitals, a pharmaceutical composition or therapeutic regimen of the invention. A governmental approval includes, for example, the approval of a drug application by the Food and Drug Administration, among others.

As used herein "substantially pure" refers to a composition containing a compound described herein which possesses the S configuration at C8 and which contains less than 10%, 5%, 2%, 1%, 0.05%, or 0.01% (w/w) of the corresponding epimer possessing the R configuration at C8 (e.g., greater than 90% episalvinorin A and less than 10% salvinorin A). The amount of R and S C8 isomers present in the mixture can be determined using chromatographic methods. The stereochemical configuration of each component in the mixture can be determined using NMR techniques.

By "selective kappa antagonist" is meant any chemical compound which has affinity for the kappa opioid receptor, substantially no agonist activity, and and produces less than 15% of the maximal response in comparison to dynorphin A. The selective kappa antagonist has more than 100, 200, 300, 500, 700, 1,000, or 2,000 fold greater affinity for kappa opioid receptors than for each of the mu and delta opioid receptors. Affinities for the various opioid receptor subtypes are determined using standard in vitro assays. For example, the binding assays may utilize guinea pig brain membranes or stably transfected Chinese Hamster Ovary (CHO) cells expressing each of the three opioid receptors.

By "selective kappa receptor partial agonist" is meant any chemical compound which has affinity for the kappa opioid receptor and agonist activity, but produces only a partial (i.e., submaximal) response of between 15% and 85% in comparison to dynorphin A, an endogenous neurotransmitter of the kappa opioid receptor. The selective kappa partial agonist has more than 100, 200, 300, 500, 700, 1,000, or 2,000 fold greater affinity for kappa opioid receptors than for each of the mu and delta opioid receptors. Affinities for the various opioid receptor subtypes are determined using standard in vitro assays. For example, the binding assays may utilize guinea pig brain membranes or stably transfected Chinese Hamster Ovary (CHO) cells expressing each of the three opioid receptors.

By "selective kappa receptor agonist" is meant any chemical compound which has affinity for the kappa opioid receptor and agonist activity, and produces at least 85% of the maximal response in comparison to dynorphin A, an endogenous neurotransmitter of the kappa opioid receptor. The selective kappa agonist has more than 100, 200, 300, 500, 700, 1,000, or 2,000 fold greater affinity for kappa opioid receptors than for each of the mu and delta opioid receptors. Affinities for the various opioid receptor subtypes are determined using standard in vitro assays. For example, the binding assays may utilize guinea pig brain membranes or stably transfected Chinese Hamster Ovary (CHO) cells expressing each of the three opioid receptors.

The term "administration" or "administering" refers to a method of giving a dosage of a pharmaceutical composition to a patient, where the method is, e.g., topical, transdermal, oral, intravenous, intraperitoneal, intracerebroventricular, intrathecal, or intramuscular. The preferred method of administration can vary depending on various factors, e.g., the components of the pharmaceutical composition, site of administration, and severity of the symptoms being treated.

By "depressive disorder" is meant any psychologic or psychiatric disorder which is associated with symptoms of depression. Treatable depressive disorders can be characterized by an inhibition or reduction of dopaminergic function in the nucleus accumbens, e.g., major depression, dysthymia, bipolar disorder (manic depression), drug withdrawal, and post-traumatic stress disorder.

By "effective amount" is meant is meant an amount of a compound of the invention which has a therapeutic effect, e.g., which prevents, reduces, or eliminates the depression, mania, mood fluctuations, or reduces CREB activation. This amount, an effective amount, can be routinely determined by one of skill in the art, by animal testing and/or clinical testing, and will vary, depending on several factors, such as the particular disorder to be treated and the particular compound of the invention used. This amount can further depend upon the subject's weight, sex, age and medical history.

By salvinorin A, B, C, D, E, and F is meant the compounds identified below.

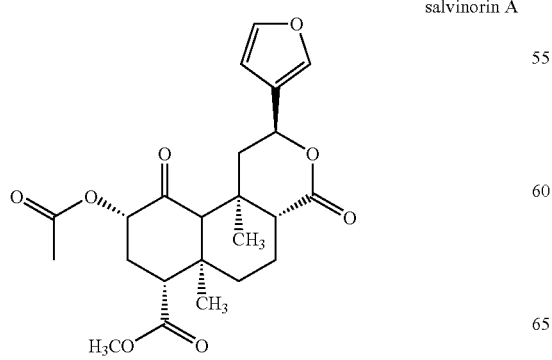

salvinorin A

-continued

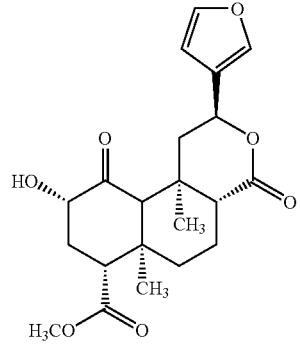

salvinorin B

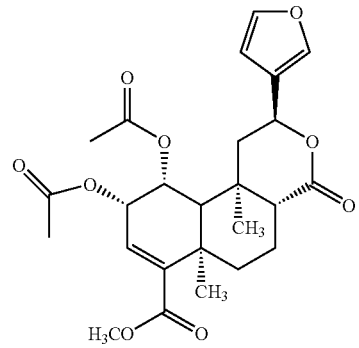

salvinorin C

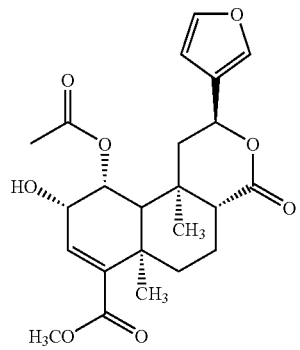

salvinorin D

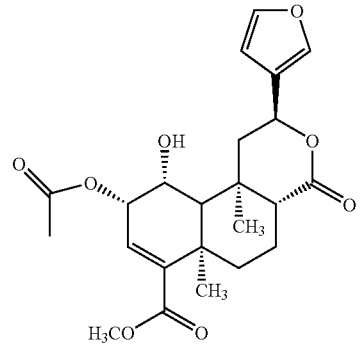

salvinorin E salvinorin F
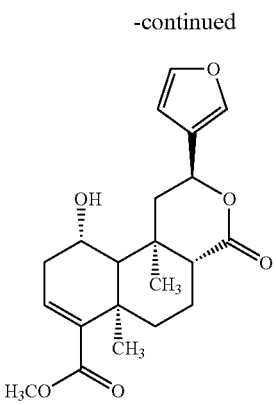
episalvinorin A
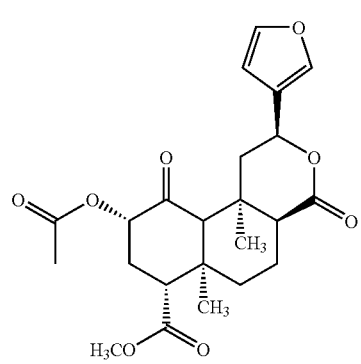
episalvinorin B
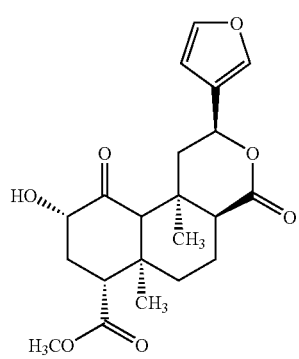
episalvinorin C
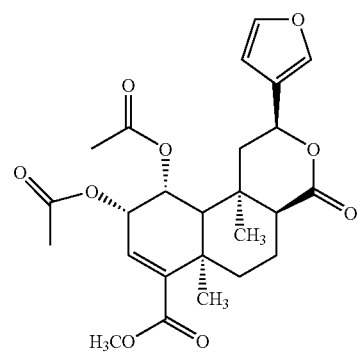
episalvinorin D
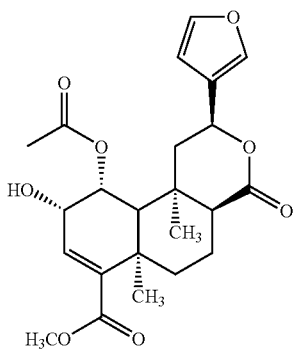
episalvinorin E
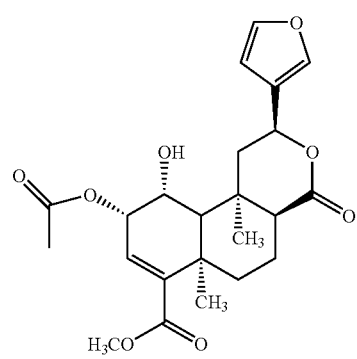
episalvinorin F
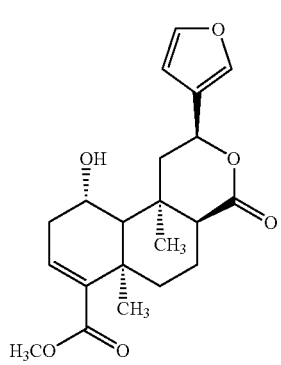
By "$C_2$ ester of salvinorin A" is meant a compound of formula A:
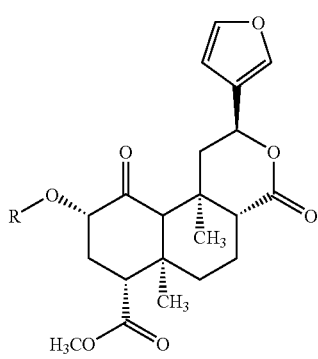
(A)
wherein R is a chemical moiety of formula R'—C(O)— in which R' is $C_{1-8}$ alkyl.

By "$C_1$ reduced salvinorin" is meant the reduced salvinorin compounds, shown below, including both C8 isomers.

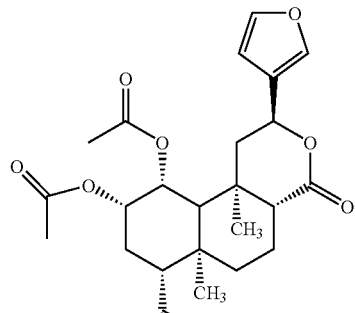
1,2-diacetyl-salvinorin

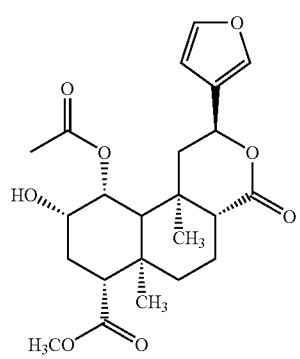
1-acetyl-2-hydroxy-salvinorin

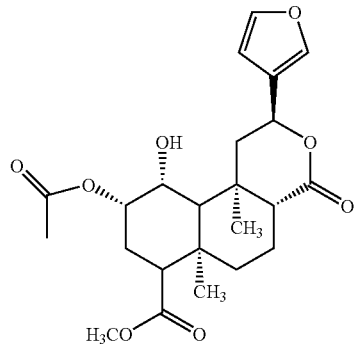
1-hydroxy-2-acetyl-salvinorin

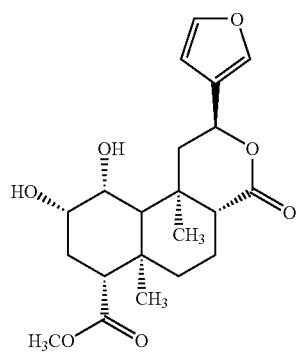
1,2-dihydroxy-salvinorin

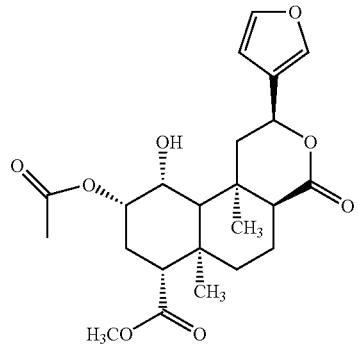
1-hydroxy-2-acetyl-episalvinorin

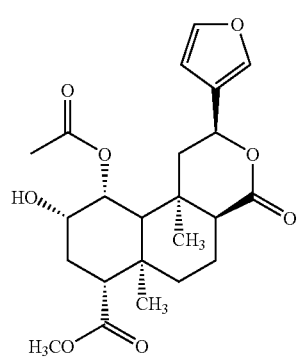
1-acetyl-2-hydroxy-episalvinorin

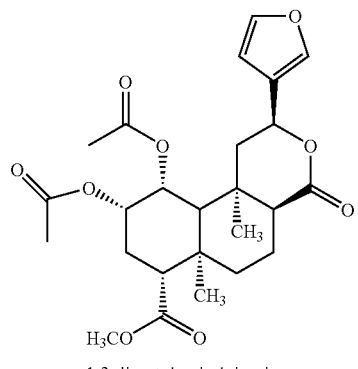
1,2-diacetyl-episalvinorin

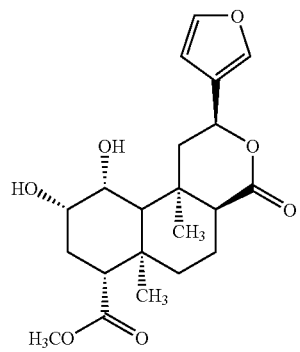
1,2-dihydroxy-episalvinorin

By "tetrahydrofuranylethyl salvinorin" is meant the furan reduced compounds, compounds a-e, shown below.

compound a

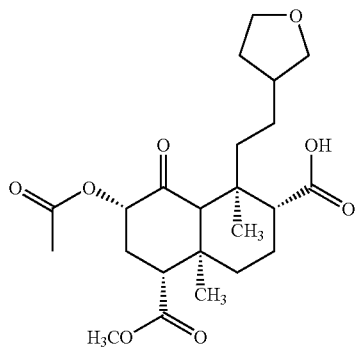

compound b

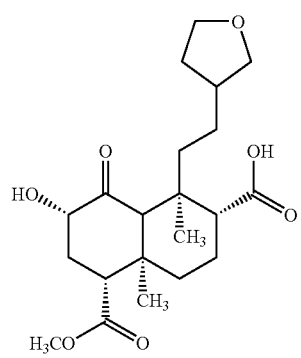

compound c

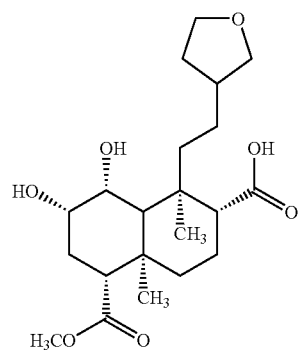

compound d

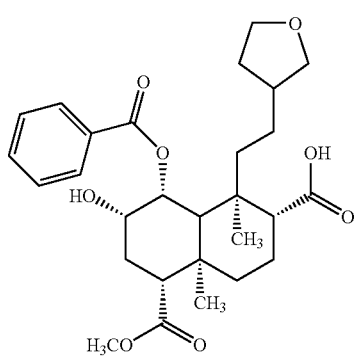

compound e

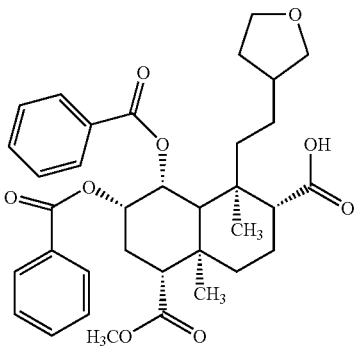

As used herein "salvinorin benzoate" refers to the benzoyl derivatives shown below.

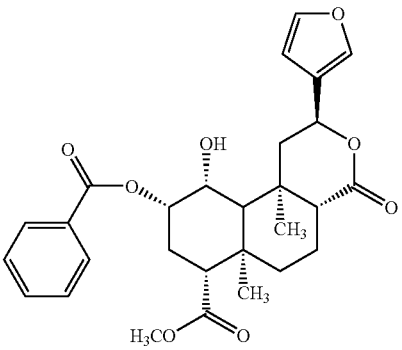

1-hydroxy-2-benzoyl-salvinorin

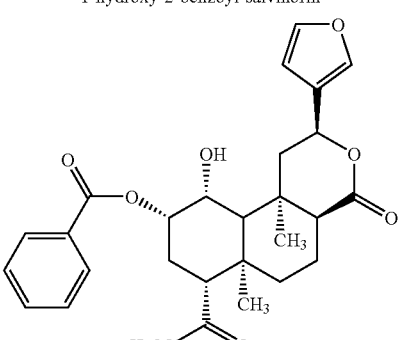

1-hydroxy-2-benzoyl-episalvinorin

In the generic descriptions of compounds of this invention, the number of atoms of a particular type in a substituent group is generally given as a range, e.g., an alkyl group containing from 1 to 7 carbon atoms or $C_{1-8}$ alkyl. Reference to such a range is intended to include specific references to groups having each of the integer number of atoms within the specified range. For example, an alkyl group from 1 to 8 carbon atoms includes each of $C_1$, $C_2$, $C_3$, $C_4$, $C_5$, $C_6$, $C_7$, and $C_8$. A $C_{1-8}$ heteroalkyl, for example, includes from 1 to 7 carbon atoms in addition to one or more heteroatoms. Other numbers of atoms and other types of atoms may be indicated in a similar manner.

As used herein, the terms "alkyl" and the prefix "alk-" are inclusive of both straight chain and branched chain groups and of cyclic groups, i.e., cycloalkyl. Cyclic groups can be monocyclic or polycyclic and preferably have from 3 to 6 ring carbon atoms, inclusive. Exemplary cyclic groups include cyclopropyl, cyclobutyl, cyclopentyl, and cyclohexyl groups. The $C_{1-8}$ alkyl group may be substituted or unsubstituted.

Exemplary substituents include alkoxy, aryloxy, sulfhydryl, alkylthio, arylthio, halide, hydroxyl, fluoroalkyl, perfluoralkyl, cyano, nitrilo, NH-acyl, amino, aminoalkyl, disubstituted amino, hydroxyalkyl, carboxyalkyl, and carboxyl groups. $C_{1-8}$ alkyls include, without limitation, methyl; ethyl; n-propyl; isopropyl; cyclopropyl; cyclopropylmethyl; cyclopropylethyl; n-butyl; iso-butyl; sec-butyl; tert-butyl; cyclobutyl; cyclobutylmethyl; cyclobutylethyl; n-pentyl; cyclopentyl; cyclopentylmethyl; cyclopentylethyl; 1-methylbutyl; 2-methylbutyl; 3-methylbutyl; 2,2-dimethylpropyl; 1-ethylpropyl; 1,1-dimethylpropyl; 1,2-dimethylpropyl; 1-methylpentyl; 2-methylpentyl; 3-methylpentyl; 4-methylpentyl; 1,1-dimethylbutyl; 1,2-dimethylbutyl; 1,3-dimethylbutyl; 2,2-dimethylbutyl; 2,3-dimethylbutyl; 3,3-dimethylbutyl; 1-ethylbutyl; 2-ethylbutyl; 1,1,2-trimethylpropyl; 1,2,2-trimethylpropyl; 1-ethyl-1-methylpropyl; 1-ethyl-2-methylpropyl; and cyclohexyl.

By "$C_{2-8}$ alkenyl" is meant a branched or unbranched hydrocarbon group containing one or more double bonds and having from 2 to 8 carbon atoms. A $C_{2-8}$ alkenyl may optionally include monocyclic or polycyclic rings, in which each ring desirably has from three to six members. The $C_{2-8}$ alkenyl group may be substituted or unsubstituted. Exemplary substituents include alkoxy, aryloxy, sulfhydryl, alkylthio, arylthio, halide, hydroxyl, fluoroalkyl, perfluoralkyl, cyano, nitrilo, NH-acyl, amino, aminoalkyl, disubstituted amino, quaternary amino, hydroxyalkyl, carboxyalkyl, and carboxyl groups. $C_{2-8}$ alkenyls include, without limitation, vinyl; allyl; 2-cyclopropyl-1-ethenyl; 1-propenyl; 1-butenyl; 2-butenyl; 3-butenyl; 2-methyl-1-propenyl; 2-methyl-2-propenyl; 1-pentenyl; 2-pentenyl; 3-pentenyl; 4-pentenyl; 3-methyl-1-butenyl; 3-methyl-2-butenyl; 3-methyl-3-butenyl; 2-methyl-1-butenyl; 2-methyl-2-butenyl; 2-methyl-3-butenyl; 2-ethyl-2-propenyl; 1-methyl-1-butenyl; 1-methyl-2-butenyl; 1-methyl-3-butenyl; 2-methyl-2-pentenyl; 3-methyl-2-pentenyl; 4-methyl-2-pentenyl; 2-methyl-3-pentenyl; 3-methyl-3-pentenyl; 4-methyl-3-pentenyl; 2-methyl-4-pentenyl; 3-methyl-4-pentenyl; 1,2-dimethyl-1-propenyl; 1,2-dimethyl-1-butenyl; 1,3-dimethyl-1-butenyl; 1,2-dimethyl-2-butenyl; 1,1-dimethyl-2-butenyl; 2,3-dimethyl-2-butenyl; 2,3-dimethyl-3-butenyl; 1,3-dimethyl-3-butenyl; 1,1-dimethyl-3-butenyl and 2,2-dimethyl-3-butenyl.

By "$C_{2-8}$ alkynyl" is meant a branched or unbranched hydrocarbon group containing one or more triple bonds and having from 2 to 8 carbon atoms. A $C_{2-8}$ alkynyl may optionally include monocyclic, bicyclic, or tricyclic rings, in which each ring desirably has five or six members. The $C_{2-8}$ alkynyl group may be substituted or unsubstituted. Exemplary substituents include alkoxy, aryloxy, sulfhydryl, alkylthio, arylthio, halide, hydroxy, fluoroalkyl, perfluoralkyl, cyano, nitrilo, NH-acyl, amino, aminoalkyl, disubstituted amino, quaternary amino, hydroxyalkyl, carboxyalkyl, and carboxyl groups. $C_{2-8}$ alkynyls include, without limitation, ethynyl, 1-propynyl, 2-propynyl, 1-butynyl, 2-butynyl, 3-butynyl; 1-pentynyl, 2-pentynyl, 3-pentynyl, 4-pentynyl, 5-hexene-1-ynyl, 2-hexynyl, 3-hexynyl, 4-hexynyl, 5-hexynyl; 1-methyl-2-propynyl; 1-methyl-2-butynyl; 1-methyl-3-butynyl; 2-methyl-3-butynyl; 1,2-dimethyl-3-butynyl; 2,2-dimethyl-3-butynyl; 1-methyl-2-pentynyl; 2-methyl-3-pentynyl; 1-methyl-4-pentynyl; 2-methyl-4-pentynyl; and 3-methyl-4-pentynyl.

By "$C_{2-7}$ heterocyclyl" is meant a stable 5- to 7-membered monocyclic or 7- to 14-membered bicyclic heterocyclic ring which is saturated partially unsaturated or unsaturated (aromatic), and which consists of 2 to 7 carbon atoms and 1, 2, 3 or 4 heteroatoms independently selected from the group consisting of N, O, and S and including any bicyclic group in which any of the above-defined heterocyclic rings is fused to a benzene ring. The heterocyclyl group may be substituted or unsubstituted. Exemplary substituents include alkoxy, aryloxy, sulfhydryl, alkylthio, arylthio, halide, hydroxy, fluoroalkyl, perfluoralkyl, cyano, nitrilo, NH-acyl, amino, aminoalkyl, disubstituted amino, quaternary amino, hydroxyalkyl, carboxyalkyl, and carboxyl groups. The nitrogen and sulfur heteroatoms may optionally be oxidized. The heterocyclic ring may be covalently attached via any heteroatom or carbon atom which results in a stable structure, e.g., an imidazolinyl ring may be linked at either of the ring-carbon atom positions or at the nitrogen atom. A nitrogen atom in the heterocycle may optionally be quaternized. Preferably when the total number of S and O atoms in the heterocycle exceeds 1, then these heteroatoms are not adjacent to one another. Heterocycles include, without limitation, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, without limitation, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl.

By "$C_{6-12}$ aryl" is meant an aromatic group having a ring system comprised of carbon atoms with conjugated π electrons (e.g., phenyl). The aryl group has from 6 to 12 carbon atoms. Aryl groups may optionally include monocyclic, bicyclic, or tricyclic rings, in which each ring desirably has five or six members. The aryl group may be substituted or unsubstituted. Exemplary subsituents include alkyl, hydroxy, alkoxy, aryloxy, sulfhydryl, alkylthio, arylthio, halide, fluoroalkyl, carboxyl, hydroxyalkyl, carboxyalkyl, amino, aminoalkyl, monosubstituted amino, disubstituted amino, and quaternary amino groups.

By "$C_{7-14}$ alkaryl" is meant an alkyl substituted by an aryl group (e.g., benzyl, phenethyl, or 3,4-dichlorophenethyl) having from 7 to 14 carbon atoms.

By "$C_{3-10}$ alkheterocyclyl" is meant an alkyl substituted heterocyclic group having from 7 to 14 carbon atoms in addition to one or more heteroatoms (e.g., 3-furanylmethyl, 2-furanylmethyl, 3-tetrahydrofuranylmethyl, or 2-tetrahydrofuranylmethyl).

By "$C_{1-8}$ heteroalkyl" is meant a branched or unbranched alkyl, alkenyl, or alkynyl group having from 1 to 8 carbon atoms in addition to 1,2, 3 or 4 heteroatoms independently selected from the group consisting of N, O, S, and P. Heteroalkyls include, without limitation, tertiary amines, secondary amines, ethers, thioethers, amides, thioamides, carbamates, thiocarbamates, hydrazones, imines, phosphodiesters, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted. Exemplary substituents include alkoxy, aryloxy, sulfhydryl, alkylthio, arylthio, halide, hydroxyl, fluoroalkyl, perfluoralkyl, cyano, nitrilo, NH-acyl, amino, aminoalkyl, disubstituted amino, quaternary amino, hydroxyalkyl, hydroxyalkyl, carboxyalkyl, and carboxyl groups. Examples of $C_{1-8}$ heteroalkyls include, without limitation, methoxymethyl and ethoxyethyl.

By "halide" is meant bromine, chlorine, iodine, or fluorine.

By "fluoroalkyl" is meant an alkyl group that is substituted with a fluorine.

By "perfluoroalkyl" is meant an alkyl group consisting of only carbon and fluorine atoms.

By "carboxyalkyl" is meant a chemical moiety with the formula —(R)—COOH, wherein R is selected from $C_{1-8}$ alkyl, $C_{2-8}$ alkenyl, $C_{2-8}$ alkynyl, $C_{2-7}$ heterocyclyl, $C_{6-12}$ aryl, $C_{7-14}$ alkaryl, $C_{3-10}$ alkheterocyclyl, or $C_{1-8}$ heteroalkyl.

By "hydroxyalkyl" is meant a chemical moiety with the formula —(R)—OH, wherein R is selected from $C_{1-8}$ alkyl, $C_{2-8}$ alkenyl, $C_{2-8}$ alkynyl, $C_{2-7}$ heterocyclyl, $C_{6-12}$ aryl, $C_{7-14}$ alkaryl, $C_{3-10}$ alkheterocyclyl, or $C_{1-8}$ heteroalkyl.

By "alkoxy" is meant a chemical substituent of the formula —OR, wherein R is selected from $C_{1-8}$ alkyl, $C_{2-8}$ alkenyl, $C_{2-8}$ alkynyl, $C_{2-7}$ heterocyclyl, $C_{6-12}$ aryl, $C_{7-14}$ alkaryl, $C_{3-10}$ alkheterocyclyl, or $C_{1-8}$ heteroalkyl.

By "aryloxy" is meant a chemical substituent of the formula —OR, wherein R is a $C_{6-12}$ aryl group.

By "alkylthio" is meant a chemical substituent of the formula —SR, wherein R is selected from $C_{1-8}$ alkyl, $C_{2-8}$ alkenyl, $C_{2-8}$ alkynyl, $C_{2-7}$ heterocyclyl, $C_{6-12}$ aryl, $C_{7-14}$ alkaryl, $C_{3-10}$ alkheterocyclyl, or $C_{1-8}$ heteroalkyl.

By "arylthio" is meant a chemical substituent of the formula —SR, wherein R is a $C_{6-12}$ aryl group.

By "quaternary amino" is meant a chemical substituent of the formula —(R)—N(R')(R'')(R''')$^+$, wherein R, R', R'', and R''' are each independently an alkyl, alkenyl, alkynyl, or aryl group. R may be an alkyl group linking the quaternary amino nitrogen atom, as a substituent, to another moiety. The nitrogen atom, N, is covalently attached to four carbon atoms of alkyl and/or aryl groups, resulting in a positive charge at the nitrogen atom.

By "acyl" is meant a chemical moiety with the formula R—C(O)—, wherein R is selected from $C_{1-8}$ alkyl, $C_{2-8}$ alkenyl, $C_{2-8}$ alkynyl, $C_{2-7}$ heterocyclyl, $C_{6-12}$ aryl, $C_{7-14}$ alkaryl, $C_{3-10}$ alkheterocyclyl, $C_{1-8}$ heteroalkyl (including amino acid acyls), or the acyl is a fatty acid acyl.

By "amino acid acyl" is meant a chemical moiety with the formula R—C(O)—, wherein R—C(O)— is selected from natural and unnatural amino acids.

By "fatty acid acyl" is meant a chemical moiety with the formula R—C(O)—, wherein R is a partially-saturated straight chain or branched hydrocarbon group having from 14 to 26 carbon atoms. Fatty acid acyls are derived from fatty acids including, without limitation, those occurring naturally in the brain. For example, fatty acids having 16 carbon atoms and 0, 1 or 2 double bonds (C16:0; C16:1 and C16:2), those with 18 carbon atoms and 1, 2 or 3 double bonds (C18:1; C18:2; and C18:3), those with 20 carbon atoms and 1, 2 or 4 double bonds (C20:1; C20:2; and C20:4) and those with 22 carbon atoms and 4, 5 or 6 double bonds (C22:4; C22:5 and C22:6). The fatty acids can be substituted or unsubstituted. Exemplary substituents include hydroxyl, halide, methyl, ethyl, propyl, isopropyl, butyl, and pentyl groups. Desirably, the fatty acid acyl is 4, 7, 10, 13, 16, 19 docosahexanoyl.

Because the compounds of the invention are highly selective for the kappa opioid receptor, they can be used in the methods of the invention to treat conditions for which kappa opioid receptor signaling plays a role in the pathogenesis of disease without directly influencing signaling at other receptors and producing unwanted side-effects.

Other features and advantages of the invention will be apparent from the following Detailed Description, the drawings, and the claims.

DETAILED DESCRIPTION

Figure 1:
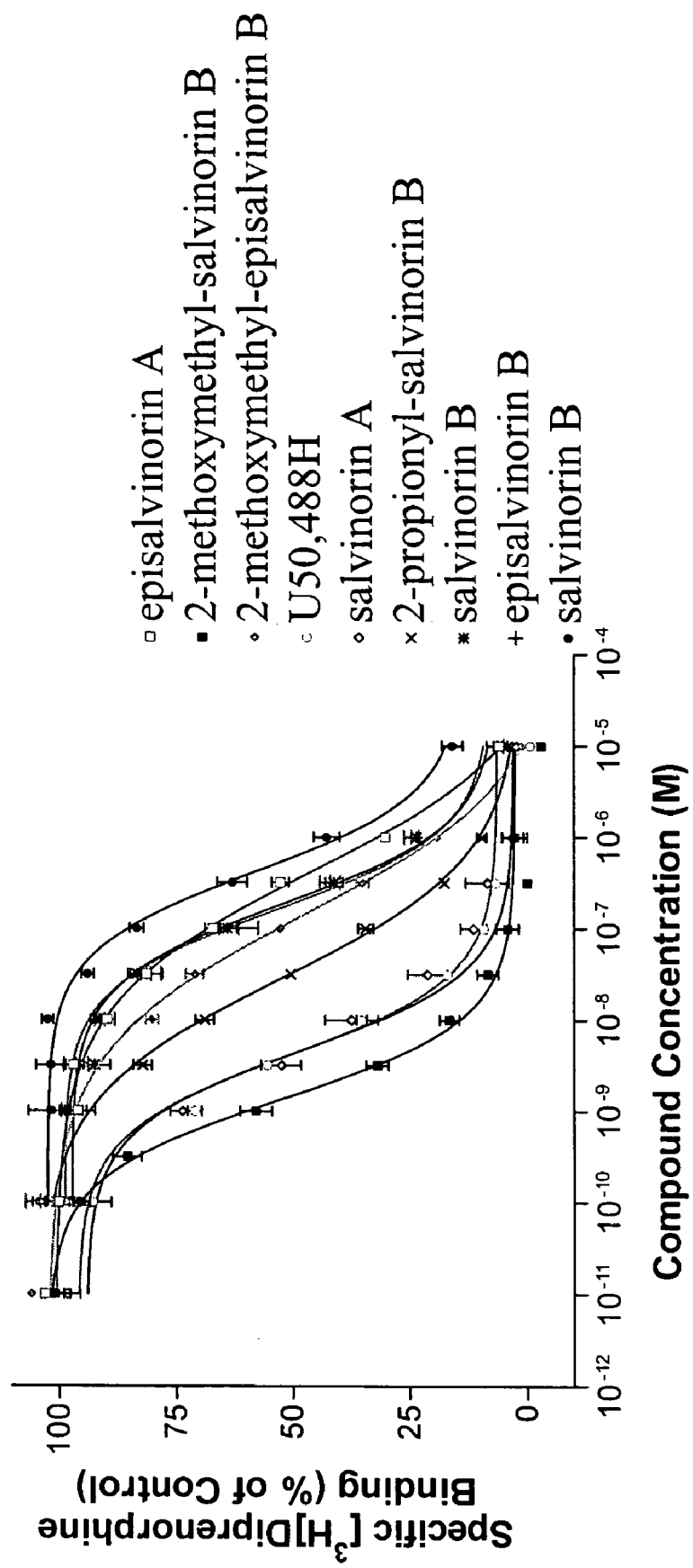
FIG. 1 is a graph showing the competitive inhibition of [$^3$H]Diprenorphine binding to human kappa opioid receptor in the presence of varying concentrations of test compound.
Figure 2:
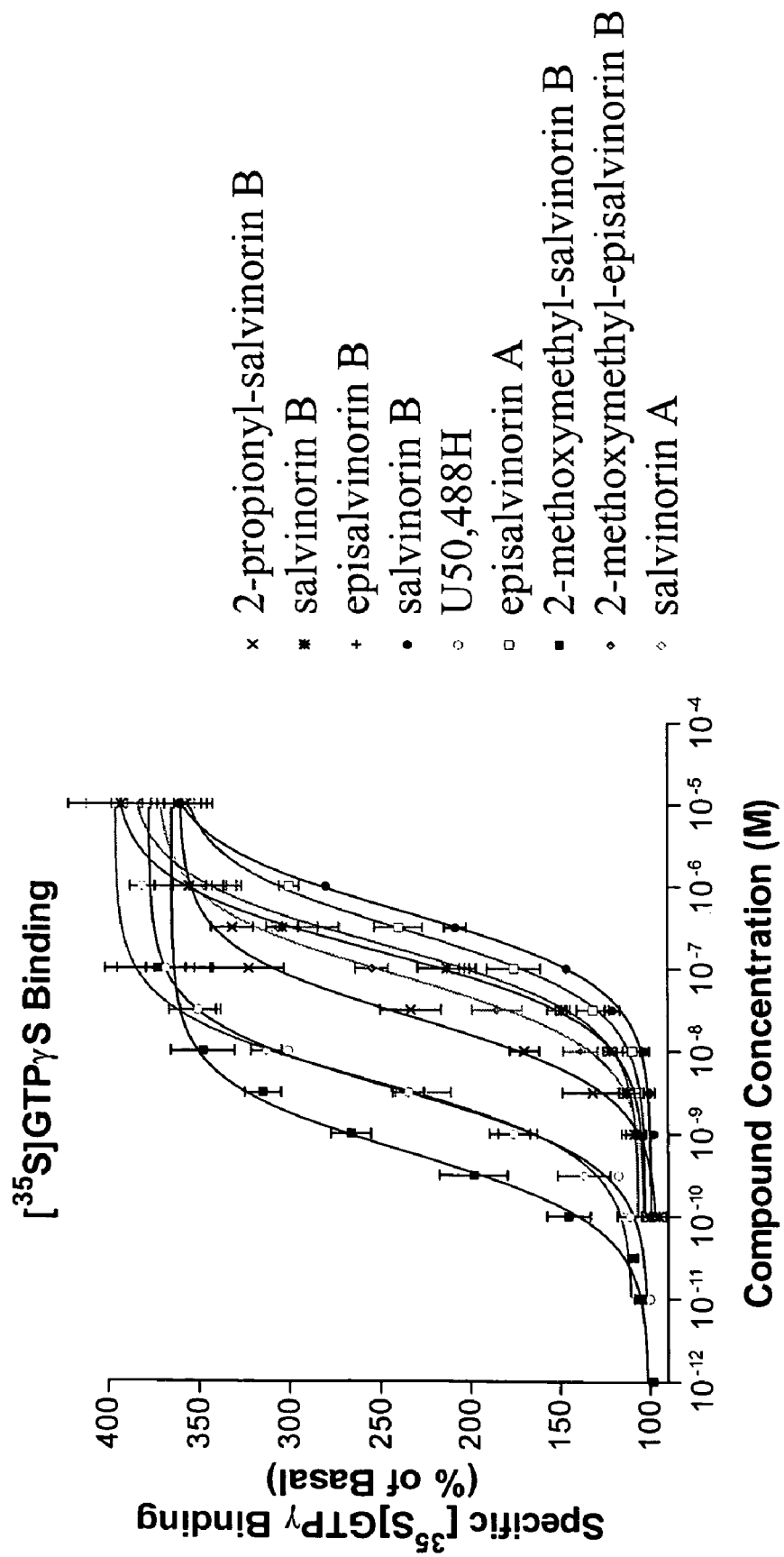
FIG. 2 is a graph showing the [$^{35}$S]GTPγS binding to human kappa opioid receptor in the presence of varying concentrations of test compound.

We have made compounds that are useful for the treatment of depression and/or mania. The compounds are described by formulas I-XXI. These compounds can be prepared as described in Examples 1-28.

Assays

To determine their affinity for specific opioid receptors, the compounds described herein can be characterized in radioligand receptor binding assays, using ligands that are specific for the mu, delta and kappa receptors. For example, the binding assays may utilize guinea pig brain membranes or stably transfected Chinese Hamster Ovary (CHO) cells expressing each of the three opioid receptors, as described in Example 29.

To determine their efficacy (e.g., agonist, partial agonist, antagonist) at a specific opioid receptor, compounds can be characterized by [$^{35}$S]GTPγS binding assay, as described in Example 30.

A symptom of clinical depression that can be modeled in rats is despair, a feeling of hopelessness. Symptoms of despair can be induced in rats using the forced swim test (FST), as described in Example 31, a highly validated model used to study antidepressant treatments.

Mania-like symptoms can be induced in rodents by the administration of psychomotor stimulant drugs such as cocaine or amphetamine. Psychostimulants produce a range of behaviors in animals that appear similar to mania, including hyperactivity, heightened sensory awareness and alertness, and changes in sleep patterns. Psychostimulant-induced hyperactivity is mediated by increased dopaminergic transmission in striatal regions. Based on this information, psychostimulant-induced hyperactivity in rodents has become a standard model for the screening of antimanic drugs. The mania-like effects of these psychomotor stimulants can be studied in behavioral assays that quantify locomotor activity ("open field activity") or the function of brain reward systems ("place conditioning" or "intracranial self-stimulation (ICSS)) (see Example 32). The Antimanic-like effects of salvinorin derivatives can be identified by the ability of these agents to reduce, attenuate, or block the stimulant or rewarding effects of cocaine or amphetamine in these assays. For further details see, for example, Einat and Belmaker Animal models of bipolar disorder: From a single episode to progressive cycling models; In: "Contemporary Issues in Modeling Psychopathology" Myslobodsky M, Weiner I (Eds.), 2000; London: Kluver Academic, New York, pp 165-179.

Therapy

The compounds described herein can be used for the treatment of mania, depressive disorders. Compounds of formula I can be particularly useful for treating major depression, dysthymia, bipolar disorder (manic depression), and post traumatic stress disorder; however, any psychologic or psychiatric disorder having symptoms that include abnormalities of mood or emotion are amenable to treatment according to the present methods. For example, the compounds can be used to treat disorders of mood, including, without limitation, Depression, Bipolar Disorder, Schizoaffective Disorder, Schizophrenia and other psychotic disorders, Anxiety Disorders, Panic Disorder, Traumatic Stress Disorders, Phobic Disorders, and Personality Disorders with abnormal mood, such as Borderline Personality Disorder, Schizoid and Schizotypal Disorders. For example, compounds having antagonist activity at kappa opioid receptors are useful for the treatment of depression; compounds having partial agonist activity at kappa opioid receptors are useful as mood stabilizers for the treatment of, for example, bipolar disorder; and compounds having agonist activity at kappa opioid receptors are useful for the treatment of mania.

The invention features a method of treating depressive disorders or mania by administering a compound having any of formulas I-XIX. The compounds of the invention may be administered with a pharmaceutically acceptable diluent, carrier, or excipient, in unit dosage form. Administration may be transdermal, parenteral, intravenous, intra-arterial, subcutaneous, intramuscular, intracranial, intraorbital, ophthalmic, intraventricular, intracapsular, intraspinal, intracisternal, intraperitoneal, intracerebroventricular, intrathecal, intranasal, aerosol, by suppositories, or oral administration.

Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" (20th ed., ed. A. R. Gennaro, 2000, Lippincott Williams & Wilkins). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycolate and deoxycholate, or may be oily solutions for administration in the form of nasal drops, or as a gel. The concentration of the compound in the formulation will vary depending upon a number of factors, including the dosage of the drug to be administered, and the route of administration.

The compound may be optionally administered as a pharmaceutically acceptable salt, such as a non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include calcium, zinc, iron, and the like.

Administration of compounds in controlled release formulations is useful where the compound of formula I has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose (LD50) to median effective dose (ED50)); (ii) a narrow absorption window in the gastro-intestinal tract; or (iii) a short biological half-life, so that frequent dosing during a day is required in order to sustain the plasma level at a therapeutic level.

Many strategies can be pursued to obtain controlled release in which the rate of release outweighs the rate of metabolism of the therapeutic compound. For example, controlled release can be obtained by the appropriate selection of formulation parameters and ingredients, including, e.g., appropriate controlled release compositions and coatings. Examples include single or multiple unit tablet or capsule compositions, oil solutions, suspensions, emulsions, microcapsules, microspheres, nanoparticles, patches, and liposomes.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

Pharmaceutical formulations of compounds of formulas I-XIX can include isomers such as diastereomers and enantiomers, mixtures of isomers, including racemic mixtures, salts, solvates, and polymorphs thereof.

The formulations can be administered to patients in therapeutically effective amounts. For example, an amount is administered which prevents, reduces, or eliminates the depression, mania, mood fluctuations, or reduces CREB activation, respectively. Typical dose ranges are from about 0.001 μg/kg to about 2 mg/kg of body weight per day. Desirably, a dose of between 0.001 μg/kg and 1 mg/kg of body weight, or 0.005 μg/kg and 0.5 mg/kg of body weight, is administered. The exemplary dosage of drug to be administered is likely to depend on such variables as the type and extent of the condition, the overall health status of the particular patient, the formulation of the compound, and its route of administration. Standard clinical trials may be used to optimize the dose and dosing frequency for any particular compound.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

Where the specification refers to a position of the salvinorin ring system, the position is identified according to the numbering system provided below.

numbering scheme

The synthesis of compounds of the invention may require selective protection and deprotection of alcohols, amines, and carboxylic acid functional groups in the salvinorin starting material. For example, commonly-used protecting groups for amines include carbamates, such as tert-butyl, benzyl, 2,2,2-trichloroethyl, 2-trimethylsilylethyl, 9-fluorenylmethyl, allyl, and m-nitrophenyl. Other commonly used protecting groups for amines include amides, such as formamides, acetamides, trifluoroacetamides, sulfonamides, trifluoromethanesulfonyl amides, trimethylsilylethanesulfonamides, and tert-butylsulfonyl amides. Examples of commonly used protecting groups for carboxylic acids include esters, such as methyl, ethyl, tert-butyl, 9-fluorenylmethyl, 2-(trimethylsilyl)ethoxy methyl, benzyl, diphenylmethyl, O-nitrobenzyl, ortho-esters, and halo-esters. Examples of commonly used protecting groups for alcohols include ethers, such as methyl, methoxymethyl, methoxyethoxymethyl, methylthiomethyl, benzyloxymethyl, tetrahydropyranyl, ethoxyethyl, benzyl, 2-napthylmethyl, O-nitrobenzyl, P-nitrobenzyl, P-methoxybenzyl, 9-phenylxanthyl, trityl (including methoxy-tritys), and silyl ethers. Protecting groups can be chosen such that selective conditions (e.g., acidic conditions, basic conditions, catalysis by a nucleophile, catalysis by a lewis acid, or hydrogenation) are required to remove each, exclusive of other protecting groups in a molecule. The conditions required for the addition of protecting groups to amine, alcohol, and carboxylic acid functionalities and the conditions required for their removal are provided in detail in "T. W. Green and P. G. M. Wuts: Protective Groups in Organic Synthesis" (2nd ed., 1991, John Wiley & Sons) and "P. J. Kocienski: Protecting Groups" (1994 Georg Thieme Verlag); each of which is incorporated herein by reference.

EXAMPLE 1

Modifications at C2

C2 modified salvinorin derivatives can be prepared, for example, from salvinorin B using the general procedures described below, among others. For example, the stereochemistry at C2 can be inverted using a Mitsunobu reaction (PPh$_3$+DIAD+NuH, where NuH is, for example, an arylalcohol, cyclic imide, or carboxylic acid, among others) (see Scheme 1A). Alternatively; the hydroxy group at C2 can be acylated using an acyl halide or a carboxylic acid and an activating agent (see Scheme 1B); can be alkylated using an alkyl halide (see Scheme 1C); can be converted to a carbamate (see Scheme 1D); or can be converted to an amine (see Scheme 1E). The amine of Scheme 1E can be converted to an amide (see Scheme 1F). These methods can also be used to make analogous modifications at C1, C12, C17, and C4, when these positions are substituted by hydroxyl groups.

Scheme 1A.
Nucleophilic Substitution at C(2).

Salvinorin B

General Protocol: To a CH$_2$Cl$_2$ solution of salvinorin B (1 equivalent), triphenylphosphine (3 equivalents), and the nucleophile (3 equivalents) was added diisopropylazodicarboxylate (3 equivalents) (DEAD may also be used) dropwise and the reaction was stirred at room temperature (3.5 hours). Saturated NaHCO$_3$ was added to the reaction mixture. The organic layer was washed with brine, dried (MgSO$_4$), and concentrated in vacuo. The crude material was purified by column chromatography (SiO$_2$; EtOAc-CH$_2$Cl$_2$) to obtain the desired product.

Scheme 1B.
Synthesis of C(2) esters.

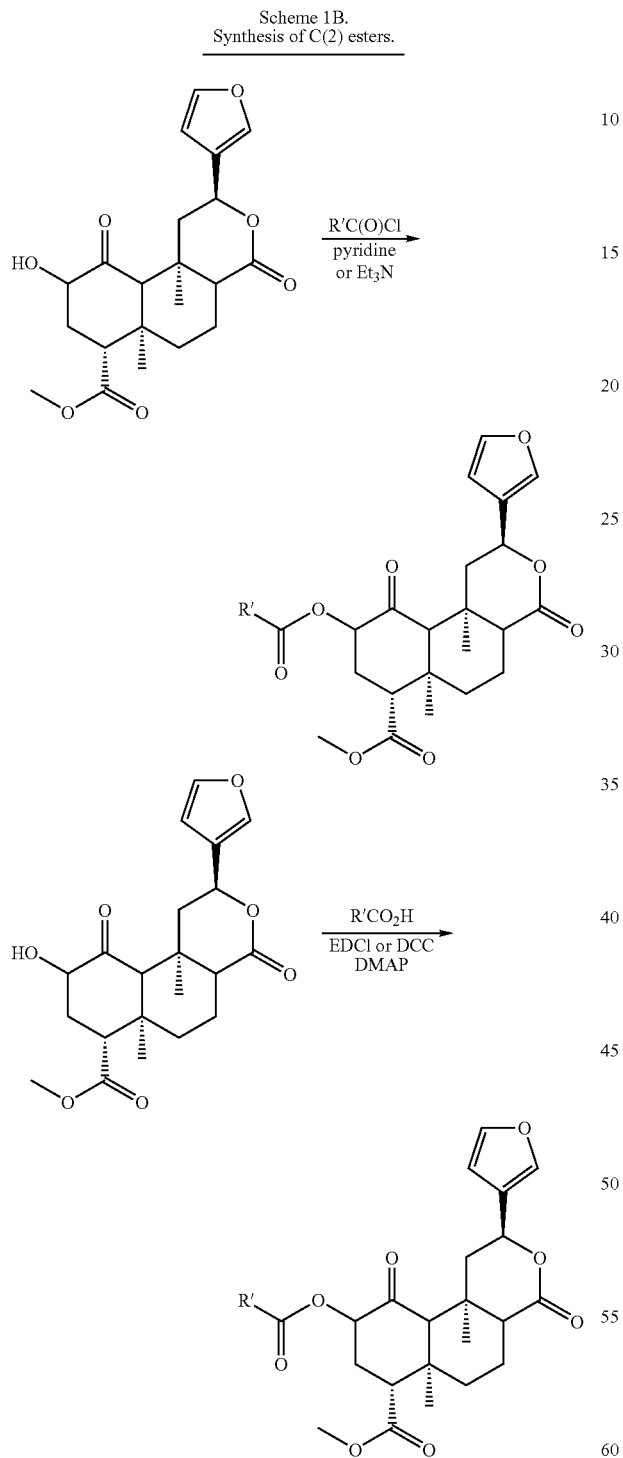

General Protocol: To a pyridine solution of salvinorin B (1 equivalent) was added the acyl chloride (5 equivalents) and the solution was stirred at room temperature (5 minutes). Ice cold water (2-5 mL) and CH$_2$Cl$_2$ (2-5 mL) were added to the reaction mixture. The organic layer was concentrated in vacuo and then purified by column chromatography (SiO$_2$; EtOAc-hexanes) to obtain the desired product.

Scheme 1C.
Synthesis of C(2) esthers.

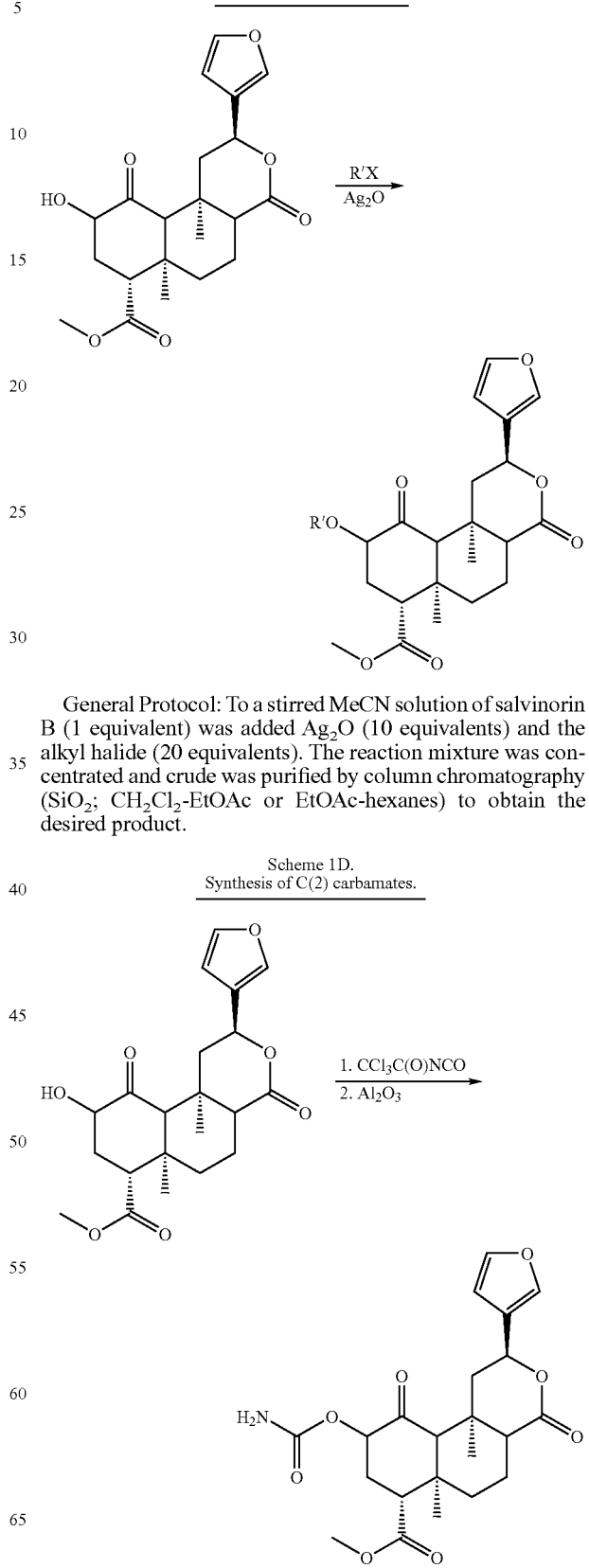

General Protocol: To a stirred MeCN solution of salvinorin B (1 equivalent) was added Ag$_2$O (10 equivalents) and the alkyl halide (20 equivalents). The reaction mixture was concentrated and crude was purified by column chromatography (SiO$_2$; CH$_2$Cl$_2$-EtOAc or EtOAc-hexanes) to obtain the desired product.

Scheme 1D.
Synthesis of C(2) carbamates.

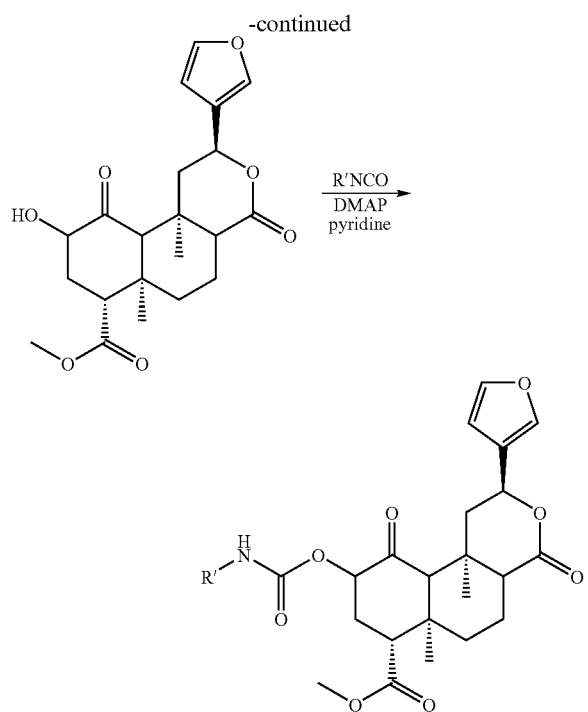

General Protocol: To a cloudy solution of salvinorin B (1 equivalent) and DMAP (catalytic amount) in pyridine was added the alkyl isocyanate (8-15 equivalents). The reaction mixture was stirred at room temperature (18 hours). The solution was concentrated in vacuo and the residue was purified by column chromatography (SiO$_2$; 1:2, EtOAc:hexanes) to obtain the desired product.

Scheme 1E.
Synthesis of C(2) amines.

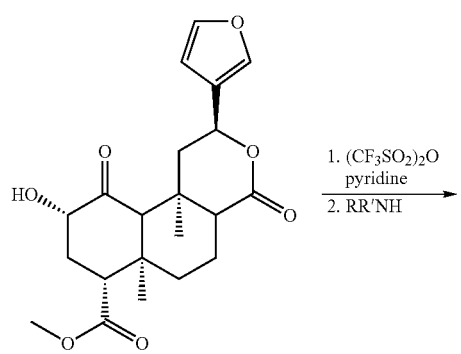

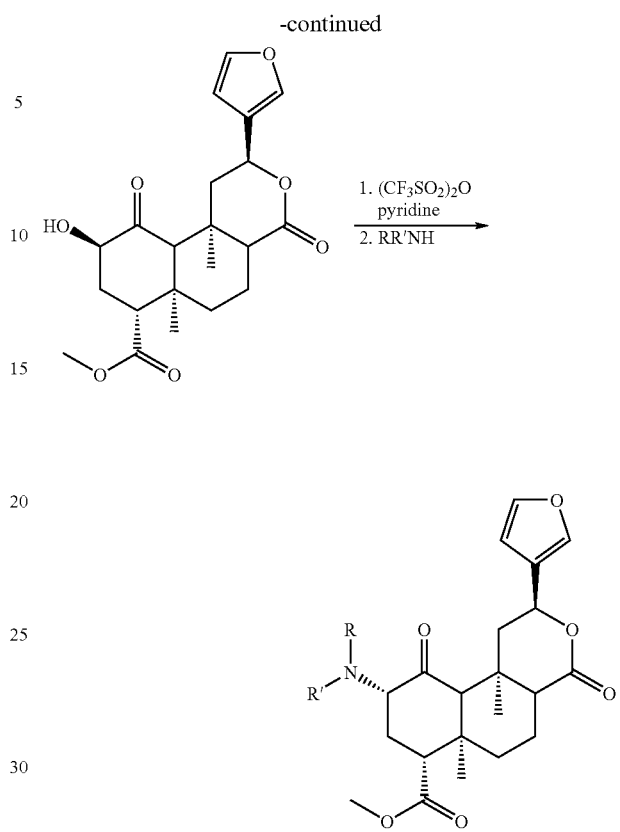

General Protocol: To a cold (0° C.) suspension of salvinorin B (1 equivalent) in CH$_2$Cl$_2$ was added pyridine (excess) and trifluoromethanesulfonic anhydride (excess) and the reaction solution was stirred at 0° C. for 20 minutes. The reaction solution was washed with 1 N HCl (2 mL), brine (2 mL), dried (MgSO$_4$) and evaporated. A solution of the triflate (1 equivalent) in amine (excess) was then stirred at a temperature of between 25° C. and 60° C. for a period of between 1.5 to 18 hours. In select cases CH$_2$Cl$_2$ was added. The solution was concentrated in vacuo and the residue was purified by column chromatography (SiO$_2$; 9:1, CH$_2$Cl$_2$:EtOAc) to obtain the desired product.

Scheme 1F.
Synthesis of C(2) amides.

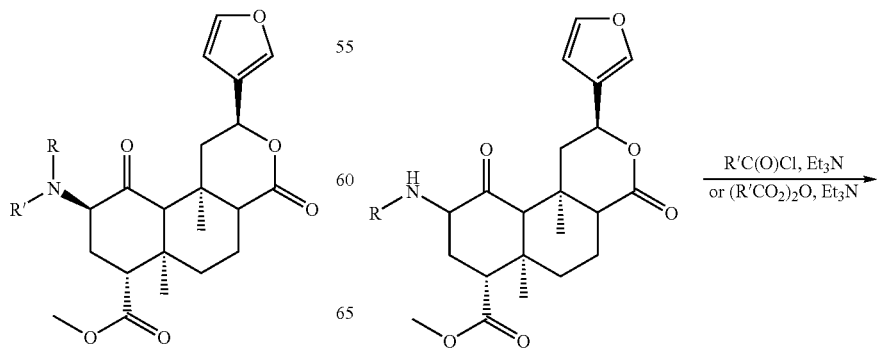

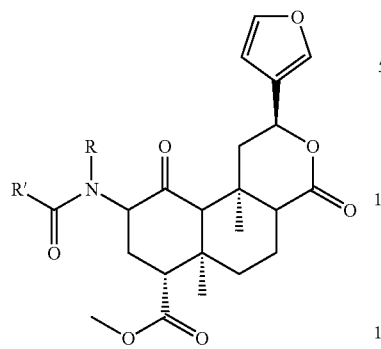

General Protocol: A CH$_2$Cl$_2$ solution of triethylamine (1.25 equivalent) and the acyl chloride or anhydride (1.25 equivalent) was added to the C(2) salvinorin amine (1 equivalent). The reaction solution was stirred at room temperature until completion. The reaction was concentrated and the residue was purified by column chromatography (SiO$_2$; 9:1, CH$_2$Cl$_2$:EtOAc) to obtain the desired product.

EXAMPLE 2

Modifications at C4

C4 modified salvinorin derivatives can be prepared, for example, from salvinorin A using the general procedures shown in Scheme 2, among others. First, the methoxy group is removed using LiI/pyridine. The resulting carboxylic acid group can be reduced to hydroxymethyl using borane, converted to an amide using an amine and an activating reagent, or converted to an ester using an alcohol and an activating reagent. The carboxylic acid can be activated, for example, by formation of an active ester, such as nitrophenylesters, N-hydroxysuccinimidyl esters, or others as described in *Chem. Soc. Rev.* 12:129, 1983 and *Angew. Chem. Int. Ed. Engl.* 17:569, 1978. The activated acid can then be reacted with a preselected amine or alcohol to produce the desired amide or ester, respectively. Analogous modification can be made at C17 carboxylic acid for compounds in which the lactone ring is opened (see Example 5).

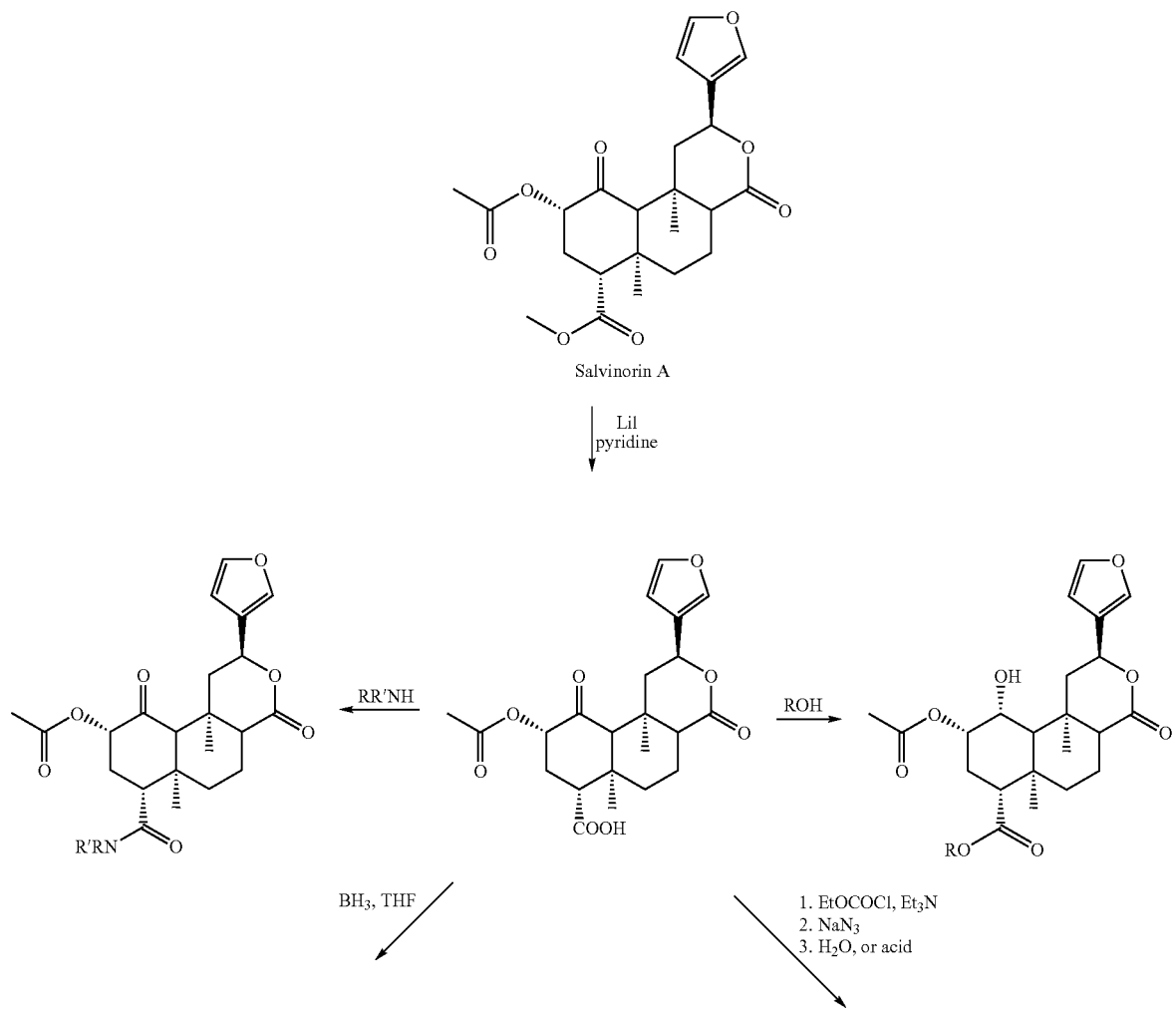

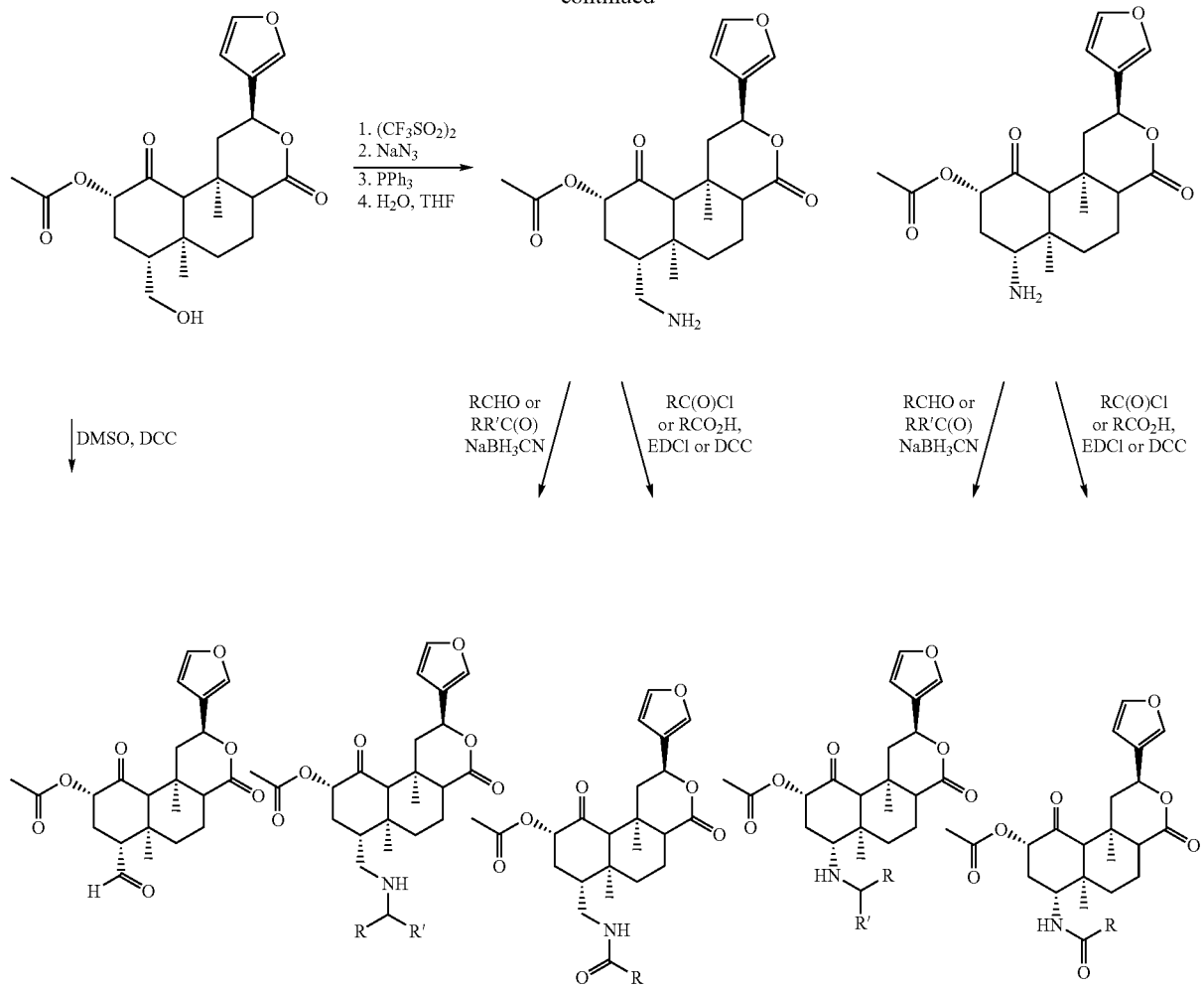

EXAMPLE 3

Hydrogenation of the Furan Ring

The furan ring can be hydrogenated using the general procedures shown in Scheme 3, among others. Using $H_2$/Pt/C the furan ring is hydrogenated without disruption of the lactone ring. When more stringent conditions, $H_2$/Pd/C, are employed, the reduction of the furan ring is accompanied by cleavage of the lactone ring and reduction of the C12 position. See Valdes et al., *J. Org. Chem.* 49:4716 (1984); and Koreeda et al., *Chem. Lett.* 2015 (1990).

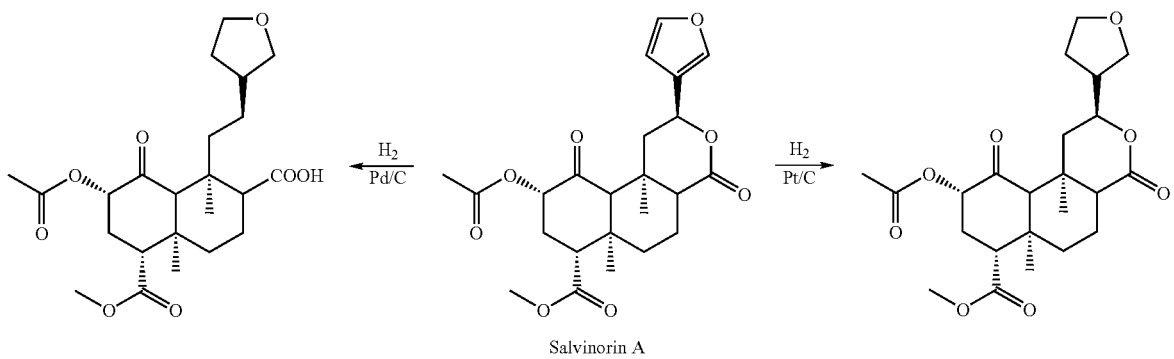

EXAMPLE 4

Reduction of the C(1)-Ketone Unit

The C1 ketone of salvinorin A can be reduced using the general procedure shown in Scheme 4, among others. See Valdes et al., *J. Org. Chem.* 49:4716 (1984); and Koreeda et al., *Chem. Lett.* 2015 (1990).

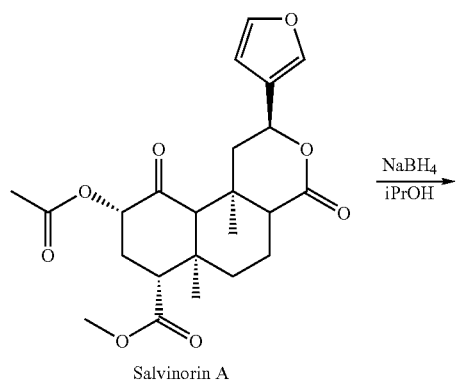

Salvinorin A

EXAMPLE 5

Opening of the Lactone Ring

The lactone ring of salvinorin derivatives can be opened using the general procedure shown in Scheme 5, among others.

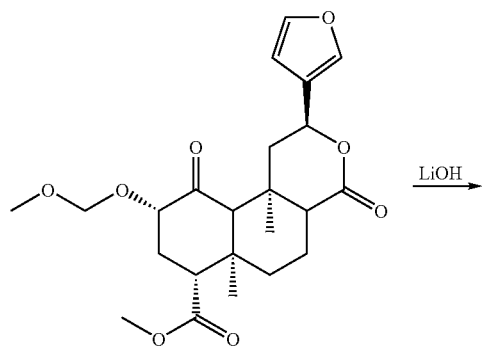

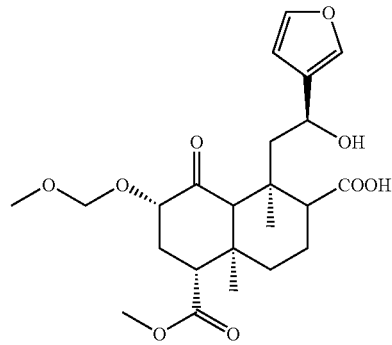

EXAMPLE 6

Epimerization at C8 (Conversion from 8R to 8S Isomer)

The C8 epimerization of salvinorin derivatives can be achieved under basic conditions as shown in Scheme 6 and reported, for 1,2-dihyroxy-episalvinorin, by Valdes et al., *J. Org. Chem.* 49:4716 (1984); and Valdes et al., *Org. Lett.* 3:3935 (2001).

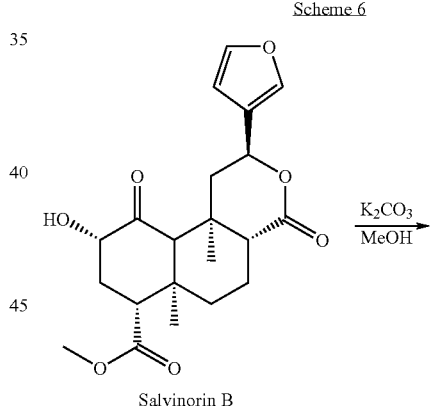

Salvinorin B

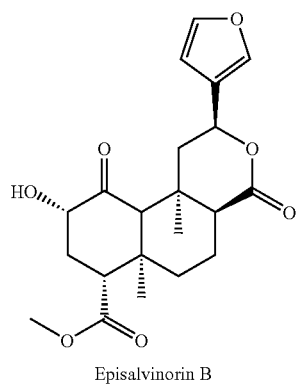

Episalvinorin B

EXAMPLE 7

Synthesis of Salvinorin B (Compound 1)

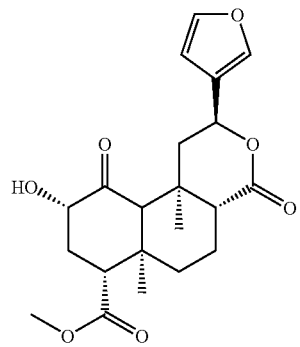

(1)

To a cold (0° C.) solution of salvinorin A (153.0 mg, 0.35 mmol) in MeOH (3 mL) and $CH_2Cl_2$ (3 mL) was added $K_2CO_3$ (98 mg, 0.71 mmol) and the mixture was stirred at 0° C. (20 minutes). Water (5 mL) and $CH_2Cl_2$ (5 mL) were added to the reaction mixture. The organic layer was concentrated in vacuo and then purified by column chromatography ($SiO_2$; 4:1, $CH_2Cl_2$:EtOAc) to obtain 66 mg (48%) of pure 1 as a white solid: $R_f$ 0.23 (1:1, EtOAc:hexanes); $^1$H NMR ($CDCl_3$) δ 1.10 (s, 3H), 1.49 (s, 3H), 1.51-1.69 (m, 3H), 1.77-1.82 (m, 1H), 2.02-2.10 (m, 2H), 2.14-2.20 (m, 1H), 2.17 (s, 1H), 2.45-2.50 (m, 1H), 2.55 (dd, 1H), 2.71 (dd, 1H), 3.60 (d, 1H), 3.72 (s, 3H), 4.05-4.12 (m, 1H), 5.57 (dd, 1H), 6.38 (s, 1H), 7.40-7.42 (m, 2H); $^{13}$C NMR ($CDCl_3$) 15.2, 16.5, 18.1, 34.5, 35.4, 38.1, 42.6, 43.5, 51.3, 51.9, 53.1, 63.8, 71.9, 74.3, 108.3, 125.3, 139.3, 143.8, 171.1, 171.8, 208.9 ppm.

EXAMPLE 8

Synthesis of 2-propionyl-salvinorin B (Compound 2)

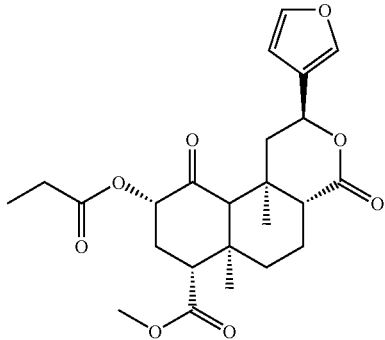

(2)

To a pyridine (400 μL) solution of salvinorin B (6.2 mg, 16 μmol) was added propionyl chloride (10 μL, 115 μmol) and the solution was stirred at room temperature (5 minutes). Ice cold water (2 mL) and $CH_2Cl_2$ (2 mL) were added to the reaction mixture. The organic layer was concentrated in vacuo and then purified by column chromatography ($SiO_2$; 1:2, EtOAc:hexanes) to obtain 4.3 mg (61%) of pure 2 as a white solid: $R_f$ 0.54 (1:1, EtOAc:hexanes); $^1$H NMR ($CDCl_3$) δ 1.11 (s, 3H), 1.18 (t, 3H), 1.45 (s, 3H), 1.52-1.67 (m, 4H), 1.77-1.82 (m, 1H), 2.06 (dd, 1H), 2.17 (s, 1H), 2.26-2.33 (m, 2H), 2.46 (q, 2H), 2.47-2.54 (m, 1H), 2.72-2.78 (m, 1H), 3.72 (s, 3H), 5.15 (dd, 1H), 5.51 (dd, 1H), 6.37 (d, 1H), 7.38-7.40 (m, 2H); $^{13}$C NMR ($CDCl_3$) 9.0, 15.2, 16.4, 18.2, 27.2, 30.8, 35.5, 38.2, 42.1, 43.4, 51.4, 51.9, 53.6, 64.1, 72.0, 74.8, 108.4, 125.3, 139.4, 143.7, 171.1, 171.6, 173.4, 202.0 ppm. HRMS (ES+) calcd for $C_{24}H_{31}O_8$ [M+H$^+$]: 447.2019, found: 447.2023.

EXAMPLE 9

Synthesis of 2-butyryl-salvinorin B (Compound 3)

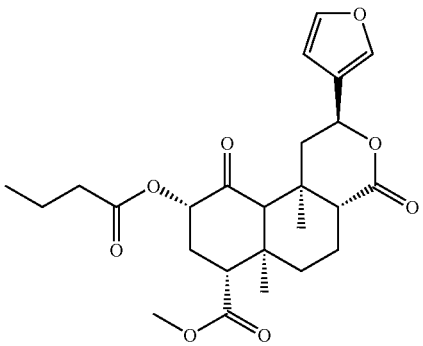

(3)

Compound 3 (2.7 mg, 36%) was prepared as a white solid from salvinorin B (6.3 mg, 16 mmol), pyridine (400 mL), and butyryl chloride (8 mL, 81 mmol) utilizing method A: $R_f$ 0.46 (1:1, EtOAc:hexanes); $^1$H NMR ($CDCl_3$) d 0.99 (t, J=7.2 Hz, 3H), 1.12 (s, 3H), 1.45 (s, 3H), 1.53-1.69 (m, 4H), 1.70 (q, J=7.2 Hz, 2H), 1.76-1.82 (m, 1H), 2.07 (dd, J=3.0, 11.4 Hz, 1H), 2.17 (s, 1H), 2.27-2.33 (m, 2H), 2.37-2.47 (m, 2H), 2.52 (dd, J=5.1, 13.5 Hz, 1H), 2.72-2.78 (m, 1H), 3.73 (s, 3H), 5.15 (dd, J=9.9, 9.9 Hz, 1H), 5.52 (dd, J=5.4, 11.7 Hz, 1H), 6.38 (dd, J=0.6, 1.8 Hz, 1H), 7.39-7.41 (m, 2H); $^{13}$C NMR ($CDCl_3$) 13.6, 15.2, 16.4, 18.2, 18.4, 30.9, 35.5, 35.8, 38.2, 42.1, 43.4, 51.4, 51.9, 53.7, 64.2, 72.0, 74.8, 108.4, 125.3, 139.5, 143.7, 171.1, 171.6, 172.6, 201.9 ppm; HRMS (ES+) calcd for C25H33O8 [M+H+]: 461.2175, found: 461.2179.

EXAMPLE 10

Synthesis of 2-methoxy-salvinorin B (Compound 4)

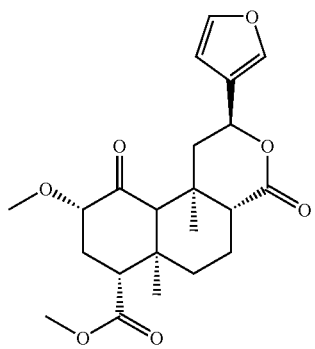

(4)

To a MeCN (800 μL) solution of salvinorin B (4.5 mg, 12 μmol) was added $Ag_2O$ (32 mg, 0.14 mmol) and MeI (17 μL, 0.27 mmol) and the mixture was stirred at 40° C. for 4 days. The reaction mixture was concentrated and the crude product was purified by column chromatography ($SiO_2$; 9:1, $CH_2Cl_2$:EtOAc) to obtain 3.6 mg (77%) of pure 4 as a white solid: $R_f$ 0.30 (9:1, $CH_2Cl_2$:EtOAc); $^1$H NMR ($CDCl_3$) δ 1.11 (s, 3H), 1.48 (s, 3H), 1.53-1.72 (m, 4H), 1.77-1.82 (m, 1H), 2.02-2.19 (m, 4H), 2.35-2.43 (m, 1H), 2.57 (dd, 1H), 2.66 (dd, 1H), 3.46 (s, 3H), 3.72 (s, 3H), 5.56 (dd, 1H), 6.38 (dd, 1H), 7.39-7.42 (m, 2H); $^{13}$C NMR ($CDCl_3$) 15.2, 16.4, 18.2, 32.0, 35.6, 38.3, 42.1, 43.7, 51.6, 51.8, 53.9, 58.1, 64.3, 72.0, 83.1, 108.3, 125.5, 139.3, 143.7, 171.1, 171.8, 206.2 ppm. HRMS (ES+) calcd for $C_{22}H_{29}O_7$ [M+H$^+$]: 405.1913, found: 405.1908.

EXAMPLE 11

Synthesis of Episalvinorin B (Compound 5)

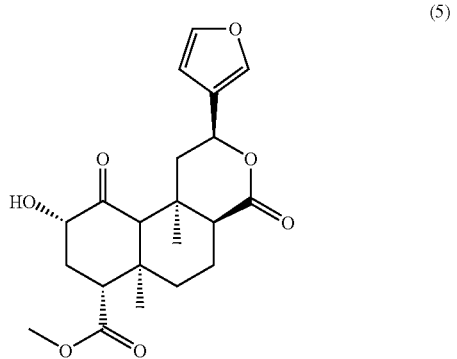

(5)

$K_2CO_3$ (200 mg) was added to a solution of salvinorin A (200 mg) in MeOH (25 mL) at room temperature. The mixture was stirred for 20 minutes. TLC (1:1, EtOAc: Hexanes) showed complete consumption of the starting material and a new lower $R_f$ spot. The reaction mixture was diluted with 50 mL of water and pH was adjusted to 7.0 followed by extraction with EtOAc (2×50 mL). The organic layer was dried ($Na_2SO_4$) and concentrated to afford a white solid. The white solid was further purified by column (1:1, EtOAc:Hexane) to give the pure compound 5 (Yield: 91 mg, 50.4%). $^1$H NMR: (300 MHz, $CDCl_3$) δ 7.44 (s, 1H), 7.41 (d, J=1.5 Hz, 1H), 6.37 (s, 1H), 5.31 (dd, J=4.5, 11.4 Hz, 1H), 4.01 (t, 1H), 3.69 (s, 3H), 3.60 (d, J=3.3 Hz, 1H), 2.72 (dd, J=3, 13.5 Hz, 1H), 2.47-2.38 (m, 3H), 2.23 (s, 1H), 2.18 (d, J=1.8 Hz, 1H), 2.07-1.82 (m, 3H), 1.64 (s, 3H), 1.56-41 (m, 2H), 1.06 (s, 3H). $^{13}$C NMR (70.5 MHz, $CDCl_3$): δ 209.2, 173.4, 172.1, 143.6, 139.6, 123.5, 108.4, 74.4, 70.0, 63.6, 52.3, 51.6, 48.2, 45.2, 42.6, 34.5, 34.2, 33.8, 24.6, 17.5, 15.3.

EXAMPLE 12

Synthesis of 2-methoxymethy-episalvinorin B (Compound 6)

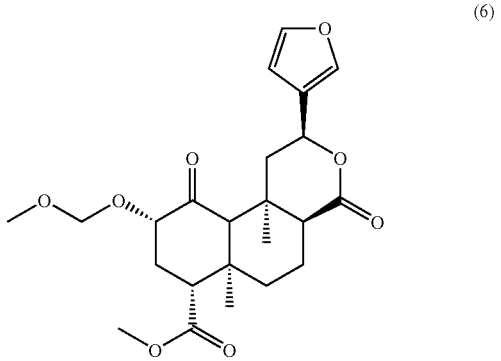

(6)

10 mg of compound 5 was dissolved in 5 mL of anhydrous $CH_2Cl_2$ to which was added a catalytic amount of DMAP (1 mg), N,N-Diisopropylethylamine (2 eq) and MOM-Cl (2 eq) at room temperature and the reaction was stirred for 48 hours. After completion of the reaction, water was added (10 mL) to the reaction mixture followed by extraction with EtOAc (2×10 mL). The organic layer was dried ($Na_2SO_4$) and concentrated to afford a crude mixture. The crude mixture was further purified by column chromatography (1:2, EtOAC: Hexanes) to give the pure compound 6. $^1$H NMR (300 MHz, $CDCl_3$): δ 7.41 (d, 2H), 6.38 (t, 1H), 5.30 (d, J=10.8 Hz, 1H), 4.697 (s, 2H), 4.06 (dd, J=7.2, 12.3 Hz, 1H), 3.69 (s, 3H), 3.37 (s, 3H), 2.68 (dd, J=3.3, 13.2 Hz, 1H), 2.46-2.31 (m, 3H), 2.24-2.11 (m, 3H), 2.02-1.82 (m, 2H), 1.65 (s, 3H), 1.59-1.41 (m, 3H), 1.26 (s, 3H). $^{13}$C NMR (70.5 MHz, $CDCl_3$): δ 206.0, 171.5, 172.2, 143.6, 139.5, 123.6, 108.4, 95.8, 78.2, 70.1, 64.3, 55.8, 53.1, 51.6, 48.3, 45.4, 42.0, 34.8, 34.0, 32.5, 24.6, 17.6, 15.3.

EXAMPLE 13

Synthesis of Episalvinorin A (Compound 7)

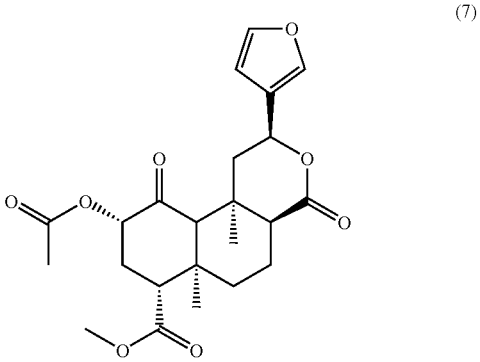

(7)

10 mg of compound 5 was dissolved in 5 mL of anhydrous $CH_2Cl_2$ to which was added catalytic amount of DMAP (1 mg), pyridine (2 eq) and acetic anhydride (2 eq) at room temperature and the reaction was stirred for 1 hour. After completion of the reaction, water was added (10 mL) to the reaction mixture followed by extraction with EtOAc (2×10 mL). The organic layer was dried ($Na_2SO_4$) and concentrated to afford a crude mixture. The crude mixture was further purified by column chromatography (1:2, EtOAC: Hexanes) to give the pure compound 7. Yield: quantitative. $^1$H NMR (300 MHz, $CDCl_3$): δ 7.43 (d, J=1.5 Hz, 1H), 7.38 (d, J=1.5 Hz, 1H), 6.37 (d, J=1.8 Hz, 1H), 5.26 (dd, J=1.8, 12 Hz), 5.11 (t, 1H), 3.70 (s, 3H), 2.75 (t, 1H), 2.46 (d, J=2.7 Hz, 1H), 2.39-2.14 (m, 7H), 2.06-1.89 (m, 1H), 1.63 (s, 3H), 1.57-1.46 (m, 2H), 1.26 (m, 1H), 1.07 (s, 3H). $^{13}$C NMR (70.5 MHz, $CDCl_3$): δ 202.3, 173.3, 171.8, 169.7, 143.5, 139.7, 123.4, 108.5, 75.2, 70.0, 64.0, 52.9, 51.7, 48.001, 45.2, 42.2, 34.7, 34.0, 30.7, 24.6, 20.5, 17.6, 15.2. The stereochemistry of 7 was confirmed by using H—H COSY, HMQC, and HMBC spectroscopies.

EXAMPLE 14

Synthesis of 2-methoxymethy-salvinorin B (Compound 8)

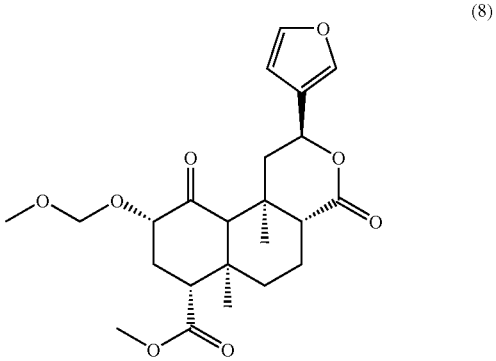

(8)

10 mg of compound 1 was dissolved in 5 mL of anhydrous $CH_2Cl_2$ to which was added a catalytic amount of DMAP (1 mg), N,N-Diisopropylethylamine (2 eq) and MOM-Cl (2 eq) at room temperature and the reaction was stirred for 48 hours. After completion of the reaction, water was added (10 mL) to the reaction mixture followed by extraction with EtOAc (2×10 mL). The organic layer was dried (Na$_2$SO$_4$) and concentrated to afford a crude mixture. The crude mixture was further purified by column chromatography (1:2, EtOAc: Hexane) to give the pure compound 8. $^1$H-NMR: (300 MHz, CDCl$_3$) δ 7.41 (d, 2H), 6.39 (d, J=0.6 Hz, 1H), 5.55 (dd, J=5.1, 11.7 Hz, 1H), 4.72 (q, 2H), 4.14 (dd, J=7.2, 12 Hz, 1H), 3.72 (s, 3H), 3.39 (s, 3H), 2.69 (dd, J=3.6, 13.5 Hz, 1H), 2.54 (dd, J=5.1, 13.2 Hz, 1H), 2.38-2.32 (m, 1H), 2.27-2.03 (m, 4H), 1.81-1.53 (m, 5H), 1.47 (s, 3H), 1.26 (s, 3H), 1.21 (s. 3H). $^{13}$C-NMR: (70.5 MHz, CDCl$_3$) δ 205.8, 171.8, 171.2, 143.7, 139.4, 125.3, 108.3, 95.7, 77.8, 71.9, 64.3, 55.8, 53.9, 51.9, 51.5, 43.6, 41.9, 38.2, 35.5, 32.6, 18.1, 16.4, 15.2.

EXAMPLE 15

Synthesis of 2-(O-formamide)-salvinorin B (Compound 9)

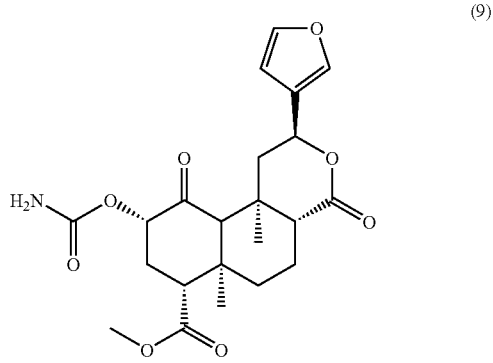

(9)

To a cloudy solution of salvinorin B (17.4 mg, 45 μmol) in CH$_2$Cl$_2$ (2 mL) was added trichloroacetylisocyanate (20 μL, 0.17 mmol) and the solution was stirred at room temperature (10 minutes) under argon. Al$_2$O$_3$ (activated, 450 mg) was added and the mixture was stirred at room temperature (3 hours). The reaction mixture was concentrated to ~0.5 mL and then purified by column chromatography (SiO$_2$; 1:1, EtOAc:hexanes) to obtain 17.6 mg (91%) of pure 9 as a white solid: R$_f$ 0.15 (1:1, EtOAc:hexanes); $^1$H NMR (CDCl$_3$) δ 1.12 (s, 3H), 1.46 (s, 3H), 1.53-1.72 (m, 3H), 1.77-1.82 (m, 1H), 2.04-2.09 (m, 1H), 2.14-2.40 (m, 3H), 2.16 (s, 1H), 2.54 (dd, J=5.1, 13.2 Hz, 1H), 2.74 (dd, J=3.3, 13.2 Hz, 1H), 3.73 (s, 3H), 4.78 (br s, 2H), 5.08 (dd, J=7.5, 12.3 Hz, 1H), 5.53 (dd, J=5.1, 11.7 Hz, 1H), 6.38 (s, 1H), 7.38-7.41 (m, 2H); $^{13}$C NMR (CDCl$_3$) 15.2, 16.4, 18.2, 31.0, 35.5, 38.2, 42.1, 43.4, 51.4, 51.9, 53.6, 64.1, 72.0, 75.5, 108.4, 125.3, 139.4, 143.7, 155.3, 171.1, 171.6, 203.0 ppm.

EXAMPLE 16

Synthesis of 2-(O-(N-methyl)formamide)-salvinorin B (Compound 10)

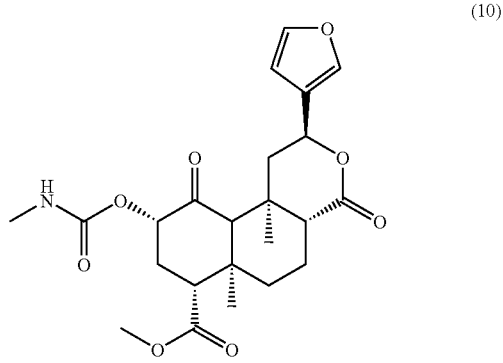

(10)

Compound 10 (11.0 mg, 68%) was prepared as a white solid from salvinorin B (14.1 mg, 36 μmol), DMAP (catalytic amount), pyridine (700 μL), and methyl isocyanate (32 μL, 540 μmol) utilizing the method of Scheme 1D. R$_f$ 0.10 (1:2, EtOAc:hexanes); $^1$H NMR (CDCl$_3$) δ 1.11 (s, 3H), 1.46 (s, 3H), 1.54-1.72 (m, 3H), 1.77-1.81 (m, 1H), 2.05-2.10 (m, 1H), 2.15-2.37 (m, 3H), 2.18 (s, 1H), 2.55 (dd, J=5.1, 13.5 Hz, 1H), 2.75 (dd, J=3.6, 13.2 Hz, 1H), 2.83 (d, J=4.8 Hz, 3H), 3.73 (s, 3H), 4.83-4.84 (m, 1H), 5.10 (dd, J=7.5, 12.0 Hz, 1H), 5.53 (dd, J=5.1, 11.7 Hz, 1H), 6.38 (s, 1H), 7.39-7.41 (m, 2H); $^{13}$C NMR (CDCl$_3$) 15.2, 16.4, 18.1, 27.7, 31.1, 35.4, 38.2, 42.0, 43.4, 51.4, 52.0, 53.6, 64.0, 72.1, 75.2, 108.4, 125.2, 139.5, 143.7, 155.7, 171.1, 171.7, 203.5 ppm; HRMS (ES+) calcd for C$_{23}$H$_{30}$NO$_8$ [M+H$^+$]: 448.1971, found: 448.1981.

EXAMPLE 17

Synthesis of 2-(N-methylamino)-salvinorin (Compound 11)

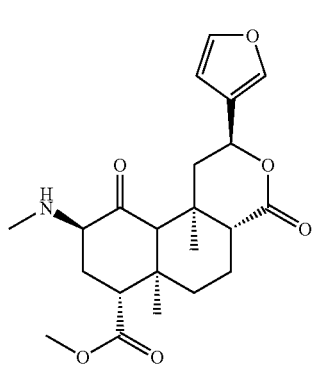

(11)

Compound 11 (3.7 mg, 29%) was prepared as a white solid from salvinorin B (12.2 mg, 31 μmol), CH$_2$Cl$_2$ (1.5 mL), trifluoromethanesulfonic anhydride (25 μL, 149 μmol), pyridine (25 μL, 309 μmol), and ethylamine (2.0 N in THF, 1.5 mL) utilizing method Scheme 1E. R$_f$ 0.42 (4:1, CH$_2$Cl$_2$: EtOAc); $^1$H NMR (CDCl$_3$) δ 1.09 (s, 3H), 1.45 (s, 3H), 1.53-1.66 (m, 4H), 1.72-1.76 (m, 1H), 1.82-1.88 (m, 1H), 2.07-2.16 (m, 2H), 2.27 (s, 3H), 2.29-2.40 (m, 1H), 2.48 (dd, J=5.7, 13.5 Hz, 1H), 2.97 (s, 1H), 3.05-3.07 (m, 1H), 3.13 (dd, J=3.3, 13.5 Hz, 1H), 3.69 (s, 3H), 5.54 (dd, J=5.1, 11.7 Hz, 1H), 6.37-6.38 (m, 1H), 7.40-7.41 (m, 2H); $^{13}$C NMR (CDCl$_3$) 15.2, 16.2, 18.1, 32.2, 34.6, 34.9, 38.4, 43.0, 43.4, 50.6, 51.4, 59.5, 67.1, 72.0, 79.6, 108.4, 125.6, 139.4, 143.7, 171.6, 173.1, 211.4 ppm; HRMS (ES+) calcd for C$_{22}$H$_{30}$NO$_6$ [M+H$^+$]: 404.2073, found: 404.2065.

EXAMPLE 18

Synthesis of 2-(2'-(N,N-dimethylamino)acetate)salvinorin B (Compound 12)

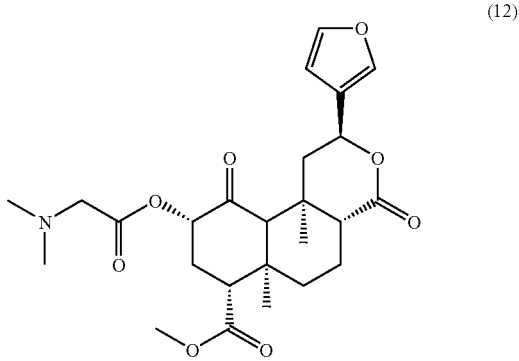

(12)

Compound 12 (4.8 mg, 51%) was prepared as a white solid from salvinorin B (7.8 mg, 20 μmol), N,N-dimethylglycine (6.3 mg, 61 μmol), DMAP (0.6 mg, 5 μmol), 1.0 M DCC in CH$_2$Cl$_2$ (60 μL), and CH$_2$Cl$_2$ (2 mL) using the method of Scheme 1B. R$_f$ 0.07 (4:1, CH$_2$Cl$_2$:EtOAc); $^1$H NMR (CDCl$_3$) δ 1.11 (s, 3H), 1.45 (s, 3H), 1.54-1.67 (m, 3H), 1.78-1.82 (m, 2H), 2.07 (dd, J=2.7, 10.7 Hz, 1H), 2.18 (s, 1H), 2.29-2.37 (m, 2H), 2.40 (s, 6H), 2.50 (dd, J=5.4, 13.2 Hz, 1H), 2.76 (t, J=8.4 Hz, 1H), 3.30 (d, J=16.7 Hz, 1H), 3.35 (d, J=16.7 Hz, 1H), 3.73 (s, 3H), 5.21 (t, J=10.2, 1H), 5.53 (dd, J=5.3, 11.9 Hz, 1H), 6.38 (s, 1H), 7.39-7.42 (m, 2H); $^{13}$C NMR (CDCl$_3$) 15.2, 16.4, 18.1, 30.8, 35.5, 38.2, 42.1, 43.3, 45.3, 51.4, 52.0, 53.6, 60.0, 64.1, 72.0, 75.1, 108.4, 125.2, 139.4, 143.7, 169.7, 171.1, 171.5, 201.5 ppm; HRMS (ES+) calcd for C$_{25}$H$_{34}$NO$_8$ [M+H$^+$]: 476.2284, found: 476.2277.

EXAMPLE 19

Synthesis of C(2) Ethers (13)

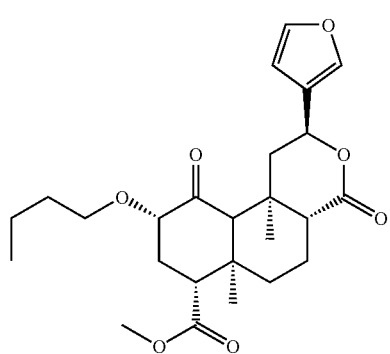

(14)

(15)

-continued (16)

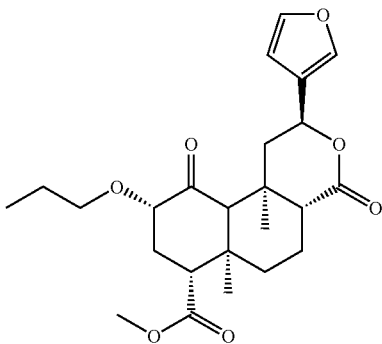

(17)

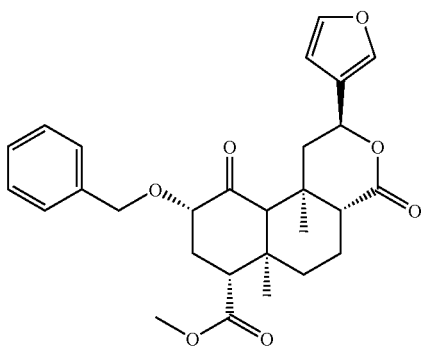

(71)

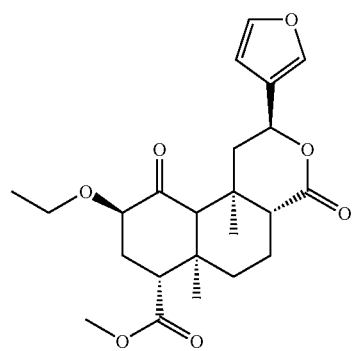

(72)

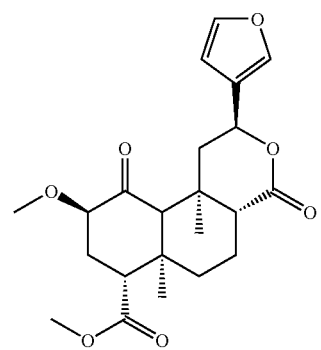

(73)

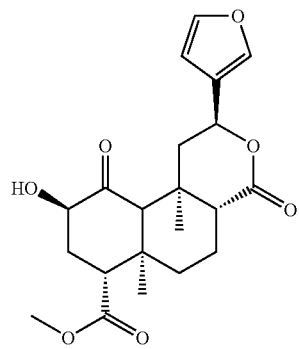

(19)

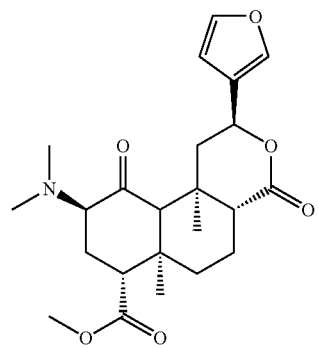

Compounds 13-17, 71, and 72 were prepared using the method of Scheme 1C.

Compound 73 was prepared as follows: to a solution of salvinorin B (150.0 mg, 0.38 mmol, 1 eq), PPh$_3$ (300.0 mg, 1.15 mmol, 3 eq), and 4-nitrobenzoic acid (192.5 mg, 1,15 mmol, 3 eq) in CH$_2$Cl$_2$ (30 mL) was added diisopropylazodicarboxylate (230 μL, 1.15 mmol, 3 eq) dropwise. The reaction solution was stirred at room temperature (3.5 hours). Saturated NaHCO$_3$ (30 mL) was added. The organic layer was washed with brine (30 mL), dried (MgSO$_4$) and concentrated. The residue was purified by column chromatography (SiO$_2$; 19:1, CH$_2$Cl$_2$:EtOAc) to obtain the 4-nitrobenzoate as a white solid. K$_2$CO$_3$ (52.5 mg, 0.38 mmol, 1 eq) was added to a cold (0° C.) suspension of the intermediate in MeOH (10 mL). The reaction mixture was stirred at 0° C. (10 minutes) and was concentrated. CH$_2$Cl$_2$ (10 mL) and aqueous 1 N HCl (10 mL) were added to the residue. The organic layer was washed with brine (10 mL), dried (MgSO$_4$), and concentrated. The reaction solution was concentrated and the residue was purified by column chromatography (SiO$_2$; 9:1, CH$_2$Cl$_2$:EtOAc to 4:1, CH$_2$Cl$_2$:EtOAc) to obtain the desired product (95.5 mg, 64%) as a white solid: R$_f$ 0.53 (4:1, CH$_2$Cl$_2$: EtOAc).

EXAMPLE 20

Synthesis of C(2) Amines and Related Structures (74)

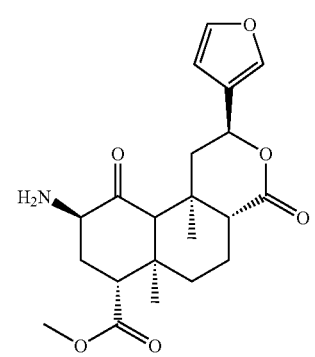

(75)

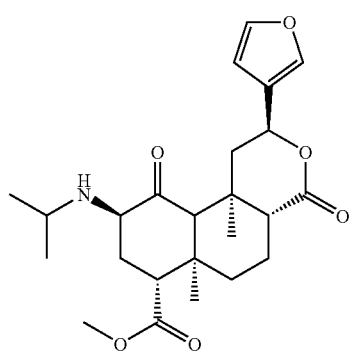

(18)

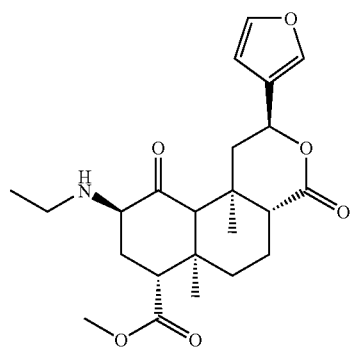

(76)

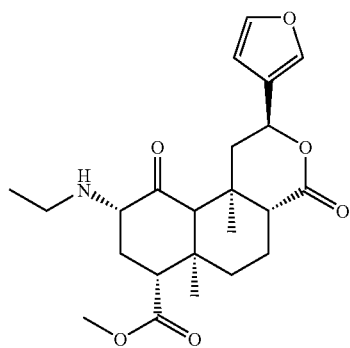

53
-continued
(77)
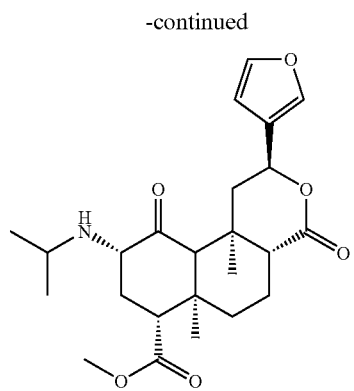
(78)
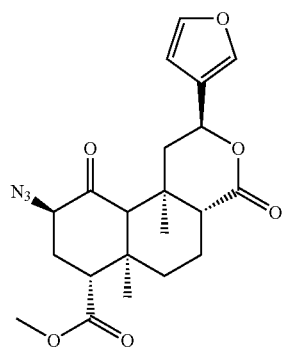
(79)
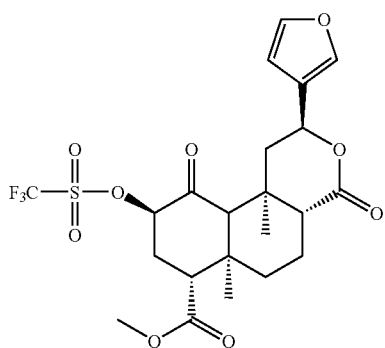
(80)
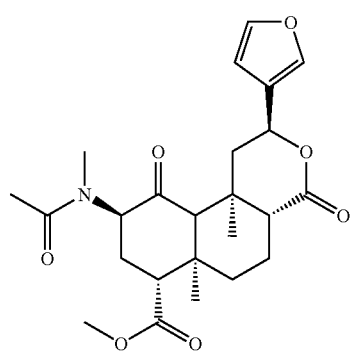
54
-continued
(81)
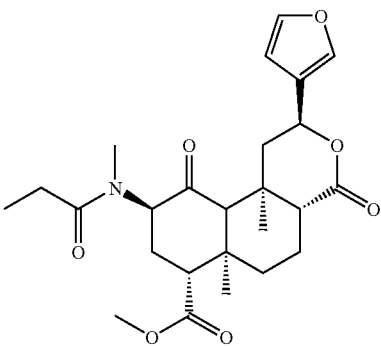
(82)
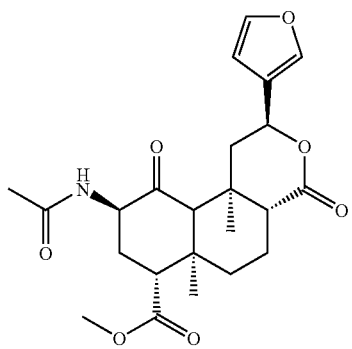
(83)
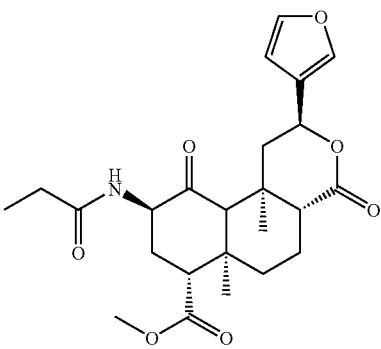
(84)
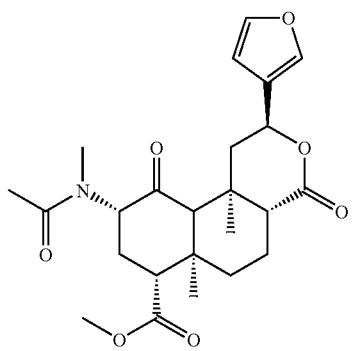

-continued (85)

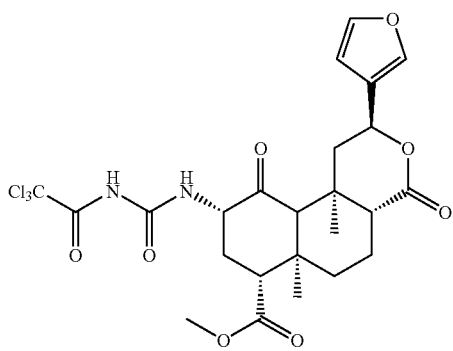

Compounds 18, 19, 75, 76, 77, and 79 were prepared using the method of Scheme 1E.

Compounds 80, 82, 83, and 84 were prepared using the method of Scheme 1F.

Compound 78 was prepared as follows: sodium azide (21.9 mg, 0.34 mmol, 1.1 eq) was added to a cold (0° C.) solution of 79 (129.0 mg, 0.31 mmol, 1 eq) in DMF (2 mL). The reaction mixture was stirred at 0° C. (1 hour). EtOAc (20 mL) and $H_2O$ (20 mL) were added to the reaction mixture. The organic layer was washed with saturated $NaHCO_3$ (20 mL), brine (20 mL), dried ($MgSO_4$), and volatiles were evaporated. The residue was purified by column chromatography ($SiO_2$; 2:1, hexanes: EtOAc) to obtain the desired product (63.1 mg, 50%) as a white solid: $R_f$ 0.36 (2:1, hexanes:EtOAc); HRMS (ES+) calcd for $C_{21}H_{26}N_3O_6$ [M+H$^+$]:416.1821, found: 416.1824.

Compound 74 was prepared as follows: A $CH_2Cl_2$ (1 mL) solution of $PPh_3$ (20.9 mg, 0.080 mmol, 1.1 eq) was added to a $CH_2Cl_2$ (1 mL) solution of 78 (30.0 mg, 0.072 mmol, 1 eq). The reaction mixture was stirred at room temperature (1.5 hours). EtOAc (20 mL) and $H_2O$ (20 mL) were added to the raction mixture. The organic layer was washed with saturated $NaHCO_3$ (20 mL), brine (20 mL), dried ($MgSO_4$), and evaporated. The residue was purified by column chromatography ($SiO_2$; 2:1, hexanes:EtOAc) to obtain the desired product (63.1 mg, 50%) as a white solid: $R_f$ 0.36 (2:1, hexanes:EtOAc).

Compound 81 was prepared as follows: a $CH_2Cl_2$ solution of triethylamine (3 µL, 0.022 mmol, 1.25 eq) and the acyl chloride or anhydride (2 µL, 0.022 mmol, 1.25 eq) was added to 11 (7.0 mg, 0.017 mmol, 1 eq). The reaction solution was stirred at room temperature (10 minutes). The reaction was concentrated and the residue was purified by column chromatography ($SiO_2$; 4:1, $CH_2Cl_2$:EtOAc) to obtain the desired product (5.7 mg, 71%) as a white solid: $R_f$ 0.25 (4:1, $CH_2Cl_2$: EtOAc).

Compound 85 was prepared as follows: Trichloroacetylisocyanate (9 µL, 0.077 mmol, 5 eq) was added to a $CH_2Cl_2$ (1 mL) solution of 74 (6.0 mg, 0.015 mmol, 1 eq). The reaction mixture was stirred at room temperature (5 minutes). The reaction solution was concentrated and the residue was purified by column chromatography ($SiO_2$; 4:1, $CH_2Cl_2$: EtOAc) to obtain the desired product (4.7 mg, 53%) as a white solid: $R_f$ 0.53 (19:1, $CH_2Cl_2$:MeOH).

EXAMPLE 21

Synthesis of C(2) Carbamates (20)

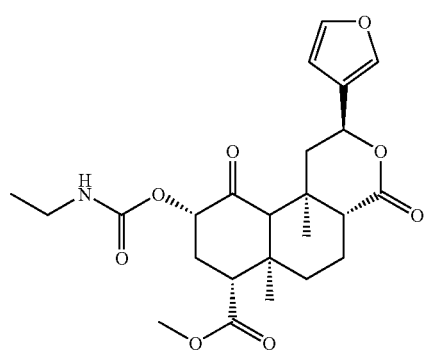

(86)

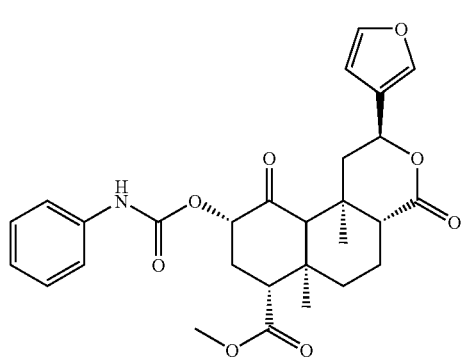

(87)

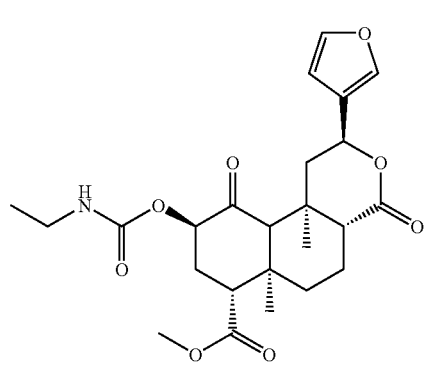

(88)

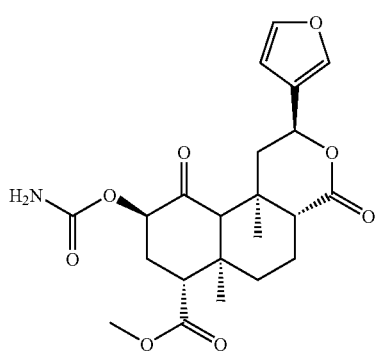

Compound 20, 86, 87, and 88 was prepared using the method of Scheme 1D.
EXAMPLE 22
Synthesis of C(2) Esters
(21)
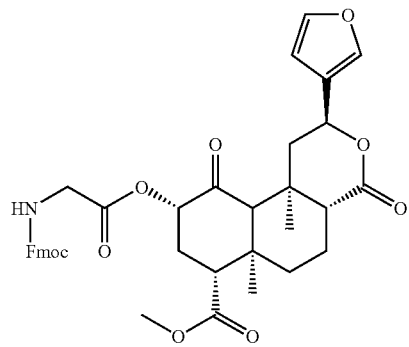
(22)
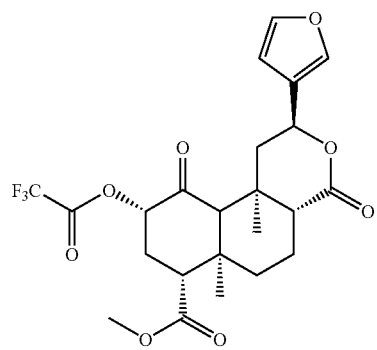
(23)
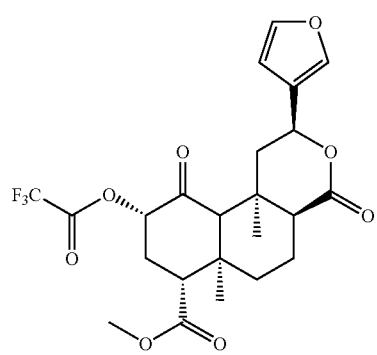
(24)
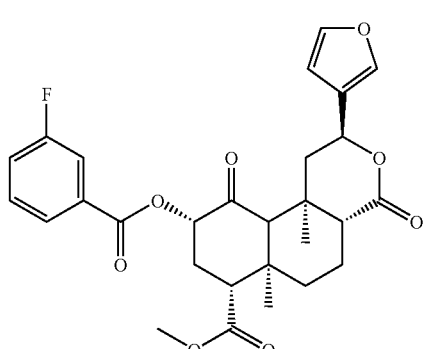
-continued
(25)
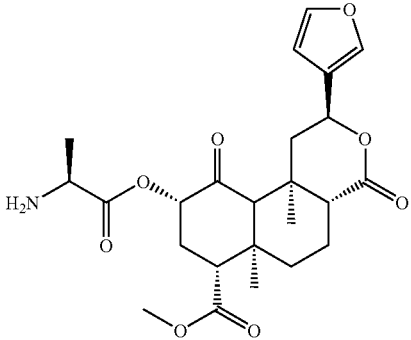
(26)
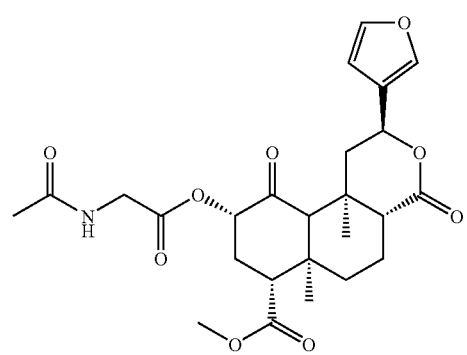
(27)
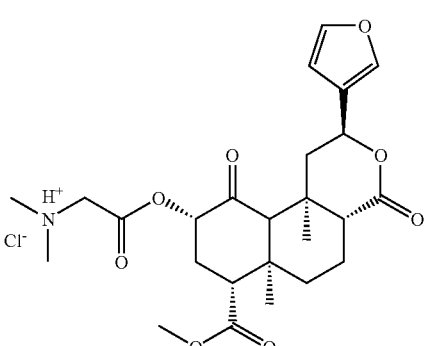
(28)
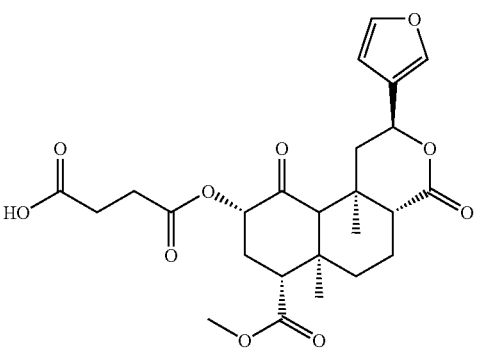

(89)
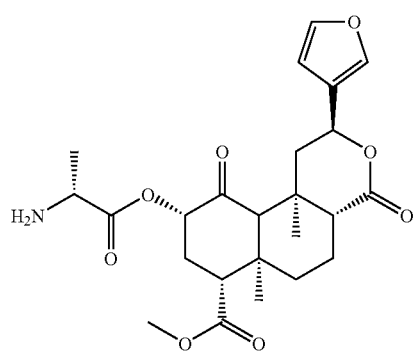

(90)
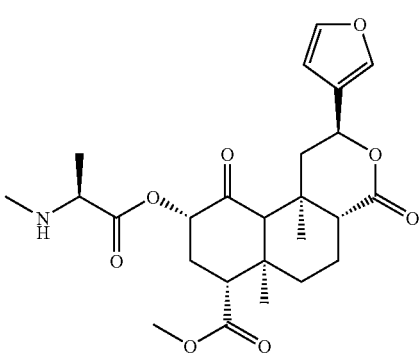

(91)
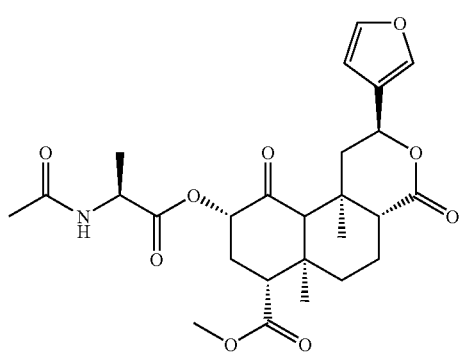

(92)
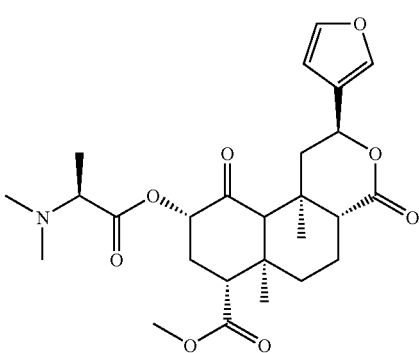

(93)
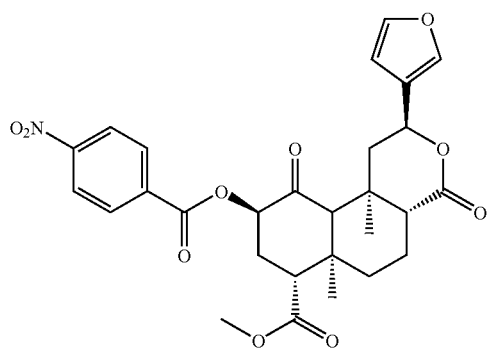

(94)
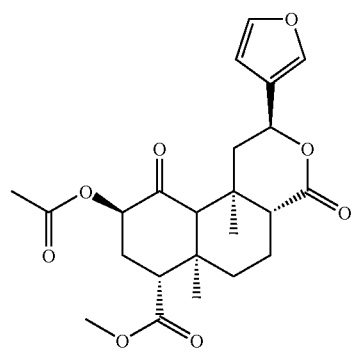

Compounds 21-27 and 89-92 were prepared using the method of Scheme 1B.

Compounds 93 and 94 were prepared using the method of Scheme 1A.

Compound 28 was prepared from salvinorin B according to the following procedure: To a cold (0° C.) suspension of salvinorin B (8.8 mg, 23 mmol) and succinic anhydride (5.6 mg, 56 mmol) was added DBU (10 mL, 68 mmol) dropwise. The reaction mixture was stirred at 0° C. (15 minutes), washed with aqueous 3% citric acid, saturated aqueous NaHCO$_3$, brine, dried (MgSO$_4$), and concentrated in vacuo. The residue was purified by column chromatography (SiO$_2$; 19:1, CH$_2$Cl$_2$:MeOH) to obtain 5.4 mg (49%) of pure 28 as a colorless oil.

EXAMPLE 23

Synthesis of C(2) Carbonates (29)

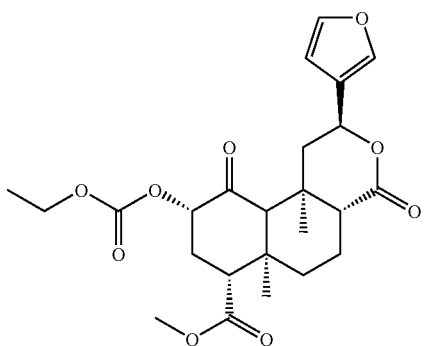

(30)

To a solution of Salvinorin-B (15 mg, 1 equivalent) in dry dichloromethane (2 mL), was added alkyl chloroformate (5 equivalents) followed by DMAP (5 mg) and the mixture stirred at room temperature for 15 hours. TLC was used to monitor the progress of the reaction. After the reaction was complete the reaction mixture was diluted with dichloromethane, washed with water, and dried over anhydrous $Na_2SO_4$. The organic solvent was removed under vacuum. The resulting crude product was purified by column chromatography (20% ethyl acetate in hexane as the eluent) to obtain 2-substituted salvinorin carbonate as a colorless solid.

EXAMPLE 24

Synthesis of C(4) Derivatives

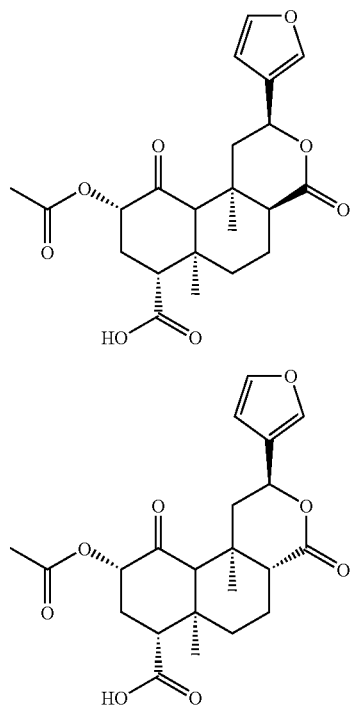

To a solution of Salvinorin A (0.5 g, 1.15 mmol, 1 eq) in dry pyridine (10 mL), was added lithium iodide (0.76 g, 5.70 mmol, 5 equivalents). The reaction mixture was wrapped with an aluminum foil and heated to reflux for 36 hours. The volatiles were removed under vacuum, and the residue was quenched with ice and treated with 5% aqueous HCl until slightly acidic followed by extraction with ethyl acetate. The organic layer washed with water, dried over anhydrous $Na_2SO_4$, and purified by column chromatography over silica gel (mobile phase: ethyl acetate/hexane followed by ethyl acetate, and finally by 10% methanol in ethyl acetate). Eluting sequentially were epi-Salvinorin A (25 mg, 5%), recovered Salvinorin A (20 mg, 4%), epi-demethyl Salvinorin (31, 100 mg, 23%) and demethyl Salvinorin (32, 150 mg, 33%), respectively. Compound 31: $^1$H NMR ($CDCl_3$, 300 MHz): 1.14 (s, 3H, $CH_3$), 1.46 (s, 3H, $CH_3$), 1.65 (m, 1 H), 1.90 (m, 1 H), 2.05 (s, 1 H), 2.10 (m, 1 H), 2.18 (s, 3H, $CH_3$), 2.30 (m, 1 H), 2.50 (dd, J=4 Hz, 12 Hz, 1H), 2.80 (dd, J=5 Hz, 10 Hz, 1H), 5.20 (dd, J=8 Hz, 10.2 Hz, 1H), 5.50 (dd, J=6 Hz, 8.5 Hz, 1H), 6.38 (s, 1H), 7.40 (s, 1H), 7.41 (s,1H); $^{13}$CNMR ($CDCl_3$, 75 MHz): 15.19, 16.42, 18.10, 20.55, 30.59, 35.44, 38.07, 42.02, 43.30, 51.29, 53.36, 63.95, 72.08, 74.90, 108.35, 125.13, 139.43, 143.73, 170.00, 171.27, 175.75, 201.87. Compound 32: $^1$H NMR ($CDCl_3$, 300 MHz): 1.10 (s, 3H, $CH_3$), 1.50 (m, 2H), 1.64 (s, 3H, $CH_3$), 1.76 (m, 1 H), 1.85 (m, 1 H), 2.05 (m, 1 H), 2.16 (s, 3H, $CH_3$), 2.20 (m, 1 H), 2.35 (m, 2H), 2.47 (d, J=3 Hz, 1H), 2.80 (dd, J=3 Hz, 5.1 Hz, 1H), 5.10 (dd, J=7.8 Hz, 10 Hz, 1H), 5.30 (d, J=12 Hz, 1H), 6.38 (s, 1H), 7.38 (s, 1H), 7.44 (s,1H); $^{13}$CNMR ($CDCl_3$, 75 MHz): 15.26, 17.52, 20.53, 24.60, 30.51, 33.82, 34.71, 42.14, 45.18, 47.86, 52.65, 63.90, 70.10, 75.11, 108.50, 123.28, 139.71, 143.58, 169.91, 173.71, 176.20, 202.35.

| C(4) Esters |
|---|
| 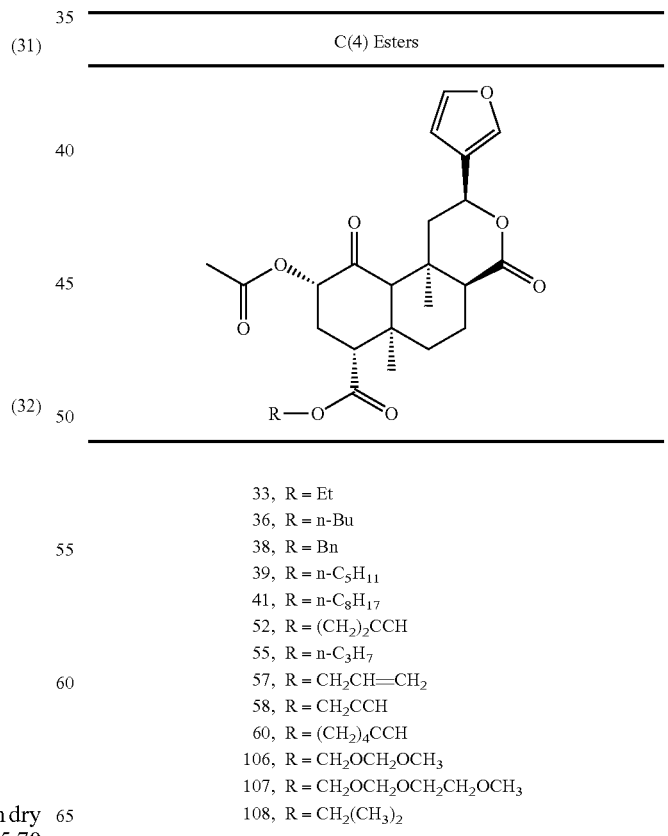 |
| 33, R = Et |
| 36, R = n-Bu |
| 38, R = Bn |
| 39, R = n-$C_5H_{11}$ |
| 41, R = n-$C_8H_{17}$ |
| 52, R = $(CH_2)_2CCH$ |
| 55, R = n-$C_3H_7$ |
| 57, R = $CH_2CH=CH_2$ |
| 58, R = $CH_2CCH$ |
| 60, R = $(CH_2)_4CCH$ |
| 106, R = $CH_2OCH_2OCH_3$ |
| 107, R = $CH_2OCH_2OCH_2CH_2OCH_3$ |
| 108, R = $CH_2(CH_3)_2$ |

C(4) Esters

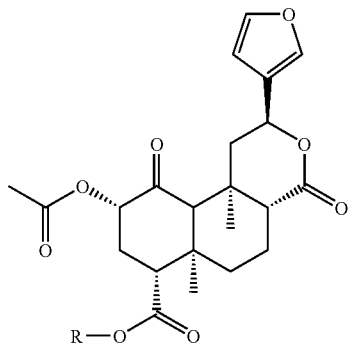

34, R = Et
35, R = n-Bu
37, R = Bn
40, R = n-C$_5$H$_{11}$
42, R = n-C$_8$H$_{17}$
53, R = (CH$_2$)$_2$CCH
54, R = n-C$_3$H$_7$
56, R = CH$_2$CH=CH$_2$
59, R = CH$_2$CCH
51, R = (CH$_2$)$_4$CCH
95, R = CH$_2$OCH$_2$OCH$_3$
96, R = CH$_2$OCH$_2$OCH$_2$CH$_2$OCH$_3$
109, R = CH$_2$(CH$_3$)$_3$

To a solution of the acid (31 or 32, 1 equivalent) in dry dichloromethane was added corresponding alcohol (1.5 equivalents), DCC (1.5 equivalents) and DMAP (catalytic amount). The reaction mixture was stirred at room temperature for 15 hours under an inert atmosphere, followed by quenching with water and filtration to remove the insoluble white solid. The reaction mixture was then diluted with dichloromethane and washed with saturated ammonium chloride solution and dried over anhydrous sodium sulfate. Volatiles were removed under vacuum and the crude reaction mixture was purified by chromatography on silica gel with 25% ethyl acetate in hexane as the eluent to obtain pure esters.

C(4) Amides

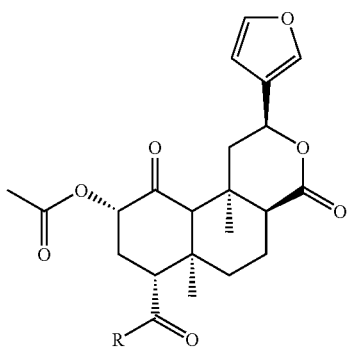

44, R = NHBn
48, R = NHCH$_2$CH$_2$Ph
60, R = NH(CH$_2$)$_4$CCH
63, R = NHCH$_2$CH$_2$CN

C(4) Amides

61, R = HN–CH(CH$_3$)–COOBn

46, R = morpholinyl

99, R = HN–CH(CH$_3$)–COOBn

101, R = HN–CH$_2$–COOBn

104, R = pyrrolidinyl-2-COOBn

110, R = HN–CH$_2$–cyclopropyl

111, R = HN–CH(CH$_2$OH)–COOBn

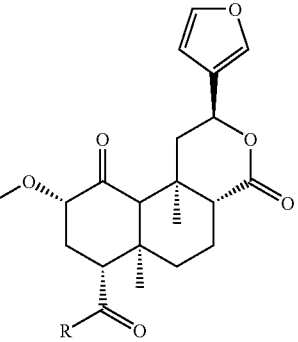

43, R = NHBn
47, R = NHCH$_2$CH$_2$Ph
49, R = NHCH$_2$CH$_2$OH
64, R = NHCH$_2$CH$_2$CN

62, R = HN–CH(CH$_3$)–COOBn

45, R = morpholinyl

50, R = 4-methylpiperidinyl

97, R = HN–CH$_2$–cyclopropyl

C(4) Amides

98, R = HN⋯CH(CH₃)COOBn

100, R = HN–CH₂–COOBn

102, R = HN⋯CH(CH₂OH)COOBn

103, R = pyrrolidine-2-COOBn (N-linked)

105, R = HN⋯CH(CH₂-imidazole)COOBn

To a solution of the acid (31 or 32, 1 equivalent) in dry DMF was added the corresponding amine or amino acid (2.0 equivalents), HOBt (1.5 equivalents) and EDCI (1.5 equivalents). The reaction mixture was stirred at room temperature for 24 hours under an inert atmosphere. Volatiles were removed under vacuum. The reaction mixture was then diluted with ethyl acetate, washed with water and saturated ammonium chloride solution, and dried over anhydrous sodium sulfate. Volatiles were removed under vacuum and the crude reaction mixture was purified by chromatography on silica gel with ethyl acetate in hexane (gradient ratio as needed) as the eluent to obtain pure amides.

EXAMPLE 25

Synthesis of Tetrahydrofuranyl Derivatives

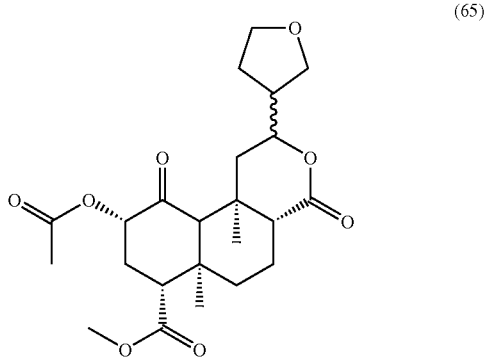
(65)

Salvinorin A (9.0 mg, 21 mmol) in EtOAc (10 mL) was hydrogenated in the presence of 5% Pt/C (catalytic amount) at room temperature (3 days). The solution was concentrated in vacuo and the residue was purified by column chromatography ($SiO_2$; 19:1, $CH_2Cl_2$:MeOH) to obtain 3.5 mg (36%) of pure 62 as a white solid: $R_f$ 0.50 (19:1, $CH_2Cl_2$:MeOH).

EXAMPLE 26

Synthesis of C(17) Derivatives

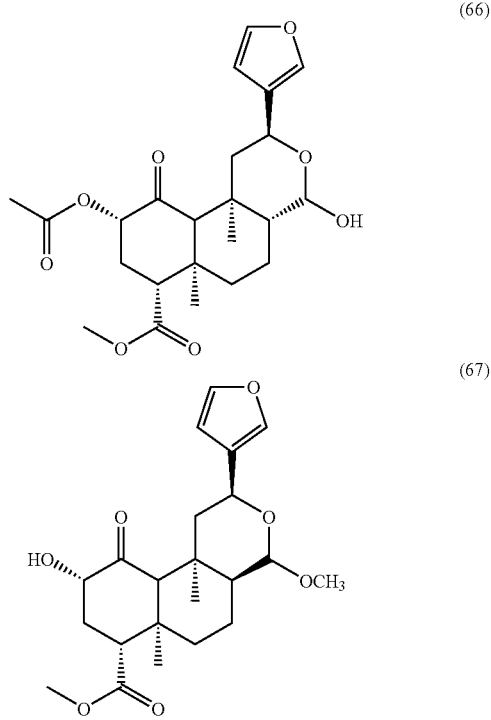

Synthesis of compound 66: To a solution of Salvinorin A (43 mg, 100 mmol) in 5 mL of dry THF under inert atmosphere was added lithium tri-t-butoxyaluminohydride (0.5 M, 0.6 ml, 600 mmol) and the mixture heated to reflux for 8 hours. The reaction mixture was cooled in an ice bath and quenched with dilute HCl and stirred at room temperature for 30 minutes. Volatiles were removed under vacuum and the reaction mixture extracted with chloroform, washed with water, and dried. The crude product was purified by column chromatography on a silica gel column (25% ethyl acetate in hexane) to obtain 10 mg of unreacted starting material followed by 30 mg (60% Yield) of compound 66 as a colourless solid. $^1$H NMR ($CDCl_3$, 300 MHz): 1.08 (s, 3H, $CH_3$), 1.40 (s, 3H, $CH_3$), 2.15 (s, 3H, $CH_3$), 2.80 (m, 2H), 3.71 (s, 3H, $COOCH_3$), 4.80 (d, J=9 Hz, 1H), 4.90 (d, J=12 Hz, 1H), 6.38 (d, J=0.3 Hz, 1H), 7.38 (m, 2H); $^{13}$C NMR ($CDCl_3$, 75 MHz): 15.00, 16.74, 17.68, 20.61, 30.89, 35.69, 38.85, 42.41, 44.76, 51.81, 52.23, 53.72, 65.44, 66.30, 75.06, 94.19, 108.80, 126.21, 139.12, 143.07, 169.90, 171.90, 202.49.

Synthesis of compound 67: To a solution of compound 66 (4 mg, 10 mmol) in 1 mL of dry MeOH under inert atmosphere was added trimethylsilylchloride (0.1 ml, 80 mmol) at 0° C. The reaction mixture was warmed to room temperature and stirred overnight. Volatiles were removed under vacuum and the reaction mixture was extracted with methylene chloride, washed with water, and dried. The crude product was purified by column chromatography on a silica gel column (25% ethyl acetate in hexane) to obtain 3.2 mg (78% Yield) of compound 67 as a colourless oil. $^1$H NMR ($CDCl_3$, 300

MHz): 1.08 (s, 3H, CH$_3$), 1.40 (s, 3H, CH3), 2.80 (m, 2H), 3.71 (s, 3H, COOCH$_3$), 3.50 (s, 3H), 4.80 (d, J=9 Hz, 1H), 4.90 (d, J=12 Hz, 1 H), 6.38 (d, J=0.3 Hz, 1H), 7.38 (m, 2H).

EXAMPLE 27

Synthesis of Lactone Ring Cleaved Derivatives

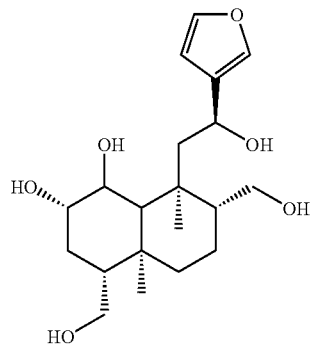

(68)

Synthesis of compound 68: To a solution of Salvinorin A (21.5 mg, 50 mmol) in dry THF (5 ml) was added lithium aluminium hydride (1 M in THF, 0.15 ml, 150 mmol) at 0° C. and the mixture stirred at room temperature for 4 hours. The reaction was quenched with dilute HCl until slightly acidic according to pH paper. Volatiles were removed under vacuum and the product extracted with chloroform (3×10 mL), washed with water and dried. The crude product was purified by column chromatography (silica gel/ethyl acetate and 3% ethyl acetate in methanol) to afford 10 mg (60% yield) of compound 68. $^1$H NMR (CD$_3$OD, 300 MHz):1.07 (s, 3H, CH$_3$), 1.20 (m, 2H), 1.34 (s, 3H, CH$_3$), 1.50 (m, 1H), 1.80 (m, 2 H), 3.10 (m, 1 H), 3.30 (m, 1 H), 3.70 (m, 1 H), 4.10 (s, 1 H), 4.65 (d, J=9 Hz, 1 H), 4.85 (d, J=11 Hz, 1 H), 6.35 (s, 1H), 7.32 (d, J=1.8 Hz, 1H), 7.36 (s, 1 H); $^{13}$C NMR (CDCl$_3$, 75 MHz):16.75, 18.47, 19.56, 29.76, 37.54, 38.52, 42.23, 47.15, 50.69, 55.07, 58.92, 62.85, 67.62, 70.18, 73.93, 95.71, 110.06, 128.85, 140.38, 144.10.

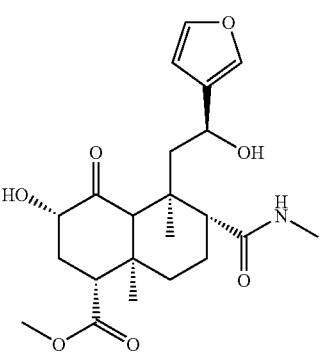

(69)

Synthesis of compound 69: A solution of salvinorin A (14 mg, 32 mmol) in methylamine (2.0 M in THF, 2 mL) was stirred at room temperature (18 hours). The solution was concentrated in vacuo and the residue was purified by column chromatography (SiO$_2$; 19:1, CH$_2$Cl$_2$:MeOH) to obtain 9.1 mg (67%) of pure 66 as a white solid: R$_f$ 0.14 (19:1, CH$_2$Cl$_2$: MeOH).

EXAMPLE 28

Synthesis of C(1) Deoxy Derivatives

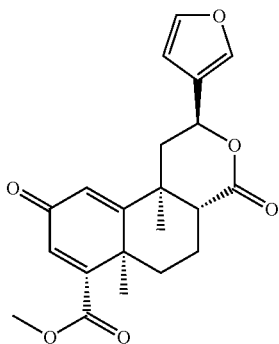

(70)

Synthesis of compound 70: To a solution of Salvinorin A (21.5 mg, 50 mmol) in 1.5 mL methanol was added Ba(OH)$_2$ (17 mg, 100 mmol) with stirring at room temperature. The reaction mixture turned a deep red color and after 1 hour the reaction was quenched with ice, neutralized with dilute HCl, and extracted with chloroform (2×10 ml). The organic layer was dried over anhydrous sodium sulfate and the crude product was purified by column chromatography (silica gel/20% ethyl acetate in Hexane) to obtain 14 mg (75%) of compound 70. $^1$H NMR (CDCl$_3$, 300 MHz): 1.68 (s, 3H, CH$_3$), 1.75 (s, 3H, CH$_3$), 2.0 (m, 2H), 2.25 (m, 1H), 2.50 (m, 1H), 3.00 (m, 1H), 3.10 (m, 1H), 3.83 (s, 3H, COOCH$_3$), 5.40 (dd, J=2.4 Hz, 7.5 Hz, 1H), 6.40 (d, J=0.7 Hz, 1H), 6.92 (s, 1H), 6.98 (s, 1H), 7.40 (m, 1H), 7.48 (m, 1H); $^{13}$C NMR (CDCl$_3$, 75 MHz): 21.91, 24.98, 28.35, 30.20, 36.80, 37.70, 42.28, 44.90, 52.59, 70.87, 108.42, 124.57, 128.19, 139.61, 139.93, 143.64, 145.64, 157.50, 165.37, 173.10, 180.74.

EXAMPLE 29

Radioligand Binding Assays

Compounds can be characterized in radioligand receptor binding assays, using ligands that are specific for the mu, delta and kappa receptors. The binding assays may utilize guinea pig brain membranes or stably transfected Chinese Hamster Ovary (CHO) cells expressing each of the three opioid receptors. Membranes can be isolated from CHO cells that stably express either the human mu, delta or kappa opioid receptors. At approximately 80% confluence, the cells are harvested by the use of a cell scraper. The cells and media from the plates are centrifuged at 200×g for 10 mm at 4° C.; resuspended in 50 mM Tris-HCl, pH 7.5; homogenized by the use of a Polytron; centrifuged at 48,000×g for 20 mm at 4° C.; and resuspended in 50 mM Tris-HCl, pH 7.5, at a protein concentration of 5-10 mg/ml, as determined by the Bradford method. The membranes are stored frozen, at −80° C. until use.

Cell membranes are incubated at 25° C. with the radiolabeled ligands in a final volume of 1 ml of 50 mM Tris-HCl, pH 7.5. Incubation times of 60 minutes are used for the mu-selective peptide [$^3$H]DAMGO and the kappa-selective ligand [³H]Diprenorphine, and 4 hours of incubation for the delta-selective antagonist [³H]naltrindole. Nonspecific binding is measured by inclusion of 1 μM naloxone. The binding can be terminated by filtering the samples through Schleicher & Scheull No. 32 glass fiber filters using a Brandel 48-well cell harvester. The filters are subsequently washed three times with 3 mL of cold 50 mM Tris-HCl, pH 7.5, and can be counted in 2 ml of Ecoscint A scintillation fluid. For [³H] Diprenorphine binding, the filters are soaked in 0.1% polyethylenimine for at least 30 minutes before use. IC50 values can be calculated by a least squares fit to a logarithm-probit analysis. Ki values of unlabeled compounds are calculated from the equation $Ki=(IC_{50})/1+S$ where S=(concentration of radioligand)/(Kd of radioligand). Cheng and Prusoff, *Biochem. Pharmacol.* 22:3099 (1973). Alternatively, guinea pig brain membranes can be prepared and used as previously described in Neumeyer, et al., *J. Med. Chem.* 43:114 (2000). For further details see Huang et al., *J. Pharmacol. Exp. Ther.* 297:688 (2001); and Zhu et al., *J. Pharmacol. Exp. Ther.* 282:676 (1997). Other buffers may be used in the binding assay.

EXAMPLE 30

[³⁵S]GTPγS Binding Assays

Membranes from the CHO cell lines, expressing either the mu, delta or kappa receptor, are incubated with 12 concentrations of each compound for 60 minutes at 30° C. in a final volume of 0.5 ml of assay buffer (50 mM Tris-HCl, 3 mM $MgCl_2$, 0.2 mM EGTA, 100 mM NaCl, pH 7.5) containing 3 μM GDP and 0.08 nM [³⁵S]GTPγS. Basal binding can be determined in the presence of GDP and the absence of test compounds, and nonspecific binding can be determined by including 10 μM unlabeled [³⁵S]GTPγS. The incubation can be terminated by filtration under vacuum through glass fiber filters, followed by three washes with 3 ml ice-cold 50 mM Tris-HCl, pH 7.5. Samples can be allowed to equilibrate overnight and can be counted in 2 ml Ecoscint A scintillation fluid for 2 minutes in a liquid scintillation counter.

For [³⁵S]GTPγS binding assays, percent stimulation of [³⁵S]GTPγS binding is defined as [(stimulated binding-basal binding) basal binding]×100. Percent stimulation is plotted as a function of compound concentration (log scale), and $EC_{50}$ and $E_{max}$ values are determined by linear regression analysis. All data is compared across conditions using ANOVA and non-paired two-tailed Student's tests. For further details see Huang et al., *J. Pharmacol. Exp. Ther.* 297:688 (2001); and Zhu et al., *J. Pharmacol. Exp. Ther.* 282:676 (1997).

EXAMPLE 31

Forced Swim Test (FST)

The FST is a two day procedure in which rats swim under conditions in which escape is not possible. On the first day, the rats are forced to swim for 15 minutes. The rats initially search for an escape from the water, but eventually adopt a posture of immobility in which they make only the movements necessary to keep their heads above water. Upon re-testing one day later, latencies to become immobile (an indicator of how rapidly the rats "give up" in response to a familiar stressor) are decreased, which is inferred as despair. Standard antidepressants such as desipramine (DMI) and fluoxetine (FLX) extend latencies to become immobile. Drug efficacy in this animal model is predictive of antidepressant efficacy in humans. The FST has been described by Mague et al., *J. Pharmacol. Exp. Ther.* 305:323 (2003).

Figure 3A:
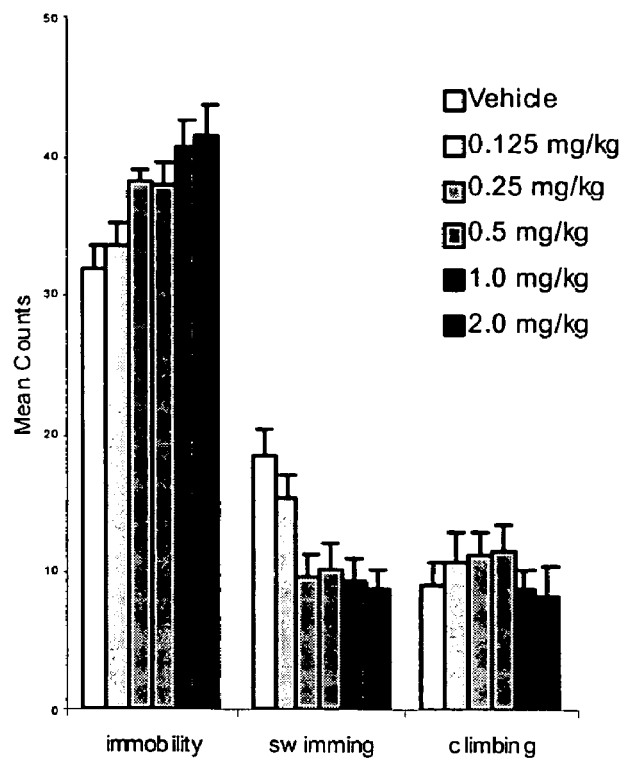
FIG. 3A is a graph showing the effect produced by administering salvinorin A to rats in the forced swim test.
Figure 3B:
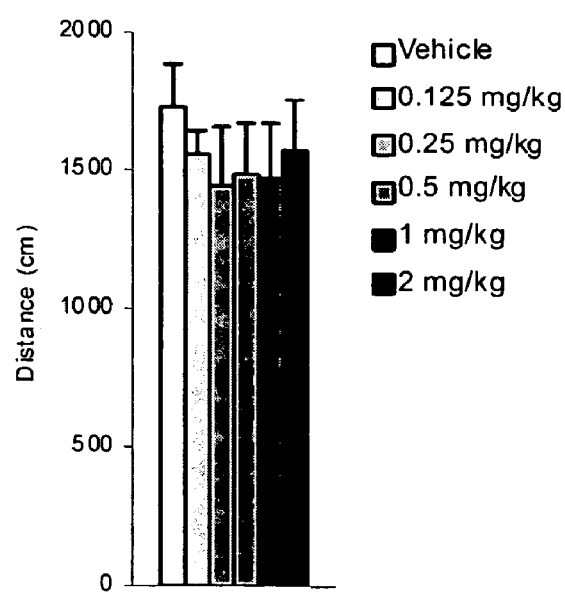
FIG. 3B is a graph showing the effect produced by administering salvinorin A to rats in a locomotor activity test.

Salvinorin A produces depressive-like effects in the forced swim test in rats without affecting locomotor activity (see FIGS. 3A and 3B).

EXAMPLE 32

Intracranial Self-Stimulation (ICSS)

Intracranial self-stimulation (ICSS) is highly sensitive to the function of brain reward systems. In this assay, rodents respond to self-administer rewarding electrical stimulation through electrodes implanted within the limbic system. Changes in the rewarding efficacy of the stimulation shift the rate-frequency functions: leftward shifts (reflecting decreases in ICSS thresholds) imply that the stimulation is more rewarding as a result of a treatment, whereas rightward shifts (reflecting increases in thresholds) imply that it is less rewarding. The effects of many types of treatments on ICSS have been described. Most drugs of abuse decrease the amount of stimulation required to sustain responding: this is indicated by leftward shifts in rate-frequency functions and decreased ICSS thresholds. Conversely, agents that block drug reward (dopamine or kappa-opioid receptor agonists) increase the amount of stimulation required to sustain responding: this is indicated by rightward shifts in rate-frequency functions, and increased ICSS thresholds. Thus ICSS is sensitive to manipulations that increase or decrease reward.

Considering that mania is typically associated with increases in reward-driven behavior, the ICSS test may be a reasonable model of mania. Thus drugs that reduce the rewarding effects of the electrical stimulation may have some efficacy in the treatment of mania or related states.

Figure 4:
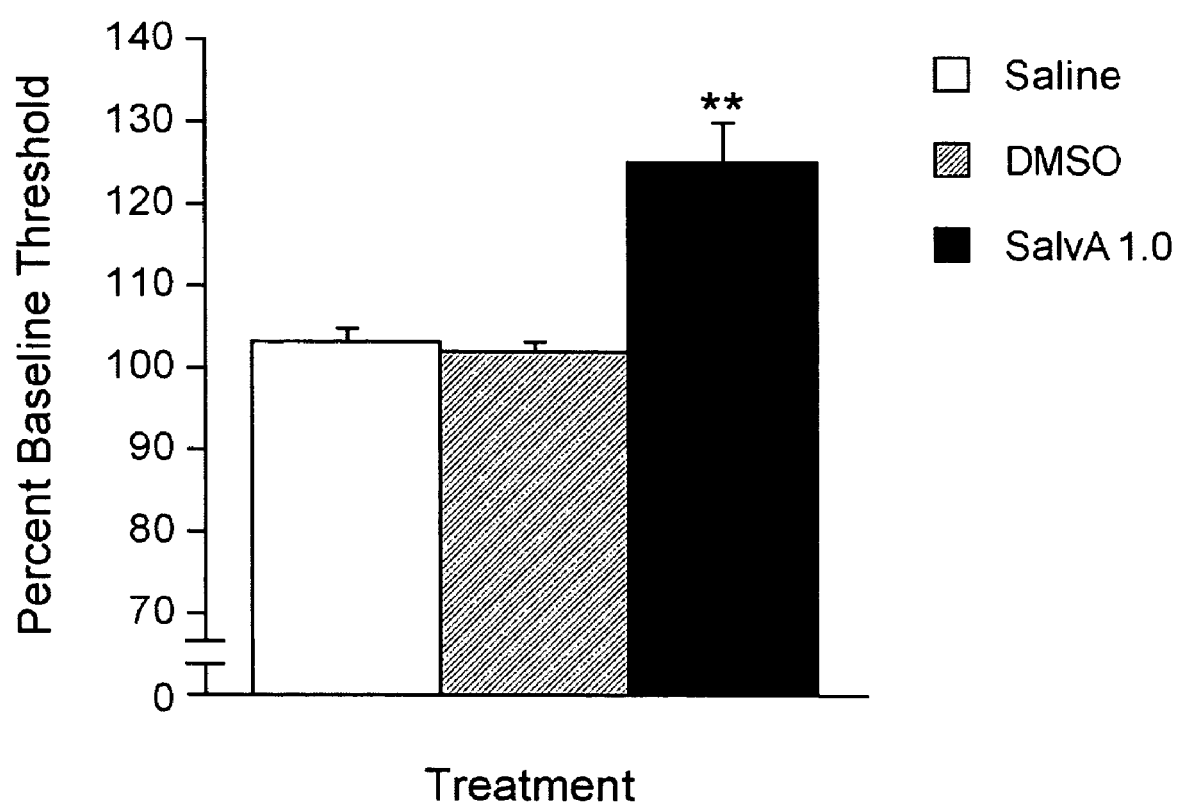
FIG. 4 is a graph showing the effect of various treatments on the rewarding effects of lateral hypothalamic brain stimulation using intracranial self-stimulation (ICSS) thresholds (Mean±SEM) in rats.

We have found that intraperitoneal administration of 1.0 mg/kg of salvinorin A (a dose with depressive-like effects as demonstrated in the forced swim test (FST) in rats) significantly elevates ICSS thresholds (see FIG. 4). In 1-hour test sessions, injections (1 ml/kg) of 0.9% saline or 70% DMSO (the vehicle for salvinorin A) had no effects on ICSS thresholds, whereas salvinorin A (1.0 mg/kg, IP) significantly elevated ICSS thresholds. Elevations of ICSS thresholds indicate that the lateral hypothalamic brain stimulation is less rewarding as the result of treatment. These findings indicate that salvinorin A in rats causes anhedonia, a hallmark symptom of depressive disorders in humans. Accordingly, kappa agonists may be useful in the treatment of mania and related states in humans.

EXAMPLE 33

Kappa Opioid Receptor Binding

The affinities (Ki), potencies ($EC_{50}$) and efficacies of test compounds on human kappa opioid receptor were measured. 2-methoxymethyl-salvinorin B was found to be seven times more potent than salvinorin A. The results are summarized in Table 1.

TABLE 1

| | Compound tested | Ki(nM) | EC$_{50}$(nM) | Efficacy[1,2] |
|---|---|---|---|---|
| 1 | salvinorin B | 155 ± 23 | 371 ± 49 | 98 |
| 2 | 2-propionyl-salvinorin B | 7.2 ± 0.5 | 20.4 ± 3.4 | 94 |
| 3 | 2-butanoyl-salvinorin B | 4.9 ± 0.6 | 9.9 ± 0.6 | 97 |
| 4 | 2-methoxy-salvinorin B | 220 ± 12 | 389 ± 76 | 98 |
| 5 | episalvinorin B | 43 ± 5 | 193 ± 4 | 102 |
| 6 | 2-methoxymethyl-episalvinorin B | 30 ± 3 | 92 ± 31 | 100 |
| 7 | episalvinorin A | 77 ± 4 | 307 ± 92 | 94 |
| 8 | 2-methoxymethyl-salvinorin B | 0.4 ± 0.02 | 0.6 ± 0.2 | 98 |
| 9 | 2-(O-formamide)-salvinorin B | 3.2 ± 0.2 | 6.2 ± 1.4 | 99 |
| 10 | 2-(O-(N-methyl)formamide)-salvinorin B | 83 ± 9 | 201 ± 10 | 81 |
| 11 | 2-(N-methylamino)-salvinorin | >10 μM | N.A. | N.A. |
| 12 | 2-(2'-(N,N-dimethylamino)acetate)salvinorin B | >10 μM | N.A. | N.A. |
| 13 | 2-n-butoxy-salvinorin B | 35.8 ± 5.1 | 104 ± 17 | 105 |
| 14 | 2-allyloxy-salvinorin B | 60.1 ± 5.1 | 145 ± 33 | 106 |
| 15 | 2-ethoxy-salvinorin B | 7.9 ± 0.3 | 18.6 ± 2.6 | 103 |
| 16 | 2-propoxy-salvinorin B | 28.7 ± 3.0 | 67.4 ± 9.9 | 100 |
| 17 | 2-benzyloxy-salvinorin B | 75.7 ± 5.9 | 161 ± 14 | 102 |
| 18 | 2-(N-ethylamino)-salvinorin | 28.9 ± 1.0 | 68.9 ± 5.3 | 111 |
| 19 | 2-(N,N-dimethylamino)-salvinorin | 90.9 ± 2.5 | 343 ± 12 | 105 |
| 20 | 2-(O-(N-ethyl)formamide)-salvinorin B | 462 ± 20 | >1,000 | N.A. |
| 21 | Compound 21 | >277.1 | >4117.4 | N.A. |
| 25 | Compound 25 | >10 μM | N.A. | N.A. |
| 26 | Compound 26 | >10 μM | N.A. | N.A. |
| 27 | Compound 27 | >10 μM | N.A. | N.A. |
| 29 | Compound 29 | >91 | >1719.3 | N.A. |
| 30 | Compound 30 | >78.9 | >1123.5 | N.A. |
| 31 | Compound 31 | 17.3 | 84.0 | 93 ± 5 |
| 32 | Compound 32 | >114.8 | >1228.5 | N.A. |
| 33 | Compound 33 | >10 μM | N.A. | N.A. |
| 34 | Compound 34 | 365 ± 26 | 94.4 ± 4.1 | 109.8 ± 6.4 |
| 35 | Compound 35 | >10 μM | N.A. | N.A. |
| 37 | Compound 37 | >10 μM | N.A. | N.A. |
| 40 | Compound 40 | >10 μM | N.A. | N.A. |
| 42 | Compound 42 | >10 μM | N.A. | N.A. |
| 51 | Compound 51 | 679 ± 112 | 224 ± 4 | 104 ± 16.5 |
| 53 | Compound 53 | >10 μM | N.A. | N.A. |
| 54 | Compound 54 | >10 μM | N.A. | N.A. |
| 56 | Compound 56 | >10 μM | N.A. | N.A. |
| 60 | Compound 60 | >10 μM | N.A. | N.A. |
| 61 | Compound 61 | 18.1 | 58.8 | 95 |
| 62 | Compound 62 | 19.3 | 68.3 | 116.8 ± 4.7 |
| 70 | Compound 70 | >616.2 | >5145.3 | N.A. |
| 75 | Compound 75 | 2.3 ± 0.6 | 7.2 ± 0.3 | 107 |
| 79 | Compound 79 | 227 ± 32 | 471 ± 110 | 103 |
| 80 | Compound 80 | 16.5 ± 1.1 | 21.0 ± 0.7 | 106 |
| 81 | Compound 81 | 6.9 ± 1.1 | 12.6 ± 0.9 | 103 |
| 86 | Compound 86 | 282 ± 13 | 197 ± 39 | 93 |
| 91 | Compound 91 | 176 ± 5.5 | 219 ± 25 | 93 |
| 92 | Compound 92 | 197 ± 19 | 539 ± 11 | 90 |
| 98 | Compound 98 | 14.2 ± 0.8 | 46.7 ± 7.3 | 95 |
| 99 | Compound 99 | >10 μM | N.A. | N.A. |
| 100 | Compound 100 | 470 ± 92 | 227 ± 15 | 105 |
| 101 | Compound 101 | 1447 ± 721 | N.A. | N.A. |
| 102 | Compound 102 | >10 μM | N.A. | N.A. |
| 103 | Compound 103 | 210 ± 32 | 348 ± 26 | 100 |
| 104 | Compound 104 | >10 μM | N.A. | N.A. |
| 105 | Compound 105 | >10 μM | N.A. | N.A. |
| | salvinorin A | 1.3 ± 0.5 | 4.5 ± 1.2 | 106 |
| | U50,488H | 1.4 ± 0.2 | 3.4 ± 0.5 | 100 |

[1] Percent of the maximal effect of U50,488H.
[2] N.A. is No Affinity.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A compound of formulas VIa or VIb:

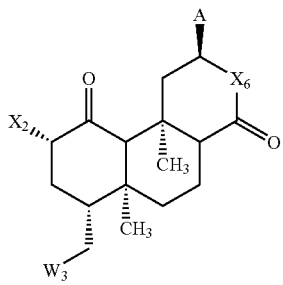
(VIa)

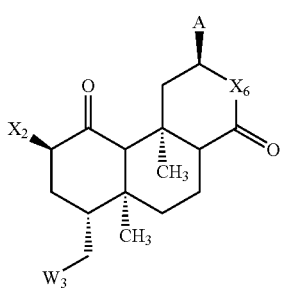
(VIb)

wherein
$W_3$ is selected from O—$R_3$, O-acyl, S—$R_3$, S-acyl, NH-acyl, NHC(O)NH-acyl, NHC(O)$Z_5$, and N$R_{29}R_{30}$;
A is selected from

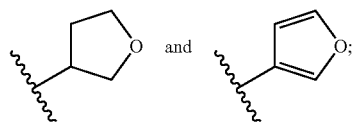

$X_2$ is selected from O—$R_2$, O-acyl, OC(O)$Z_2$, S—$R_2$, S-acyl, SC(O)$Z_2$, N$R_{16}R_{17}$, NH-acyl, NHC(O)NH-acyl, and NHC(O)$Z_2$;
$X_6$ is O;
$Z_2$ is O$R_2$, S$R_2$, or N$R_{16}R_{17}$;
$Z_5$ is O$R_{24}$, S$R_{24}$, or N$R_{25}R_{26}$; and
each of $R_2$, $R_3$, $R_{16}$, $R_{17}$, $R_{24}$, $R_{25}$, $R_{26}$, $R_{29}$, and $R_{30}$ is, independently, selected from H, $C_{1-8}$ alkyl, $C_{2-8}$ alkenyl, $C_{2-8}$ alkynyl, $C_{2-7}$ heterocyclyl, $C_{6-12}$ aryl, $C_{7-14}$ alkaryl, $C_{3-10}$ alkheterocyclyl, and $C_{1-8}$ heteroalkyl, or one or more of $R_{16}$ and $R_{17}$, $R_{25}$ and $R_{26}$, and $R_{29}$ and $R_{30}$ combine to form a heterocyclic ring containing a nitrogen atom and wherein said compound is a selective kappa receptor antagonist, a selective kappa receptor partial agonist, or a selective kappa receptor agonist.

2. The compound of formulas VIIc or VIId:

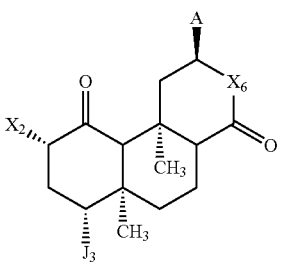
(VIIc)

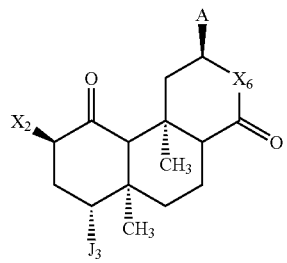
(VIId)

wherein
$J_3$ is selected from NH-acyl, NHC(O)NH-acyl, N$R_{31}R_{32}$, NHC(O)$Z_5$;
A is selected from

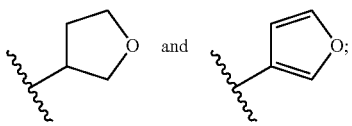

$X_2$ is selected from O—$R_2$, O-acyl, OC(O)$Z_2$, S—$R_2$, S-acyl, SC(O)$Z_2$, N$R_{16}R_{17}$, NH-acyl, NHC(O)NH-acyl, and NHC(O)$Z_2$;
$X_6$ is O;
$Z_2$ is O$R_2$, S$R_2$, or N$R_{16}R_{17}$;
$Z_5$ is O$R_{24}$, S$R_{24}$, or N$R_{25}R_{26}$; and
each of $R_2$, $R_{16}$, $R_{17}$, $R_{24}$, $R_{25}$, $R_{26}$, $R_{31}$, and $R_{32}$ is, independently, selected from H, $C_{1-8}$ alkyl, $C_{2-8}$ alkenyl, $C_{2-8}$ alkynyl, $C_{2-7}$ heterocyclyl, $C_{6-12}$ aryl, $C_{7-14}$ alkaryl, $C_{3-10}$ alkheterocyclyl, and $C_{1-8}$ heteroalkyl, or one or more of $R_{16}$ and $R_{17}$, $R_{25}$ and $R_{26}$, and $R_{31}$ and $R_{32}$ combine to form a heterocyclic ring containing a nitrogen atom and wherein said compound is a selective kappa receptor antagonist, a selective kappa receptor partial agonist, or a selective kappa receptor agonist.

3. The compound of formulas XIa or XIb:

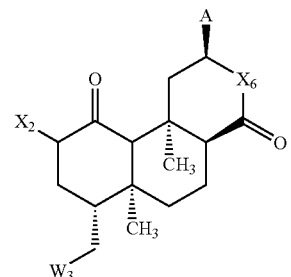
(XIa)

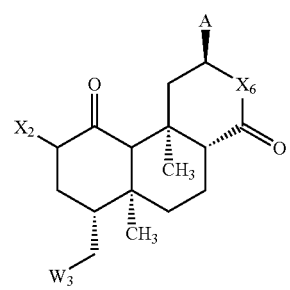
(XIb)

wherein
W$_3$ is selected from O—R$_3$, O-acyl, S—R$_3$, S-acyl, NH-acyl, NHC(O)NH-acyl, NHC(O)Z$_5$, and NR$_{29}$R$_{30}$;
A is selected from

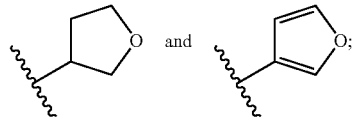

X$_2$ is selected from O—R$_2$, O-acyl, OC(O)Z$_2$, S—R$_2$, S-acyl, SC(O)Z$_2$, NR$_{16}$R$_{17}$, NH-acyl, NHC(O)NH-acyl, and NHC(O)Z$_2$;
X$_6$ is O;
Z$_2$ is OR$_2$, SR$_2$, or NR$_{16}$R$_{17}$;
Z$_5$ is OR$_{24}$, SR$_{24}$, or NR$_{25}$R$_{26}$; and
each of R$_2$, R$_3$, R$_{16}$, R$_{17}$, R$_{24}$, R$_{25}$, R$_{26}$, R$_{29}$, and R$_{30}$ is, independently, selected from H, C$_{1-8}$ alkyl, C$_{2-8}$ alkenyl, C$_{2-8}$ alkynyl, C$_{2-7}$ heterocyclyl, C$_{6-12}$ aryl, C$_{7-14}$ alkaryl, C$_{3-10}$ alkheterocyclyl, and C$_{1-8}$ heteroalkyl, or one or more of R$_{16}$ and R$_{17}$, R$_{25}$ and R$_{26}$, and R$_{29}$ and R$_{30}$ combine to form a heterocyclic ring containing a nitrogen atom and wherein said compound is a selective kappa receptor antagonist, a selective kappa receptor partial agonist, or a selective kappa receptor agonist.

4. The compound of formulas XXIIIa or XXIIIb:

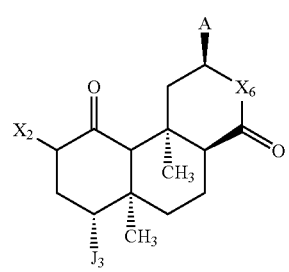

(XXIIIa)

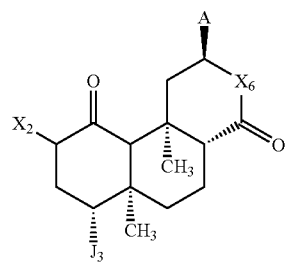

(XXIIIb)

wherein
J$_3$ is selected from NH-acyl, NHC(O)NH-acyl, NR$_{31}$R$_{32}$, NHC(O)Z$_5$;
A is selected from

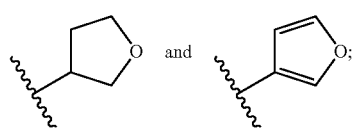

X$_2$ is selected from O—R$_2$, O-acyl, OC(O)Z$_2$, S—R$_2$, S-acyl, SC(O)Z$_2$, NR$_{16}$R$_{17}$, NH-acyl, NHC(O)NH-acyl, and NHC(O)Z$_2$;
X$_6$ is O;
Z$_2$ is OR$_2$, SR$_2$, or NR$_{16}$R$_{17}$;
Z$_5$ is OR$_{24}$, SR$_{24}$, or NR$_{25}$R$_{26}$; and each of R$_2$, R$_{16}$, R$_{17}$, R$_{24}$, R$_{25}$, R$_{26}$, R$_{31}$, and R$_{32}$ is, independently, selected from H, C$_{1-8}$ alkyl, C$_{2-8}$ alkenyl, C$_{2-8}$ alkynyl, C$_{2-7}$ heterocyclyl, C$_{6-12}$ aryl, C$_{7-14}$ alkaryl, C$_{3-10}$ alkheterocyclyl, and C$_{1-8}$ heteroalkyl, or one or more of R$_{16}$ and R$_{17}$, R$_{25}$ and R$_{26}$, and R$_{31}$ and R$_{32}$ combine to form a heterocyclic ring containing a nitrogen atom and wherein said compound is a selective kappa receptor antagonist, a selective kappa receptor partial agonist, or a selective kappa receptor agonist.

5. The compound of any of formulas XXIa-XXId:

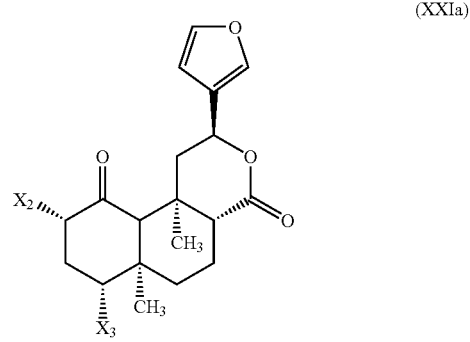

(XXIa)

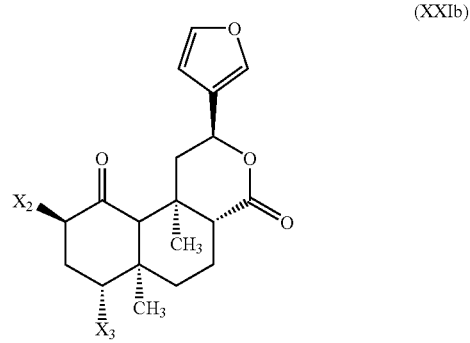

(XXIb)

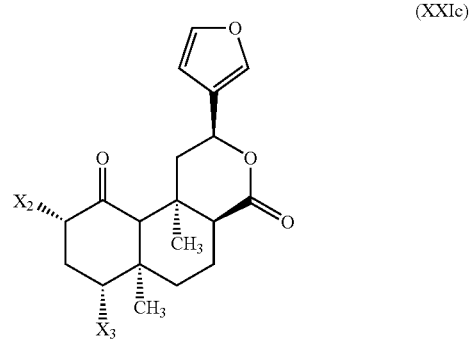

(XXIc)

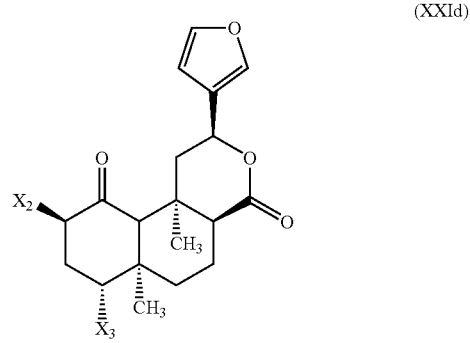

(XXId)

and pharmaceutically acceptable salts thereof, wherein
X$_2$ is selected from NR$_{16}$R$_{17}$, NH-acyl, NHC(O)NH-acyl, and NHC(O)Z$_2$;

X₃ is selected from CH₂O—R₃, CH₂O-acyl, CH₂S—R₃, CH₂S-acyl, CH₂NH-acyl, CH₂NHC(O)NH-acyl, CH₂NHC(O)Z₅, CH₂NR₂₉R₃₀, NH-acyl, NHC(O)NH-acyl, NR₃₁R₃₂, and NHC(O)Z₅;

Z₅ is OR₂₄, SR₂₄, or NR₂₅R₂₆; and each of R₃, R₁₆, R₁₇, R₂₉, R₃₀, R₃₁, R₃₂ is, independently, selected from H, $C_{1-8}$ alkyl, $C_{2-8}$ alkenyl, $C_{2-8}$ alkynyl, $C_{2-7}$ heterocyclyl, $C_{6-12}$ aryl, $C_{7-14}$ alkaryl, $C_{3-10}$ alkheterocyclyl, and $C_{1-8}$ heteroalkyl, or one or more of R₁₆ and R₁₇, R₂₉ and R₃₀, and R₃₁ and R₃₂ combine to form a heterocyclic ring containing a nitrogen atom.

6. The compound of formula XIXa:

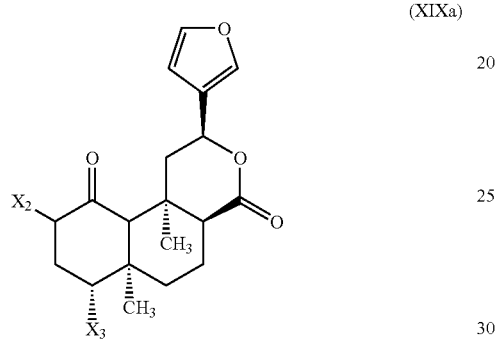

(XIXa)

wherein

X₂ is selected from H, O, S, O—R₂, O-acyl, OC(O)Z₂, NR₁₆R₁₇, NH-acyl, NHC(O)NH-acyl, and NHC(O)Z₂;

X₃ is selected from CH₂O—R₃, CH₂O-acyl, CH₂NH-acyl, CH₂NHC(O)NH-acyl, and C(O)—Y₁;

Y₁ is selected from OR₁₁ and NR₁₂R₁₃;

Z₂ is OR₂, SR₂, or NR₁₆R₁₇; and each of R₂, R₃, R₁₁, R₁₂, R₁₃, R₁₆, and R₁₇ is, independently, selected from H, $C_{1-8}$ alkyl, $C_{2-8}$ alkenyl, $C_{2-8}$ alkynyl, $C_{2-7}$ heterocyclyl, $C_{6-12}$ aryl, $C_{7-14}$ alkaryl, $C_{3-10}$ alkheterocyclyl, and $C_{1-8}$ heteroalkyl, or one or more of R₁₂ and R₁₃ and R₁₆ and R₁₇ combine to form a heterocyclic ring containing a nitrogen atom.

7. The compound selected from selected from episalvinorin A,

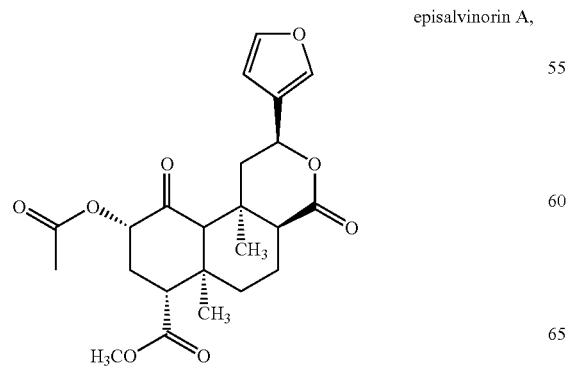

episalvinorin B,

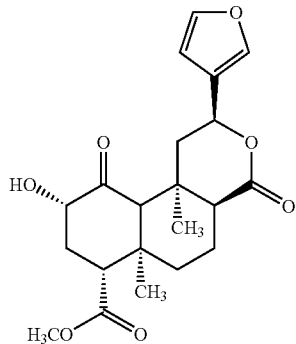

episalvinorin C, episalvinorin D, episalvinorin E,

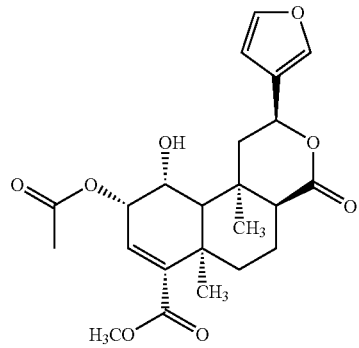

episalvinorin F,

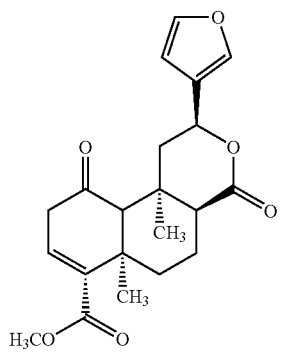

8. A compound of any of formulas XXIa-XXJd:

(XXIa)

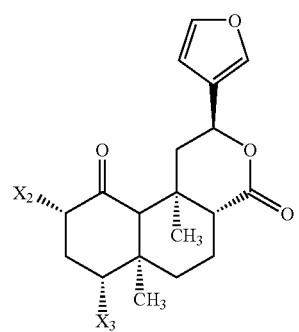

(XXIb)

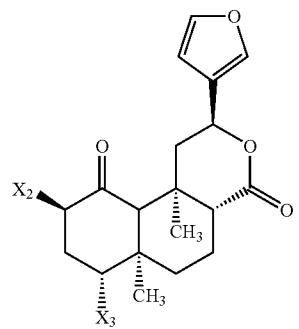

(XXIc)

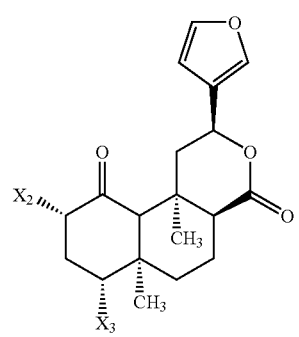

(XXId)

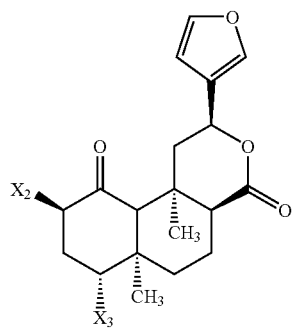

and pharmaceutically acceptable salts thereof, wherein $X_2$ is selected from $NR_{16}R_{17}$, NH-acyl, NHC(O)NH-acyl, and $NHC(O)Z_2$;

$X_3$ is $C(O)—Y_1$;

$Z_2$ is $OR_2$, $SR_2$, or $NR_{16}R_{17}$;

$Y_1$ is selected from $OR_{11}$, $SR_{11}$, and $NR_{12}R_{13}$; and each of $R_2$, $R_{11}$, $R_{12}$, $R_{13}$, $R_{16}$, and $R_{17}$ is, independently, selected from H, $C_{1-8}$ alkyl, $C_{2-8}$ alkenyl, $C_{2-8}$ alkynyl, $C_{2-7}$ heterocyclyl, $C_{6-12}$ aryl, $C_{7-14}$ alkaryl, $C_{3-10}$ alkheterocyclyl, and $C_{1-8}$ heteroalkyl, or one or more of $R_{12}$ and $R_{13}$, and $R_{16}$ and $R_{17}$ combine to form a heterocyclic ring containing a nitrogen atom.

9. A compound of any of formulas XXIa-XXId:

(XXIa)

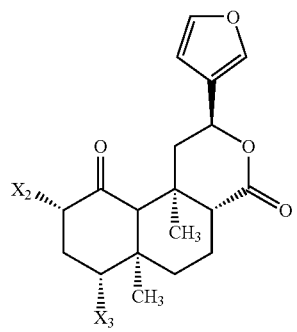

(XXIb)

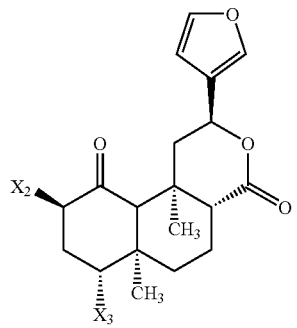

-continued (XXIc)

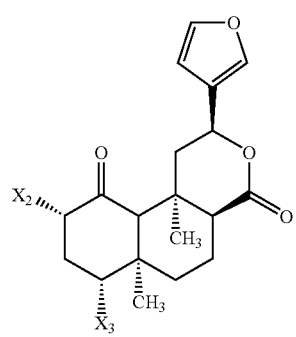

(XXId)

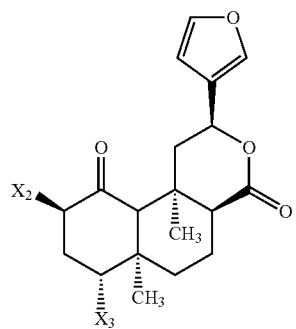

and pharmaceutically acceptable salts thereof, wherein

X$_2$ is selected from S—R$_2$, S-acyl and SC(O)Z$_2$;

X$_3$ is C(O)—Y$_1$;

Z$_2$ is OR$_2$, SR$_2$, or NR$_{16}$R$_{17}$;

Y$_1$ is selected from OR$_{11}$, SR$_{11}$, and NR$_{12}$R$_{13}$; and each of R$_2$, R$_{11}$, R$_{12}$, R$_{13}$, R$_{16}$, and R$_{17}$ is, independently, selected from H, C$_{1-8}$ alkyl, C$_{2-8}$ alkenyl, C$_{2-8}$ alkynyl, C$_{2-7}$ heterocyclyl, C$_{6-12}$ aryl, C$_{7-14}$ alkaryl, C$_{3-10}$ alkheterocyclyl, and C$_{1-8}$ heteroalkyl, or one or more of R$_{12}$ and R$_{13}$, and R$_{16}$ and R$_{17}$ combine to form a heterocyclic ring containing a nitrogen atom.

10. A compound described by the formula:

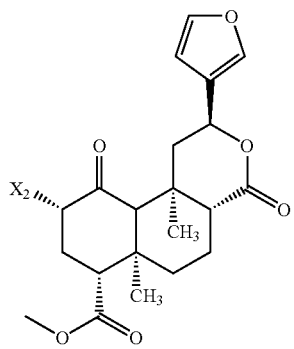

and pharmaceutically acceptable salts thereof, wherein

X$_2$ is selected from NR$_{16}$R$_{17}$, NH-acyl, NHC(O)NH-acyl, and NHC(O)Z$_2$;

Z$_2$ is OR$_2$, SR$_2$, or NR$_{16}$R$_{17}$;

each of R$_2$, R$_{16}$, and R$_{17}$ is, independently, selected from H, C$_{1-8}$ alkyl, C$_{2-8}$ alkenyl, C$_{2-8}$ alkynyl, C$_{2-7}$ heterocyclyl, C$_{6-12}$ aryl, C$_{7-14}$ alkaryl, C$_{3-10}$ alkheterocyclyl, and C$_{1-8}$ heteroalkyl, or one or more of R$_{12}$ and R$_{13}$, and R$_{16}$ and R$_{17}$ combine to form a heterocyclic ring containing a nitrogen atom.

11. A compound selected from:

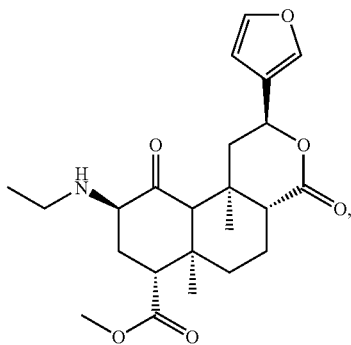

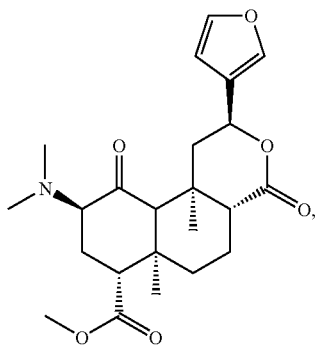

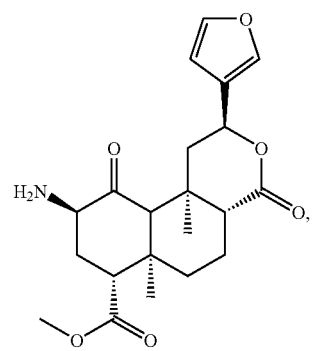

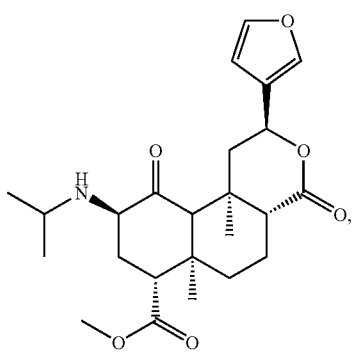

83
-continued
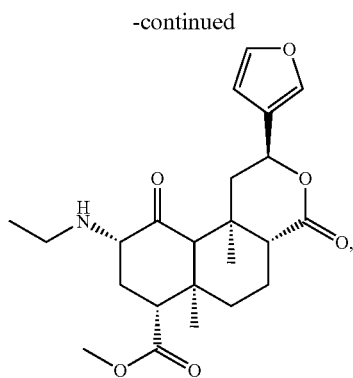
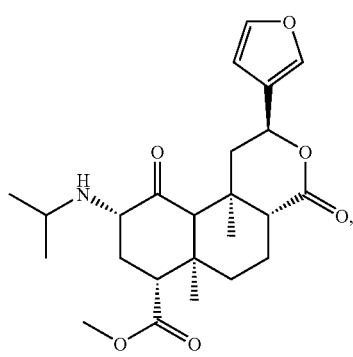
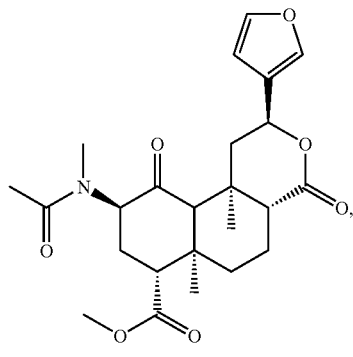
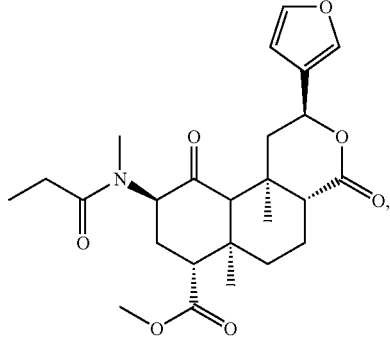
84
-continued
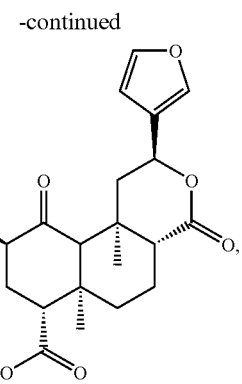
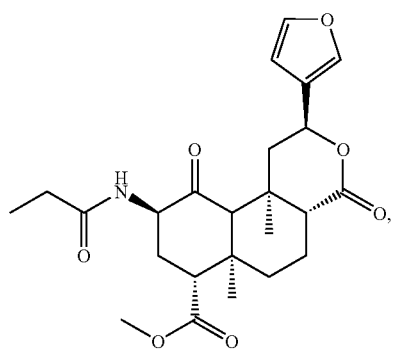
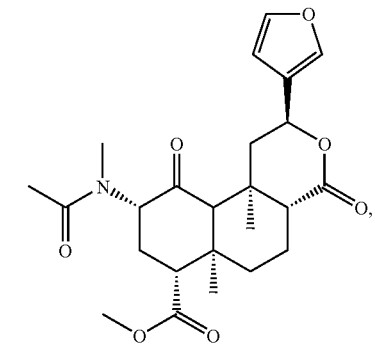
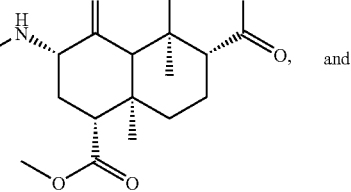
and -continued

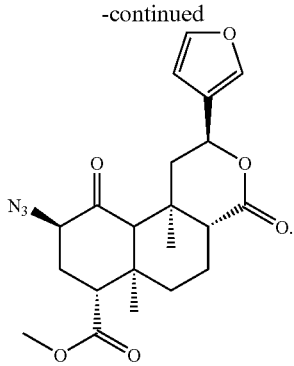

12. The compound of claim 11, wherein said compound is:

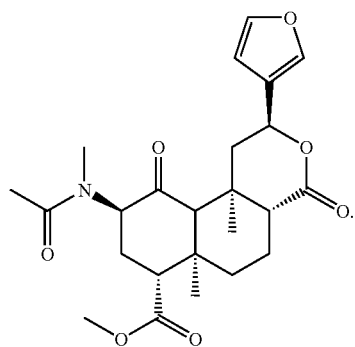

13. A compound described by the formula:

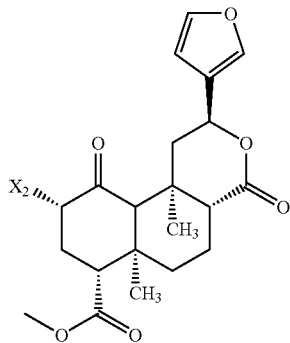

and pharmaceutically acceptable salts thereof, wherein
$X_2$ is selected from S—$R_2$, S-acyl and $SC(O)Z_2$;
$Z_2$ is $OR_2$, $SR_2$, or $NR_{16}R_{17}$;
each of $R_2$, $R_{16}$, and $R_{17}$ is, independently, selected from H, $C_{1-8}$ alkyl, $C_{2-8}$ alkenyl, $C_{2-8}$ alkynyl, $C_{2-7}$ heterocyclyl, $C_{6-12}$ aryl, $C_{7-14}$ alkaryl, $C_{3-10}$ alkheterocyclyl, and $C_{1-8}$ heteroalkyl, or one or more of $R_{12}$ and $R_{13}$, and $R_{16}$ and $R_{17}$ combine to form a heterocyclic ring containing a nitrogen atom.

* * * * *

UNITED STATES PATENT AND TRADEMARK OFFICE
CERTIFICATE OF CORRECTION

PATENT NO. : 7,629,475 B2  
APPLICATION NO. : 11/079825  
DATED : December 8, 2009  
INVENTOR(S) : Béquin et al.

It is certified that error appears in the above-identified patent and that said Letters Patent is hereby corrected as shown below:

On the Title Pg, Item (56) under OTHER PUBLICATIONS, in Chavkin et al., replace "vol. 304" with --vol. 308--;

Item (56) under OTHER PUBLICATIONS, in Koreeda et al., replace "vol. 11" with --vol. 19--;

Item (56) under OTHER PUBLICATIONS, in Carlezon et al., replace "opiold" with --opioid--.

Page 2, Item (56) under OTHER PUBLICATIONS, in Siebert, Daniel J., replace "*Salvio*" with --*Salvia*--.

Column 14, Line 59, replace "C," with --$C_1$--.

Column 15, Line 43, replace "intraparenchemal" with --intraparenchymal--.

Column 26, Line 63, replace "subsituents" with --substituents--.

Signed and Sealed this  
First Day of May, 2012

David J. Kappos  
*Director of the United States Patent and Trademark Office*

UNITED STATES PATENT AND TRADEMARK OFFICE
CERTIFICATE OF CORRECTION

PATENT NO. : 7,629,475 B2
APPLICATION NO. : 11/079825
DATED : December 8, 2009
INVENTOR(S) : Cecile Beguin et al.

It is certified that error appears in the above-identified patent and that said Letters Patent is hereby corrected as shown below:

Column 1, following the CROSS REFERENCE TO RELATED APPLICATIONS section, please insert the following new paragraph:

--STATEMENT AS TO FEDERALLY SPONSORED RESEARCH

This invention was made with Government support under Grant No. DA04123, MH63266, and DA017204 awarded by the National Institutes of Health. The government has certain rights in the invention.--.

Signed and Sealed this
Twenty-sixth Day of February, 2013

Teresa Stanek Rea
*Acting Director of the United States Patent and Trademark Office*